US008609421B2

(12) United States Patent
Flusberg et al.

(10) Patent No.: US 8,609,421 B2
(45) Date of Patent: Dec. 17, 2013

(54) SINGLE-MOLECULE REAL-TIME ANALYSIS OF PROTEIN SYNTHESIS

(75) Inventors: Benjamin Flusberg, Palo Alto, CA (US); Stephen Turner, Menlo Park, CA (US); Jonas Korlach, Newark, CA (US); Eric Schadt, Palo Alto, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 332 days.

(21) Appl. No.: 12/813,968

(22) Filed: Jun. 11, 2010

(65) Prior Publication Data

US 2010/0317116 A1 Dec. 16, 2010

Related U.S. Application Data

(60) Provisional application No. 61/186,645, filed on Jun. 12, 2009.

(51) Int. Cl.
*G01N 37/00* (2006.01)

(52) U.S. Cl.
USPC .............. 436/56; 436/94; 435/317.1; 435/6.1

(58) Field of Classification Search
None
See application file for complete search history.

(56) References Cited

U.S. PATENT DOCUMENTS

| | | | |
|---|---|---|---|
| 5,643,722 A | 7/1997 | Rothschild et al. | |
| 5,648,245 A | 7/1997 | Fire et al. | |
| 5,714,320 A | 2/1998 | Kool | |
| 6,255,083 B1 | 7/2001 | Williams | |
| 6,261,808 B1 | 7/2001 | Auerbach | |
| 6,787,308 B2 | 9/2004 | Balasubramanian et al. | |
| 6,875,592 B2 | 4/2005 | Rothschild et al. | |
| 6,917,726 B2 | 7/2005 | Levene et al. | |
| 7,056,661 B2 | 6/2006 | Korlach et al. | |
| 7,101,662 B2 | 9/2006 | Rothschild et al. | |
| 7,170,050 B2 | 1/2007 | Turner et al. | |
| 7,297,532 B2 | 11/2007 | Puglisi et al. | |
| 7,312,060 B2 | 12/2007 | Rothschild et al. | |
| 7,329,492 B2 | 2/2008 | Hardin et al. | |
| 7,476,503 B2 | 1/2009 | Turner et al. | |
| 2003/0219783 A1 | 11/2003 | Puglisi et al. | |
| 2004/0023256 A1 | 2/2004 | Puglisi et al. | |

(Continued)

FOREIGN PATENT DOCUMENTS

| WO | WO 03/064604 A2 | 8/2003 |
|---|---|---|
| WO | WO 03/064608 A2 | 8/2003 |

(Continued)

OTHER PUBLICATIONS

Perriman, R. et al. Circular mRNA can direct translation of extremely long repeating-sequence proteins in vivo, 1998, RNA, vol. 4, pp. 1047-1054.*

(Continued)

*Primary Examiner* — Robert Xu
(74) *Attorney, Agent, or Firm* — Deana A. Arnold

(57) ABSTRACT

The present invention is generally directed to compositions, methods, and systems for performing single-molecule, real-time analysis of analytical reactions in which protein synthesis is occurring. The ability to analyze such reactions provides an opportunity to study those reactions as well as to potentially identify factors and/or approaches for impacting such reactions, e.g., to either enhance, inhibit, or otherwise affect such reactions including, but not limited to, affecting the reaction rate, processivity, fidelity, duration, and the like.

16 Claims, 12 Drawing Sheets

(56) References Cited

U.S. PATENT DOCUMENTS

| | | |
|---|---|---|
| 2005/0032078 A1 | 2/2005 | Rothschild et al. |
| 2006/0228708 A1 | 10/2006 | Smilansky |
| 2009/0081643 A1 | 3/2009 | Preminger et al. |
| 2010/0062451 A1 | 3/2010 | Lim et al. |
| 2010/0075374 A1 | 3/2010 | Lim et al. |

FOREIGN PATENT DOCUMENTS

| | | |
|---|---|---|
| WO | WO 2004/050825 A2 | 6/2004 |
| WO | WO 2005/116252 A2 | 12/2005 |
| WO | WO 2009/002866 A1 | 12/2008 |

OTHER PUBLICATIONS

Daubendiek, S. L. et al. Genetation of catalytic RNAs by rolling transcription of synthetic DNA nanocircles, 1997, Nature Biochemistry, vol. 15, pp. 273-277.*

Levene, M. J. et al., Zero-Mode Waveguides for single-molecule analysis at high concentrations, 2003, Science, vol. 299, pp. 682-686.*

Betteridge, et al., RNA 13:1594-1601 (2009).

Blanchard, et at, Proc. Natl. Acad. Sci. USA 101(35): 12893-12898 (2004).

Chen, et al., Science 268:415-417 (1995).

Cwirla, et al., Proc. Natl. Acad. Sci. USA 87:6378-6382 (1990).

Eid et al., Science 323:133-138 (Jan. 2, 2009).

Geslain, et al., J. Mol. Biol. 396 :821-831 (2010).

Hohsaka, et al., Nuc. Ac. Res. Suppl. No. 3 271-272 (2003).

Karlsson, et al., Biochimie 81 :995-1002 (1999).

Kothe, et al., Biochemistry 45:12767-12774 (2006).

Krzyzaniak, et al., Int. J. Biol. Macromol. 16(3):153-158 (1994).

Levene et al., Science 299 (5607):682-686 (2003).

Lim, et al., Anal. Biochem. 383:103-115 (2008).

Miyake, et al. Anal. Chem. 80:6018-6022 (2008).

Odom, et al., Biochemistry 29(48):10734-10744 (1990).

Pan, et al., RNA 15:346-354 (2009).

Salmon, et al., Proc. Natl. Acad. Sci. USA 90:11708-11712 (1993).

Scheper, et al., Nat. Rev. 8:711-723 (2007).

Sytnik, et al., J. Mol. Biol. 285:49-54 (1999).

Uemura, et al., Nature 464:1012-1017 (2010).

Uemura, et al, Nuc. Ac. Res. 36(1 2):e70 (2008).

Vanzi, et al., Biophys. J. 89:1909-1919 (2005).

Vanzi, et al., RNA 9:1174-1179 (2003).

Wang, et al., Biochemistry 46:10767-10775 (2007).

Watson, et al., Biochemistry 34:7904-7912 (1995).

International Search Report issued Mar. 28, 2011 for corresponding PCT application PCT/US/2010/001692.

International Preliminary Report on Patentability issued Dec. 22, 2011 for corresponding PCT application PCT/US2010/001692.

* cited by examiner

SINGLE-MOLECULE REAL-TIME ANALYSIS OF PROTEIN SYNTHESIS

CROSS-REFERENCE TO RELATED APPLICATIONS

This application claims the benefit of U.S. Provisional Application No. 61/186,645, filed Jun. 12, 2009, the full disclosure of which is incorporated herein by reference in its entirety for all purposes.

STATEMENT REGARDING FEDERALLY SPONSORED RESEARCH

Not Applicable.

BACKGROUND OF THE INVENTION

Assays for analysis of biological processes are exploited for a variety of desired applications. For example, monitoring the activity of key biological pathways can lead to a better understanding of the functioning of those systems as well as those factors that might disrupt the proper functioning of those systems. In fact, various different disease states caused by operation or disruption of specific biological pathways are the focus of much medical research. By understanding these pathways, one can model approaches for affecting them to prevent the onset of the disease or mitigate its effects once manifested.

An example of the exploitation of biological process monitoring is in the area of pharmaceutical research and development. In particular, therapeutically relevant biological pathways, or individual steps or subsets of individual steps in those pathways, are often reproduced or modeled in in vitro systems to facilitate analysis. By observing the progress of these steps or whole pathways in the presence and absence of potential therapeutic compositions, e.g., pharmaceutical compounds or other materials, one can identify the ability of those compositions to affect the in vitro system, and potentially beneficially affect an organism in which the pathway is functioning in a detrimental way. By way of specific example, a variety of kinase enzymes have been identified as key pathway components in a number of therapeutically relevant biological pathways, as they will often phosphorylate different substrate proteins upon the binding of different effector compounds, e.g., cytokines, to receptors on biological proteins, e.g., cell surface receptors. By modeling the kinase reaction system in vitro and testing it against libraries of potential pharmaceutical candidates, one can identify the compounds which best inhibit or enhance the reaction in question.

Typically, modeled biological systems rely on bulk reactions that ascertain general trends of biological reactions and provide indications of how such bulk systems react to different effectors. While such systems are useful as models of bulk reactions in vivo, a substantial amount of information is lost in the averaging of these bulk reaction results. In particular, the activity of and effects on individual molecular complexes cannot generally be teased out of such bulk data collection strategies.

Single-molecule real-time analysis of nucleic acid synthesis has been shown to provide powerful advantages over nucleic acid synthesis monitoring, which is commonly exploited in sequencing processes. In particular, by concurrently monitoring the synthesis process of nucleic acid polymerases as they work in replicating nucleic acids, one gains advantages of a system that has been perfected over millions of years of evolution. In particular, the natural DNA synthesis processes provide the ability to replicate whole genomes in extremely short periods of time, and they do so with an extremely high level of fidelity to the underlying template being replicated.

The present invention is directed to certain single-molecule real-time analyses for monitoring the progress and effectors of biological reactions and, in certain preferred embodiments, is particularly directed analytical reactions monitoring various aspects of polypeptide synthesis.

BRIEF SUMMARY OF THE INVENTION

The present invention is generally directed to compositions, methods, and systems for performing single-molecule, real-time analysis of analytical reactions in which protein synthesis is occurring. The ability to analyze such reactions provides an opportunity to study those reactions as well as to potentially identify factors and/or approaches for impacting such reactions, e.g., to either enhance, inhibit, or otherwise affect such reactions including, but not limited to, affecting the reaction rate, processivity, fidelity, duration, error profile, regulation of initiation and/or termination, and the like.

Certain methods of the invention exploit the optical isolation properties of optical confinement techniques, such as zero mode waveguide technology, total internal reflection fluorescence (TIRF) microscopy, optical waveguide technology, and the like. In particular, the invention provides for observation of a single reaction component during the course of the reaction, and in preferred embodiments it provides for sequential observation of individual members of a set of reaction components over the course of the reaction. For example, the reaction components can be observed in interaction with additional reactants at the single-molecule (or single molecular complex) level in order to monitor the progress of the reaction of interest. In certain preferred embodiments, a reaction of interest is carried out in an optical confinement, as described below. A plurality of analytical reactions may also be carried out in an array of optical confinements, e.g., on a single solid support or other substrate. Analytical reactions in an array of optical confinements can be carried out simultaneously, and may or may not be synchronized with one another.

In certain aspects, the invention provides a method of determining a sequence of amino acids encoded by a target mRNA molecule, comprising providing a reaction mixture comprising the target mRNA molecule, a ribosome complex, and a plurality of types of labeled aminoacyl-tRNAs free in solution, wherein the ribosome and/or the target mRNA molecule is immobilized upon a support such that an observation volume contains no more than one ribosome and/or mRNA molecule; initiating a processive translation of the mRNA molecule by the ribosome complex; sequentially and optically detecting association of the ribosome complex with at least a first labeled aminoacyl-tRNA and a second labeled aminoacyl-tRNA, where said association results in an incorporation of a first amino acid from the first labeled aminoacyl-tRNA and a second amino acid from the second labeled aminoacyl-tRNA into a nascent polypeptide chain; and identifying the first amino acid and the second amino acid, thereby determining a sequence of amino acids encoded by the target mRNA molecule. In certain preferred embodiments, the ribosome complex does not comprise a detectable label or a quenching group. In certain preferred embodiments, the ribosome complex comprises fMET-tRNA$^{fMet}$ in the P site. In certain embodiments, at least 4-20 labeled aminoacyl-tRNAs are present in the reaction mixture. In certain embodiments, the reaction mixture further comprises a plurality of types of unlabeled aminoacyl-tRNAs free in solution. In some embodiments, each of the plurality of types of labeled aminoacyl-tRNAs each comprise a different (e.g., optically distinguishable) type of detectable label, e.g., a fluorescent dye produces an emission in response to excitation radiation. In other embodiments, the labeled aminoacyl-tRNAs each comprise a different FRET acceptor and the reaction mixture further comprises a FRET donor that excites the FRET acceptor. For example, the FRET donor may be linked to various reaction components, including but not limited to one or more elongation factors (e.g., EF-Tu or EF-G) or cofactors (e.g., GTP). In certain embodiments, the reaction mixture further comprises a signal quencher linked to a reaction component. In certain embodiments, the target mRNA molecule is a circular mRNA molecule. In other embodiments, the target mRNA molecule is a linear concatemer mRNA molecule, e.g., a product of transcription of a circular DNA template molecule. In some embodiments, the reaction mixture further comprises aminoacyl-synthetases, e.g., bound to beads that prevent entry of the aminoacyl-synthetases into the reaction site. In certain embodiments, each of the plurality of types of labeled aminoacyl-tRNAs comprises (i) a different amino acid and a label that distinguishes the different amino acid from other amino acids in others of the plurality of types of labeled aminoacyl-tRNAs, and (ii) an anticodon that is complementary to a codon that may be present in the target mRNA molecule.

Also provided is a polypeptide sequencing method comprising subjecting a target RNA molecule to a polypeptide synthesis reaction to yield a nascent polypeptide that is encoded by the target RNA molecule in the presence of a ribosome complex and a plurality of differentially labeled aminoacyl-tRNAs, wherein the polypeptide synthesis reaction processes an identical sequence of nucleotides in the target RNA molecule more than once. The method further comprises (a) individually detecting each type of said aminoacyl-tRNA by virtue of the detectable label comprised therein, wherein said detecting comprises exposing said polypeptide synthesis reaction to excitation radiation having a wavelength that is within an absorption spectrum of the detectable label; and (b) recording an order of each type of said aminoacyl-tRNA detected in step a, wherein the order corresponds to a sequence of the polypeptide synthesized in the polypeptide synthesis reaction. In certain embodiments, each type of differentially labeled aminoacyl-tRNA comprises (i) a detectable label that is optically distinguishable from every other detectable label in every other type of differentially labeled aminoacyl-tRNA, and (ii) an amino acid portion that is different from that of every other type of differentially labeled aminoacyl-tRNA. In some embodiments, the target RNA molecule is a circular RNA molecule, and in other embodiments the target RNA molecule is a linear RNA molecule. In some embodiments, the target RNA molecule comprises a sequence of nucleotides that is present multiple times within the target RNA molecule. For example, the target RNA molecule may be a linear or circular concatemer RNA molecule, and may be the product of transcription of a circular DNA template molecule. In certain preferred embodiments, the polypeptide synthesis reaction processes a sequence of nucleotides in the target RNA molecule multiple times, e.g., in the case of a circular or concatemer RNA molecule. In some embodiments, the ribosome complex is attached to a support, and in preferred embodiments, the ribosome complex is optically resolvable from any other ribosome complex also attached to the support. In certain preferred embodiments, the polypeptide synthesis reaction takes place within an optical confinement, e.g., a zero mode waveguide, as described elsewhere herein. The detecting and recording can be performed in real time during the polypeptide synthesis reaction.

The invention also provides a method for identifying a variant amino acid at a polymorphic position in a polypeptide. In certain embodiments, an immobilized complex is provided that comprises a ribosome and an RNA encoding the polypeptide, wherein a codon in the RNA encoding the polymorphic position is configured to receive a complementary anticodon. A plurality of differentially labeled aminoacyl-tRNAs comprising an anticodon, a cognate amino acid, and a detectable label that identifies the cognate amino acid are introduced to the reaction mixture, and at least one of the plurality comprises the complementary anticodon and the variant amino acid. Incorporation of the variant amino acid into the polypeptide is detected by virtue of the detectable label, thereby identifying the variant amino acid at the polymorphic position in the polypeptide.

In other aspects, a composition is provided that comprises an optical confinement, a ribosome in the optical confinement, an mRNA bound to the ribosome, a labeled aminoacyl-tRNA in association with the ribosome and the mRNA, wherein the labeled aminoacyl-tRNA comprises a FRET acceptor, and a labeled elongation factor complex comprising a FRET donor that excites the FRET acceptor. In certain embodiments, the FRET donor is linked to EF-Tu, EF-G, and/or GTP in the elongation factor complex. In certain embodiments, the ribosome does not comprise a label or quenching group. In some embodiments the mRNA is a circular mRNA, and in other embodiments that mRNA is a linear mRNA, e.g., optionally a concatemer mRNA.

In further aspects, a system suitable for determining a sequence of a polypeptide chain encoded by an mRNA molecule is provided. The system comprises a support comprising an array of optical confinements, a single complex comprising a ribosome and an mRNA molecule in a single optical confinement in the array, a reaction mixture on the array, and an optical system for detecting signals emitted from a plurality of detectable labels.

In yet further aspects, a method of monitoring the impact of an agent on translation of an RNA molecule is provided. The method comprises subjecting multiple copies of the RNA molecule to separate polypeptide synthesis reactions, some in the absence of the agent and some in the presence of the agent. Each of the polypeptide synthesis reactions generates a set of reaction characteristics, which can comprise, e.g., a sequence of amino acids of a polypeptide encoded by the RNA molecule and/or a set of measures of certain aspects of the reaction, including but not limited to rate of incorporation, rate of translocation, time between amino acid incorporation events, time between binding of subsequent aa-tRNAs, fidelity, processivity, duration, error profile, efficiency, binding affinity, rate of catalysis, association constant, dissociation constant, rate of association, and rate of dissociation. The reaction characteristics of the polypeptide synthesis reactions are analyzed to identify the impact, if any, of the agent on translation of the RNA molecule. In some embodiments, analyzing the results involves comparing the sequences of amino acids generated in the presence of the agent to amino acid sequences generated in the absence of the agent, wherein a difference is indicative of the impact of the agent. In some embodiments, analyzing the results involves statistical analysis of kinetic characteristics of the polypeptide synthesis reactions in the presence and absence of the agent, wherein a difference is indicative of the impact of the agent. The agent can be a reaction condition or an additive to the reaction. In certain embodiments, the agent is at least one of a small molecule, drug, drug candidate, miRNA, siRNA, piRNA, CRISPR RNA, tmRNA, antisense RNA, antibody, nucleic acid binding agent, modification-binding agent, cofactor, toxin, metal ion, divalent cation, monovalent cation, activator, inhibitor, change in reaction temperature, buffer change, acid, base, and antibiotic. In some embodiments, the agent is a mixture of different types of agents, and optionally each different type of agent comprises a label that distinguishes it from every other type of agent, as well as indicating its presence at a particular reaction site. In certain preferred embodiments, the polypeptide synthesis reactions are carried out in a way to promote processive translation of the RNA molecule and/or to increase the length of the translation reaction, thereby increasing the timecourse of the reaction to better facilitate analysis of various kinetic aspects of the reactions. For example, the RNA molecule may be circular to allow sequential repeated translation of the same template. Alternatively or additionally, the RNA molecule may be a concatemer comprising multiple copies of a sequence of interest to allow sequential repeated translation of the sequence of interest. In certain embodiments, the polypeptide synthesis reactions comprise a set of labeled aminoacyl-tRNAs, each of which comprises a FRET acceptor that specifies a cognate amino acid of the labeled aminoacyl-tRNA; and a labeled elongation factor complex comprising a FRET donor that excites the FRET acceptor. For example, the FRET donor can be linked to a component of the elongation factor complex selected front EF-Tu, EF-G, and GTP.

Also provided is a method of monitoring the characteristics of transcription of a single RNA molecule. In certain embodiments, the method provides a reaction mixture comprising the single RNA molecule, a ribosome complex, and a plurality of types of labeled aminoacyl-tRNAs free in solution. Preferably, the ribosome complex does not comprise a detectable label or a quenching group. Processive translation of the RNA molecule by the ribosome complex is initiated, and association of the ribosome complex with a plurality of labeled aminoacyl-tRNAs is sequentially and optically detected. The association of the ribosome complex with the plurality of aminoacyl-tRNAs results in incorporation of a set of amino acids from at least a portion of the labeled aminoacyl-tRNAs into a nascent polypeptide chain, and one or more characteristics of the translation reaction are recorded. The characteristics can include nascent polypeptide sequence, various rates (e.g., association, dissociation, incorporation, translocation, catalysis, etc.), association and dissociation constants, binding affinities, efficiency, processivity, duration, error profiles, and other kinetic parameters, such as time between binding of subsequent aminoacyl-tRNAs, and time between subsequent amino acid incorporation events. In some embodiments, an average time per incorporation event is computed, thereby monitoring the rate at which the single RNA molecule is translated. In certain embodiments, the one or more characteristics recorded are indicative of a modification in the RNA molecule being translated, e.g., secondary or tertiary structure, an unnatural, damaged, methylated or otherwise modified base, or an abasic site.

In a further aspect, a method of identifying a protein encoded by a single mRNA molecule with no prior knowledge of the nucleotide sequence of the coding region of the mRNA molecule is provided. In preferred embodiments, the method includes providing a reaction mixture comprising the mRNA molecule, a ribosome complex, and a plurality of types of labeled aminoacyl-tRNAs free in solution and initiating translation of the mRNA molecule by the ribosome complex. During translation, incorporation of a set of amino acids into the nascent polypeptide chain is sequentially (e.g., optically) detected, and the set of amino acids comprises amino acids from at least a portion of the plurality of labeled aminoacyl-tRNAs, and wherein the polypeptide chain is at least a portion of the protein. A sequence of the set of amino acids is analyzed to generate sequence data for the nascent polypeptide chain, and the sequence data is used to identify the protein. In certain embodiments, the ribosome complex does not comprise a detectable label or a quenching group. In certain embodiments, the reaction mixture further comprises a plurality of types of unlabeled aminoacyl-tRNAs free in solution that are able to be incorporated into the nascent polypeptide chain. In some embodiments, the sequence data generated provides information for only a portion of the set of amino acids incorporated into the polypeptide chain. In certain embodiments, multiple copies of the mRNA molecule are subjected to separate translation reactions that comprise different sets of labeled aminoacyl-tRNAs. The sequence data generated from these separate translation reactions is collectively used to identify the protein. In certain embodiments, the sequence data is analyzed with regard to known amino acid sequences for a set of candidate proteins to identify the protein encoded by the mRNA molecule.

In certain aspects, the invention also provides kits for performing the various methods of the invention, e.g., with biological samples. The biological samples can be from any source, e.g., model systems, cell cultures, tissue cultures, or samples taken from one or more individual sources, e.g., environmental samples, agricultural samples, forensic samples, livestock samples, samples from laboratory animals, or samples from humans.

DETAILED DESCRIPTION OF THE INVENTION

Figure 1:
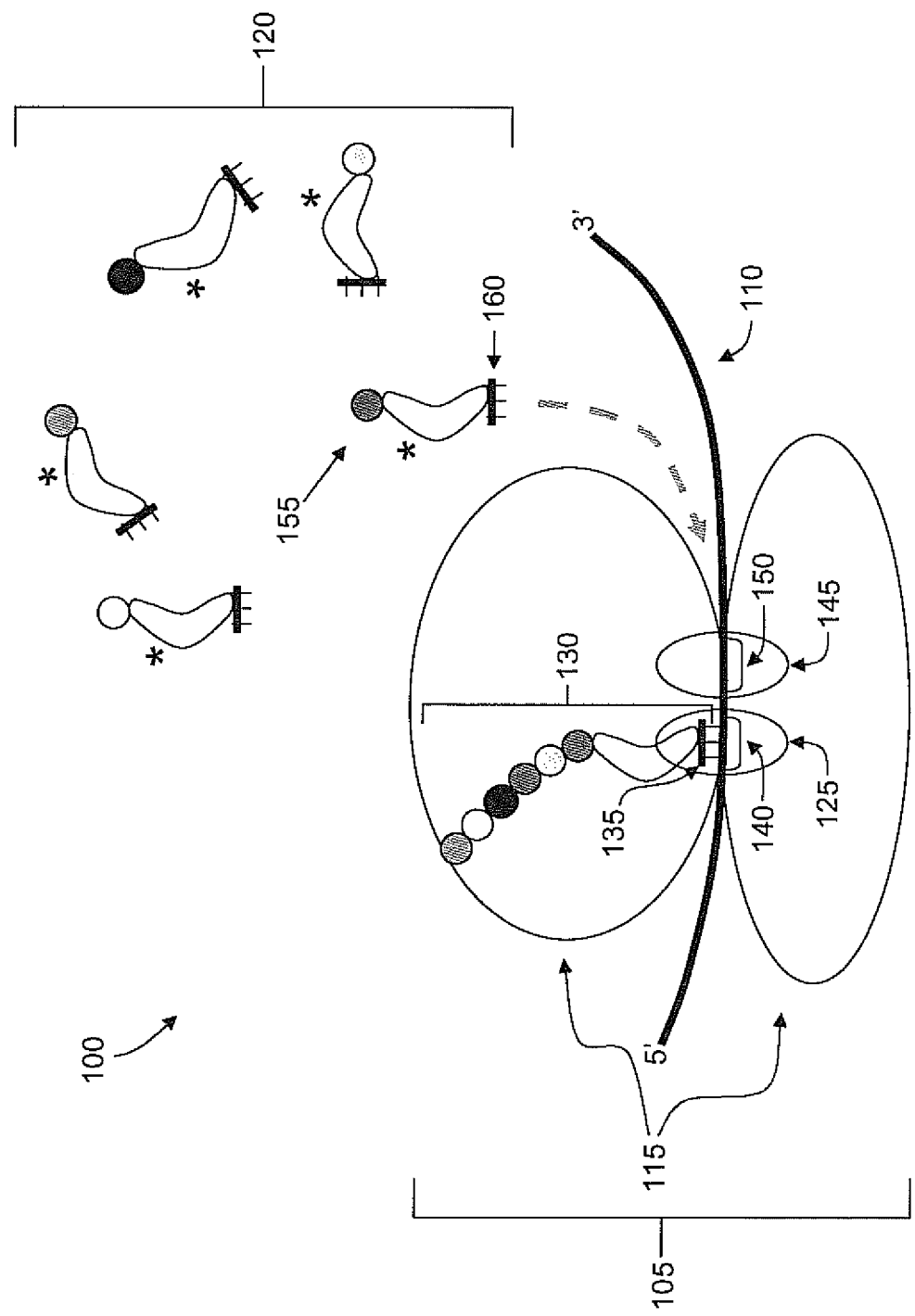
FIG. 1 provides an illustrative example of certain embodiments of various aspects of a protein synthesis reaction to be monitored and analyzed by the methods and systems of the invention.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

I. General

The present invention is generally directed to compositions, methods, and systems for performing single-molecule, real-time analysis of analytical reactions in which protein synthesis is occurring. The ability to analyze such reactions provides an opportunity to study those reactions as well as to potentially identify factors and/or approaches for impacting such reactions, e.g., to either enhance, inhibit, or otherwise affect such reactions including, but not limited to, affecting the reaction rate, processivity, fidelity, duration, error profile, other kinetic parameters, and the like.

Certain methods of the invention exploit the optical isolation properties of optical confinement techniques, such as zero mode waveguide technology, total internal reflection fluorescence (TIRF) microscopy, optical waveguide technology, and the like. In particular, the invention provides for observation of a single reaction component during the course of the reaction, and in preferred embodiments it provides for sequential observation of a set of single reaction components over the course of the reaction. For example, the reaction components can be observed in interaction with additional reactants at the single-molecule (or single molecular complex) level in order to monitor the progress of the reaction of interest. In certain preferred embodiments, a reaction of interest is carried out in an optical confinement, as described below. In preferred embodiments, the methods monitor optically detectable labels inside an optical confinement, such that a single reactant comprising an optically detectable label is distinguishable from a different single reactant comprising a different optically detectable label. A plurality of analytical reactions may also be carried out in an array of optical confinements, e.g. on a single solid support or other substrate. Analytical reactions in an array of optical confinements can be carried out simultaneously, and may or may not be synchronized with one another. Preferably, in such an array, a reaction taking place in a first optical confinement is optically resolvable from a reaction taking place in a second optical confinement, and they two reactions can therefore be monitored simultaneously and independently.

The monitoring typically takes the form of providing the interaction with a signaling event that is characteristic or indicative of that interaction. For example, such a signaling event can comprise the retention of a labeled reactant within a given observation region (e.g., in an optical confinement), or the interaction of two or more interactive labeling components to produce a signal characteristic of the interaction, e.g., based upon proximity of two interacting label components. In some embodiments, the labels emit optical signals that are detected by an optical detection system operably linked to a reaction site at which the analytical reaction is taking place. As used herein, a reaction site is a location on or adjacent to a substrate at which an analytical reaction is monitored, and it may refer to, e.g., a position on the substrate at which one or more components of an analytical reaction are immobilized or to an effective observation volume (or "detection volume") within which an analytical reaction is monitored. The detected signals are analyzed to determine a characteristic of the analytical reaction, e.g., initiation, termination, biochemical event (e.g., binding, bond cleavage, conformational change, etc.), substrate utilization, product formation, kinetic characteristics of the reaction (e.g., rate, time between subsequent biochemical events, time between the beginning/end of subsequent biochemical events, processivity, error profile, etc.), and the like. For example, characteristics of a protein synthesis reaction include the identity of an amino acid incorporated into a growing polypeptide chain, fidelity of correct incorporation by the ribosome complex, the rate of binding of an amino-acyl tRNA to the ribosome, the rate of incorporation of an amino acid into the growing polypeptide chain, the length of the polypeptide synthesized, and/or other aspects of the kinetics or product formation of the reaction. In some embodiments, various different components of an analytical reaction (e.g., different types of monomers) are differentially labeled to allow each labeled component to be distinguished from other labeled components during the course of the reaction. For example, incorporation of amino acid A into a polypeptide can be distinguished from incorporation of amino acid B.

In particular examples, an optically confined reaction site (also referred to as an "optical confinement"), such as a reaction site within a zero mode waveguide, is used to provide for observation of individual molecules or molecular complexes. That is, a single (one) molecule or molecular complex is optically resolvable from other such molecules or molecular complexes, e.g., those at other reactions sites. This facilitates observation of a single reaction taking place at the reaction site that involves the single molecule or molecular complex. In particular, one member of an interacting reactant pair, e.g., an enzyme, enzyme complex, receptor, cell surface protein, template, or the like, is provided immobilized within an observation region of a zero mode waveguide or waveguide array. At least one reactant component that interacts with the immobilized component is provided with a labeling group such that when that interactive reactant comes into the reaction site or observation volume, e.g., when in contact with the immobilized reactant, the label becomes detectable and/or produces a detectable signal. In certain embodiments, processive enzymatic reactions are observed in which an enzyme iteratively catalyzes an event and each iteration is separately detected. For example, an enzyme that synthesizes a polymer is observed to determine characteristics of the newly synthesized polymer (e.g., composition) and/or characteristics or the processive reactions (e.g., rate, fidelity, etc.). For reactions in which a template molecule is used by the enzyme to synthesize the polymer, characteristics of the template molecule can also be determined. Detection of the label or signal therefrom is characteristic of the particular interactive reactant and/or its interaction with the immobilized component. For example, detection of the label can allow identification of the interactive reactant and/or provide information about the characteristics of the interaction (e.g., amino acid incorporated, kinetics, etc.). Of course, other types of labeling strategies that provide means of observing one or more aspects (e.g., kinetic aspects) of a reaction of interest are also applicable to the methods of the invention, many of which are provided below and elsewhere herein, as well as in U.S. patent application Ser. No. 12/814,075, filed Jun. 11, 2010; and U.S. Ser. No. 12/635,618, filed Dec. 10, 2009, the disclosures of which are incorporated herein by reference in their entireties for all purposes.

In some embodiments, various different components of an analytical reaction (e.g., different types of aminoacyl-tRNA complexes) are differentially labeled to allow one or more labeled components to be distinguished from other labeled components during the course of the reaction. For example, incorporation of a first type of amino acid into a polypeptide chain can be distinguished from incorporation of a second type of amino acid. In some cases, a detectable signal may derive from a single label on a non-immobilized reaction component that produces a signal duration indicative of a specific interaction, e.g., as a result of binding and/or reaction with the immobilized component. For example, if a ribosome complex is immobilized at a reaction site and aa-tRNAs in the reaction mixture are tagged with detectable labels, the association of a given aa-tRNA with the ribosome brings the detectable label on that aa-tRNA into the reaction site allowing detection and subsequent identification of the amino acid being incorporated into the polypeptide chain, e.g., by yielding an increased retention time of the detectable label within the observation volume than would occur were there not an incorporation event. Such a signal may also or additionally be derived from a native biomolecule, e.g., the intrinsic fluorescence of a protein containing tryptophan, tyrosine, and/or phenylalanine.

Alternatively or additionally, interactive label components may be provided on different reaction components in the analytical reaction. For example, one label component can be provided on an immobilized reactant, while the other label group is provided on a non-immobilized component, or both are provided on either immobilized or non-immobilized reaction components. The different label components are selected such that when they are placed in sufficiently close proximity, such as during the interactive reaction between the two reactants, they produce a characteristic signal for that proximity, and consequently the signal can be used to monitor the reaction. Alternatively or additionally, interactive label components may be provided on a single immobilized or non-immobilized reaction component that undergoes an alteration that changes the orientation of the label components (e.g., alters the distance between them) in such a way as to change the signal emitted from the labeled reaction component during its participation in the reaction. For example, Förster resonant energy transfer (FRET) pairs may be employed that yield a characteristic fluorescent signal when the two labeled reaction components or two portions of a single reaction component are sufficiently close to each other, such as when a substrate is bound in the active site of an enzyme, when a receptor binds to its ligand, or when a reaction component undergoes a conformational change, including but not limited to release of a portion of the reaction component. Similarly, quenchers may also be employed to cause a characteristic loss in fluorescent signal when the quencher and a label are sufficiently close to each other, or a characteristic increase in fluorescent signal when the quencher and label are moved away from each other.

In certain preferred embodiments, protein synthesis reactions that occur through translation of messenger RNA into polypeptide chains are monitored in accordance with the invention. Such analytical reactions can be designed to determine sequence characteristics of the nascent polynucleotide chain, in particular during synthesis of the polypeptide, i.e., "sequencing-by-synthesis." Additionally or alternatively, such analytical reactions can be designed to monitor various characteristics of the reaction, e.g., rate, fidelity, processivity, error profile, residence time, time between incorporation events, etc., as well as differences in kinetics for different reaction components, e.g., different aa-tRNAs. Typically, such reactions comprise an mRNA molecule complexed with a ribosome in the presence of a set of aminoacyl-tRNAs (aa-tRNAs), elongation factors, and other components required for translation of the mRNA by the ribosome. In particularly preferred embodiments, such reactions provide real-time monitoring of amino acid incorporation into a single nascent polypeptide chain encoded by a single mRNA as it is processed by a single ribosome. Multiple reactions may be monitored simultaneously, e.g., on an array of optical confinements. Although some embodiments herein are described as involving use of an mRNA template, it will be understood that other types of RNA molecules can also serve as templates, e.g., when modified to possess certain elements required for ribosome binding and initiation. As such, the methods herein are not limited to using only mRNA templates, unless specifically indicated as such Such compositions, methods, and systems enable new scientific research on protein synthesis. For example, basic scientific research can be performed on protein synthesis at the single-molecule level, e.g., to characterize various aspects of such reactions including processivity, rate, timing of incorporation and/or translocation, fidelity, error profile, etc. In certain embodiments, data from these "polypeptide sequencing-by-synthesis" reactions are used to deduce sequence characteristics for the protein being synthesized and/or for the mRNA being processed by the ribosome. Uses of the methods, compositions, and systems provided herein for monitoring of protein synthesis reactions (also referred to as translation reactions) are further described below.

Yet another important biological reaction is post-translational modification of newly synthesized polypeptides. Such post-translational modifications typically involve various conformational changes within the polypeptide chain to form the secondary and tertiary structures of the mature protein. Further, association with additional polypeptides can result is creation of protein complexes (e.g., holoenzymes) that may be required for activity. The teachings herein can be applied to monitoring such processes in real time at the single molecule level. For example, a newly synthesized polypeptide can be immobilized on a substrate and its emission profile monitored over time. Changes to the emission profile can be indicative of conformational changes in the primary, secondary, or tertiary structure of a single polypeptide, or may indicate association with other proteins, as well. In some cases, the signals being monitored are based upon the intrinsic fluorescence of a given polypeptide based on its amino acid sequence. (See, e.g., Topics in Fluorescence Spectroscopy, Vol. 6, Chapter: Intrinsic Fluorescence of Proteins, Springer US 2001; and Yanushevich, Y. et al. (2003) "A Natural Fluorescent Protein That Changes Its Fluorescence Color During Maturation," Russian J. of Bioorganic Chem. 29(4): 325-329; both of which are incorporated herein by reference in their entireties for all purposes.) Alternatively or additionally, signal may be emitted from nonnatural amino acids incorporated into the polypeptide. (See, e.g., Shishido, M. (2006) "Basics and applications of fluorescence labeling of proteins by the introduction of nonnatural amino acids," Prot., Nuc. Ac., and Enzyme 51(5): 399-407, incorporated herein by reference in its entirety for all purposes.) Labels on polypeptides may undergo energy transfer, either between intrinsic or extrinsic labels, or a combination thereof, and such energy transfer could be indicative of distal portions of a polypeptide being brought together during the post-translational modification process. Further, changing reaction conditions and/or addition of various agents can be performed to test the affect of each on the post-translational modification process. Signal data collected can be analyzed for various purposes, including but not limited to identification of the protein, characterization of the higher order structures of the protein (or protein complex comprising the protein), or gaining a better understanding of the process of modifying the polypeptide to form a functional protein. In some embodiments, the agents comprise a detectable label so that their proximity to or association with the post-translational modification process can be monitored.

In further aspects of the invention, the methods and systems provided herein can be used for testing the effects of various agents on a biological reaction such as a protein synthesis reaction and/or post-translational modifications. In some embodiments, the agents comprise a detectable label so that their proximity to or association with the biological reaction can be monitored. The methods include new pharmaceutical drug screening strategies for a given model system, e.g., that monitors the effect(s) of drugs, drug candidates, and other agents on protein synthesis and/or post-translational modifications. The methods can thereby function as a drug discovery tool, for example, for protein synthesis/post-translational modification-related diseases or for new antibiotics. In certain preferred embodiments, ongoing biological reactions are monitored in real-time at a single-molecule (or single-molecular complex) level for various kinds of effects, including but not limited to rate, processivity, fidelity, residence time, time between biochemical events (e.g., pausing), differences between biochemical events (e.g., substrate preference), conformational changes, and various other aspects specific for a particular biological reaction of interest.

II. Protein Synthesis Reactions

In certain preferred embodiments, the present invention provides methods for monitoring single molecules (or molecular complexes) in analytical reactions in which protein synthesis is occurring in real-time, e.g., ribosome-mediated protein synthesis. Such analytical reactions preferably comprise a molecular complex that can be immobilized in an optical confinement and one or more reaction components (immobilized and/or non-immobilized) that can be detectably labeled and monitored in real-time. Reactions in which a distinct detectable signal is emitted in association with a specific biochemical reaction event (e.g., amino acid incorporation, binding, translocation, dissociation, etc.) are particularly suitable.

In certain aspects, the present invention provides compositions, methods, and systems for single-molecule, real-time analysis of polypeptide synthesis carried out by a ribosome in an individually optically resolvable configuration, e.g., immobilized on a substrate and/or in an optical confinement, thereby allowing individual monitoring of the ribosome during synthesis of a nascent polypeptide chain. As such, a preferred feature of the invention is isolation of a single ribosome complex to allow detection of signals from only that complex or labeled reaction components in its immediate vicinity, e.g., at a reaction site. Providing such individually resolvable configurations can be accomplished through a number of mechanisms and typically involves immobilization of at least one component of a ribosome complex at a reaction site. Various methods for providing an isolated molecular complex are provided in the section entitled "Optical Confinements" herein.

Various methods for in vitro translation are known and readily available to those of ordinary skill in the art. For example, see U.S. Patent Publication Nos. 2004/0023256, and 2006/0228708; U.S. Pat. No. 7,297,532; U.S. Ser. No. 61/351,919; International Patent Publication Nos. WO 2003/0064608, WO 2003/0064604, WO 2009/002866 and WO 2006/0125012; Sytnik, A., et al. (1999) "Peptidyl Transferase Center Activity Observed in Single Ribosomes," J. Mol. Biol. 285: 49-54; Karlsson, M., et al. (1999) "Initiation of *Escherichia coli* ribosomes on matrix coupled mRNAs studied by optical biosensor technique," Biochimie 81: 995-1002; Vanzi, F., et al. (2003) "Protein synthesis by single ribosomes," RNA 9: 1174-1179; Blanchard, S., et al. (2004) "tRNA dynamics in the ribosome during translation," PNAS 101(35):12893-12898); Vanzi, F., et al. (2005) "Mechanical Studies of Single Ribosome/mRNA Complexes," Biophysical Journal 89: 1909-1919; Uemura, S., et al. (2008) "Single-molecule imaging of full protein synthesis by immobilized ribosomes," Nucleic Ac. Res. 36 (12): e70; Kawahashi, et al. (2003) Proteomics 3:1236-1243; and He, et al. (2001) Nuc. Ac. Res. 29:E73, all of which are incorporated herein by reference in their entireties for all purposes. Further, the methods, compositions, and systems provided herein may be used in combination with one or more kits for in vitro translation commercially available from, e.g., Applied Biosystems/Ambion (Austin, Tex.), Roche Applied Science (Indianapolis, Ind.), Novagen/EMD Chemicals, Inc. (Gibbstown, N.J.), GE Heathcare (Buckinghamshire, UK), Qiagen (Hilden, Germany), Promega (Madison, Wis.), and Ambergen (Watertown, Mass.).

In certain embodiments, an in vitro translation system is constructed from purified components, e.g., ribosome subunits, mRNA templates, aa-tRNA complexes, elongation factors, nucleotide cofactors, buffers, salts, etc. In other embodiments, cell extracts or fractions thereof are used to construct an in vitro translation system. In certain embodiments, using cell extracts rather than purified components is useful for analysis of translation (e.g., dynamics and/or regulation) in an environment more similar to that found within the cell. Optionally, a cell extract can be treated to remove unwanted components or to isolate them for further manipulation (e.g., labeling, immobilization, and the like) prior to adding them back to the reaction mixture. In particular, a reticulocyte lysate or wheat germ extract can be size fractionated to remove native ribosomes, which are subsequently attached to a substrate at a reaction site (e.g., in an optical confinement). The remainder (or a fraction thereof) of the lysate or extract can be added to the substrate, and protein synthesis from one or more mRNA templates can be monitored in real-time, with each ribosome being independently observable. The lysate or extract can also be treated prior to addition to the substrate, e.g., by labeling one or more components or by addition or removal of certain components. For example, native, unlabeled aa-tRNAs may be removed (or the cell culture may contain mutations making tRNAs absent under certain conditions) and replaced with aa-tRNAs linked to detectable labels that identify their resident amino acids upon incorporation into the nascent polypeptide chain, as described elsewhere herein. In further embodiments, a combination of purified components and cell extracts or fractions thereof are used to construct an in vitro translation system.

The biochemical process of translation is the method by which a cell synthesizes a polypeptide based on the sequence of an mRNA molecule. In brief, a ribosome "reads" the mRNA template and sequentially incorporates amino acids into a nascent polypeptide chain to synthesize a protein encoded by the mRNA template. In certain aspects of the instant invention, an optical system (comprising, for example, a camera) is used to detect a signal (e.g., from an aa-tRNA, ribosome, nucleotide cofactor, and/or elongation factor) as the ribosome incorporates an amino acid from the aa-tRNA into the nascent polypeptide chain. Depending on the labeling strategy, incorporation of one or more types of amino acids can be detected and distinguished from incorporation of other types of amino acids, thereby providing sequence characteristics for all or a part of the sequence of the polypeptide chain as it is being synthesized. In some preferred embodiments, these methods are performed in a highly parallel manner with thousands of ribosome complexes on single substrate, e.g., in an array of optical confinements, which are optically resolvable from one another. In certain preferred embodiments, these methods are performed in a processive manner, e.g., detecting multiple incorporation events in real time without intervening manipulations to the reaction system, such as buffer exchange, washing, etc. A processive reaction means that multiple events occur one after the other without external manipulation, e.g., washing, buffer exchange, temperature changes, addition of agents, etc. For example, an processive enzyme reaction is one in which an enzyme or enzyme complex catalyzes multiple biochemical events one after the other without intervening external manipulation, similar to the natural activity of the enzyme or enzyme complex in vivo. In some preferred embodiments, a processive protein synthesis (or translation) reaction is one in which a ribosome catalyzes multiple amino acid incorporation events in the absence of any substantial changes to the reaction mixture (aside from those catalyzed by the enzyme).

In certain aspects, a protein synthesis reaction to be monitored as described herein is further coupled to one or more related biochemical systems. For example, a protein synthesis reaction can be coupled to transcription of a DNA template that produces an mRNA template to be subjected to translation. For example, an RNA polymerase and a DNA template encoding an mRNA template may be included in the reaction mixture. Conditions are provided to promote transcription of the DNA template to produce the mRNA template, which is allowed to bind to an immobilized ribosome complex and undergo translation to produce a polypeptide chain encoded by the original DNA template. In other embodiments, the RNA polymerase may be immobilized at a reaction site, generating an mRNA template that extends into the surrounding reaction mixture. A ribosome is allowed to bind the mRNA template and commence translation prior to release of the mRNA from the RNA polymerase. In preferred embodiments, the DNA template is a circular template that is not released from the RNA polymerase but continues to be transcribed in a "rolling circle" fashion to produce a long mRNA concatemer by "rolling circle translation." A "dynamic stasis" is established as the ribosome is essentially tethered to the reaction site by its association with the mRNA product of the ongoing translation reaction, and this keeps the ribosome in a relatively stable location within the reaction site to allow amino acid incorporation events to be detected in real time. Various reaction conditions and components that can be modified to establish the dynamic stasis between the transcriptional and translational machinery are known in the art and include, e.g., salt concentration, cofactor concentration, ligand concentration, enzyme variants, and the like. Further, for mRNAs that require post-transcriptional modification prior to translation, post-transcriptional modification enzymes and cofactors (e.g., spliceosomes, etc.) can also be included in the reaction mixture. In yet further embodiments, both the ribosome and RNA polymerase may be immobilized to facilitate transfer of the mRNA template synthesized at the RNA polymerase to the ribosome for translation.

FIG. 1 provides an illustrative example of certain embodiments of various aspects of a protein synthesis reaction (100) to be monitored and analyzed by the methods and systems of the invention. In certain embodiments of the present invention, a ribosome complex (105) comprises an mRNA template molecule (110) associated with a ribosome (115). In certain preferred embodiments, the ribosome complex (105) is immobilized upon a substrate (not shown), e.g., within an optical confinement, as further described herein. The ribosome complex (105) is bathed in a solution of aminoacyl-tRNAs (aa-tRNAs) (120) and any additional reaction components required for protein synthesis, e.g., elongation factors, GTP, etc. Bound to the P (peptidyl) site (125) of the ribosome (115) is a polypeptidyl-tRNA (130) comprising an anticodon (135) bound to a complementary codon ("first codon") (140) in the mRNA template (110). The A (aminoacyl) site (145) is positioned at a second codon (150) immediately adjacent to and 3' of the first codon (140), and is ready to receive an aa-tRNA (155) with an anticodon (160) complementary to the second codon (150).

Each addition of an amino acid into the polypeptide chain (termed "elongation") comprises the following steps: a) binding of a complementary aa-tRNA to the A site; b) formation of a peptide bond between the amino acid nearest the tRNA portion of the polypeptidyl-tRNA and the amino acid on the aa-tRNA in the A site, thereby transferring the polypeptide chain to the aa-tRNA in the A site (thereby creating a polypeptidyl-tRNA at the A site); and c) translocation of the ribosome one codon toward the 3' end of the mRNA template. This translocation moves the P site to the second codon (at which the newly formed polypeptidyl-tRNA is bound) and moves the A site to the codon immediately 3' of the second codon to await arrival of an aa-tRNA having a complementary anticodon. The E (exit) site of the ribosome moves to associate with the deacylated tRNA, which is thereafter released from the ribosome complex.

In certain embodiments, various components of the reaction mixture that need not be proximal to the ribosome complex for polypeptide synthesis can be immobilized outside of a reaction site, e.g. on beads or other substrates. For example, the process of translation involves a large number of protein factors, some of which associate with other components of the reaction mixture that are linked to detectable labels. In order to prevent such protein factors associated with a labeled reaction component from nonspecifically localizing at a reaction site and, thereby, causing detection of signal that is not associated with an amino acid incorporation event, such protein factors can be immobilized in such a way that they are excluded from the reaction site. In certain specific embodiments, aa-tRNA synthetases are immobilized to beads that are too large to allow the aa-tRNA synthetases access to the optical confinement, thereby preventing the synthetases from carrying a labeled tRNA into an optical confinement and reducing nonspecific signal from the reaction site. In some embodiments, a single substrate can hold a single protein factor, and in other embodiments multiple protein factors may be held on the same substrate. In some embodiments, the substrate could be removed from the reaction mixture before adding the reaction mixture to the optical confinement(s), e.g., aa-tRNA synthetases could be removed after they have charged tRNAs to generate aa-tRNAs. For example, magnetic beads bearing the protein factor(s) could be removed using a magnetic field, or charge-bearing beads could be removed using an electromagnetic field. Alternatively, they could be retained in the reaction mixture during translation to re-charge deacylated tRNA molecules that have been released by the ribosome.

Various labeling strategies can be implemented for real-time single-molecule analysis of a protein synthesis reaction. In preferred embodiments, at least one or more of the aa-tRNAs are labeled, and the label may be a single component label on either the amino acid or tRNA component, or may be a multi-component label as described further below. The label carried by a given aa-tRNA is specific for a particular type of aa-tRNA or a group of aa-tRNAs. In a first example, a first label "A" may be associated with only Phe-tRNA in the reaction mixture. In this example, detection of label A during protein synthesis (e.g., wherein the detected signal has characteristics consistent with an incorporation event) is indicative of incorporation of a single specific amino acid, phenylalanine, into the nascent polypeptide strand. In another example, a second label "B" may be associated only with a specific group of aa-tRNAs, e.g., Leu-tRNA and Met-tRNA. In this example, a signal from label B consistent with an incorporation event is indicative of incorporation of leucine or methionine into the polypeptide strand. In a further example, a reaction mixture can include A-labeled Phe-tRNA and B-labeled Leu-tRNA and Met-tRNA. Detection of a particular pattern of A labels and B labels provides sequence data for the nascent polypeptide chain. As such, detection of labels on the aa-tRNAs during polypeptide synthesis provides sequence characteristics of the nascent polypeptide strand in real-time. Additional detection strategies useful with the present invention are described in greater detail elsewhere herein including, for example, using the natural signal generation (e.g., intrinsic fluorescence) displayed by some biomolecules.

Further, the RNA templates to be subjected to translation may be from any source of interest to the investigator, e.g., samples from one or more organisms (e.g., blood, mucus, lymph, tissue, cells, etc.) or environmental samples (water, ice, soil, air, etc.). For example, the methods can involve transcriptional analysis of collections of RNAs from environmental samples. Their sequences may be known or unknown (e.g., randomly generated synthetic templates, degenerate RNA sequences, etc.). In some preferred embodiments, RNA molecules that are not naturally occurring mRNA molecules (e.g., a fragment of a retroviral genome, tRNA, rRNA, etc.) are modified to incorporate one or more ribosome recognition sequence (e.g., a ribosomal binding site (RBS), a Shine-Delgarno sequence, a Kozak consensus sequence, an internal ribosome entry site (IRES), a 5' cap sequence, etc.). For example, an adaptor bearing a sequence required for translation can be ligated to an RNA molecule to facilitate translation of the RNA molecule as described herein.

The RNA templates may be from a single source or multiple sources. In certain preferred embodiments, a plurality of mRNA templates are analyzed simultaneously, e.g. in an array of optical confinements. In certain embodiments, the plurality of mRNAs is used to detect rare mRNA variants against a background of common mRNA transcripts. Typically, bulk analyses comprising analysis of a pooled mixture are unable to detect rare variants since the characteristics of the majority of species in a pooled mixture tend to "swamp out" the characteristics of rare variants. Since each molecule of mRNA in the mixture is individually and independently analyzed during the polypeptide sequencing-by-synthesis reactions described herein, rare variants can be identified. Pools of mRNA templates can also be used to individually (i.e., as single molecules) test their constituent mRNA templates for differences in protein synthesis characteristics, including but not limited to rate, efficiency, error profile, pausing, etc. These assays can be performed under a variety of conditions to determine how alterations in reaction conditions (e.g., addition of agents, metal ion concentration changes, different labeled aa-tRNAs, etc.) impact the translation of the different mRNAs in the pool.

In some such embodiments, individual templates in the pool of templates are immobilized at optically resolvable reaction sites and exposed to ribosomes in solution under conditions that support binding and subsequent translation of the templates. Such embodiments allow repeated sequencing of the same templates at the same reaction sites, either by the same or a different ribosome. For example, ribosomes having different variations, in amino acid or nucleic acid sequences, can be separately exposed to the immobilized templates to test the different characteristics of the resulting protein synthesis reactions. Alternatively, the different ribosome variants can be introduced at the same time, e.g., where each different variant carries a tag that identifies its presence at a given reaction site. In other embodiments, ribosomes are immobilized and the pool of templates introduced and allowed to bind to the immobilized ribosomes such that a single ribosome at a single reaction site binds only a single template molecule.

In some embodiments, the plurality of mRNAs is from the same tissue in an individual, for example to study the types of mRNAs present in that tissue, which would provide information about the types of proteins being synthesized in the tissue at the time of collection. For example, presenting the entire transcriptome on an array or a series of arrays provides an opportunity to study translation (e.g., dynamics and/or regulation) on the whole transcriptome level, perhaps simultaneously. Alternatively, the plurality can be from the same tissue in multiple individuals to provide a more general analysis of mRNA and protein synthesis in a population of individuals. The population may be closely related individuals, or may be individuals from different families or even different species, depending on the particular aims of the study. Comparison of protein synthesis from mRNA templates isolated from different sources can provide valuable information regarding the underlying differences in the proteomes for those sources. For example, comparison of polypeptides synthesized from mRNA isolated from a tumor and polypeptides synthesized from mRNA from healthy tissue provides information on mRNA and protein synthesis in those tissues, and this information can be used to better understand the biology of the tumor tissue and to target drugs to aspects of the tumor tissue that differ from the healthy tissue. Further, understanding these differences can also facilitate the development of diagnostic tools to identify tissues that are cancerous or precancerous, for example by screening for mRNA or protein synthesis profiles specific to cancerous or precancerous tissues.

In some embodiments, the mRNA template is a linear template, e.g., as normally synthesized and translated within a cell. Optionally, such an mRNA template may be modified prior to translation, e.g., using common molecular biology techniques, to encode a desired feature into the nascent polypeptide. For example, it may be engineered to incorporate features useful for the translation reaction (e.g., circularization, introduction of sequence or registration tags, etc.), or sequences that, once translated, facilitate post-translational manipulations of the nascent protein such as labeling/detection, folding, maturation, immobilization, complex formation, etc. For example, the mRNA can be modified to encode a tag sequence that is translated into the nascent polypeptide and subsequently used to capture the nascent polypeptide, e.g., at or near the reaction site, for further analysis. Alternatively or additionally, a modification to the mRNA template may provide a signaling event during the translation reaction. For example, inclusion of a secondary structure or modified base can be incorporated to change certain characteristics of a translation reaction, e.g., changing kinetics by introducing a pause at a position of interest on the template. Detection of the kinetic alteration is indicative that the ribosome has reached the position of interest, e.g., at a given time during the reaction, and the behavior of the ribosome at the modification can be further studied by changing reaction conditions, including but not limited to temperature, pH, and addition of agents such as drugs, binding agents, antibodies, and the like.

In certain embodiments, the mRNA template is circularized to facilitate repeated translation of the same mRNA template to produce a long, repeating polypeptide chain by "rolling circle translation." Methods for circularizing RNA molecules are known in the art and generally involve an RNA ligase (e.g., T4 RNA ligase) and are provided, e.g., in Chen, C. et al. (1995) Science 268: 415-417; and Wang, L. et al. (1998) Nuc. Acids Res. 26(10): 2502-2504, and related methods for determining a sequence for a DNA template are provided, e.g., in U.S. Ser. No. 61/072,160, 61/099,696, 12/383, 855, and 12/413,258, all of which are incorporated herein by reference in their entireties for all purposes. Such embodiments benefit from having the ribosome immobilized and the circular template free in solution. As noted above, the mRNA can be further altered to incorporate codons after the coding region that are translated into a "polypeptide sequence tag" that can be used during analysis of the polypeptide sequence, e.g., to "mark" the portions of the polypeptide that are in between the portions encoded by the mRNA prior to alteration, e.g., the protein coding portions. The mRNA can also be altered to ensure that the frame is maintained in each iterative round of translation, e.g., one or two nucleotides may be added to keep the translation "in frame" for repeated "rounds" of translation. Alternatively, out-of-frame translation (e.g., translation in each of the three frames) can be used to further confirm the sequence of the "in frame" polypeptide, or can be used to derive the sequence of the original mRNA template by using knowledge of the genetic code and how each round of translation is frameshifted relative to those immediately preceding and following it. Such methods provide a "circular consensus translation" of the mRNA template, providing redundant sequence information that is useful for validating the polypeptide sequence of interest. By repeated sequencing of the same molecule, multiple amino acid sequence "reads" are generated from the same mRNA, and these reads can be analyzed in various ways, including but not limited to comparison of the multiple reads generated to one another and analysis of reaction characteristics (e.g., polypeptide sequence generated, rate, error profile, time between incorporation events, and other kinetic metrics) for each read. Analytical results are used to determine a consensus sequence for the encoded polypeptide, and can also be used to identify various aspects of the template, as well, such as template structure, described further herein.

Further, such embodiments optionally comprise modified reaction components that allow bypass of a termination (stop) codon in the mRNA template, thereby allowing continuous repeated translation of the template. For example, a ribosome can be used that contains an alteration that suppresses termination at a stop codon (e.g., because the ribosome is unable to recognize the stop codons in the template), tRNA mutants can be used that comprise an anticodon that is complementary to a stop codon and carry an amino acid residue (e.g., glycine) to be incorporated into the nascent polypeptide when the stop codon is encountered, and/or termination factors can be mutated or removed from the system to prevent translation termination. For additional general information about the ribosome, transcription termination, and suppression thereof, see Bruce Stillman, "The Ribosome: proceedings of 2001 symposium," Cold Spring Harbor Laboratory Press 2001; and for further information on specific transcription termination suppressors, see, e.g., Jemiolo, D. et al. (1995) Proc. Natl. Acad. Sci. U.S.A. 92(26): 12309-12313; and Carnes, J., et al. (2000) RNA 6(10): 1468-1479. In preferred embodiments, the method of transcription termination suppression used prevents dissociation of the ribosome and allows transcription to continue through a stop codon in the mRNA, thereby generating a long "polypeptide concatamer" molecule comprising multiple copies of the polypeptide encoded by the mRNA.

Another method for generating redundant polypeptide sequence information involves providing an mRNA template that is a concatemer, i.e., contains multiple tandem (though not necessarily immediately adjacent) copies of an mRNA of interest. One way to generate such an mRNA concatemer template is through rolling circle transcription (described briefly above), in which stop (termination) signals are removed from a circular DNA template (e.g., comprising a gene of interest), which is subjected to transcription by a processive RNA polymerase to generate a long, repetitive mRNA template for translational analysis. The DNA template can be further modified to encode nucleotide sequence tags that are transcribed into the mRNA and subsequently translated into polypeptide sequence tags in the polypeptide. These polypeptide sequence tags can be used for orientation purposes in subsequent analysis, e.g., to "mark" the polypeptide sequence between the protein sequences encoded by the original DNA sequence from which the mRNA was transcribed.

In embodiments in which a linear mRNA template is immobilized on the substrate, multiple reads of the nascent polypeptide can be generated by repeatedly subjecting the mRNA to translation and monitoring incorporation of amino acids into each nascent polypeptide chain generated, as described elsewhere herein. Preferably, kinetic characteristics of the translation are also monitored and analyzed. In certain embodiments, the characteristics of a translation reaction are used to study modifications in the template, rates of incorporation and/or translocation, and error profile for the reaction. For example, regions or locations at which the ribosome tends to pause on the template, as well as the amino acids being incorporated at such regions or locations, are studied to determine the underlying causes of such alterations in ribosome function. Reaction conditions can be changed in order to observe translation of the same RNA molecule in the presence of a variety of different environmental factors. In certain embodiments, templates are used that contain a region of codons complementary to unlabeled aa-tRNA complexes to produce a "dark" period during which no signal is detected from the reaction site, the dark period flanked by periods during which polypeptide sequence data is being generated. The number of codons in the region corresponding to the dark period is known, and the time required for the ribosome to traverse this region is determined to provide a speed of the ribosome through the region. In some embodiments, both the mRNA and ribosome can be immobilized to facilitate reloading of the ribosome onto the mRNA after each round of translation. Certain preferred methods for immobilization of various reaction components are further described herein in "Optical Confinements."

For protein synthesis reactions in which an mRNA template is immobilized, certain preferred embodiments are designed to prevent multiple ribosomes from binding to a single immobilized mRNA. For example, after a solution comprising the ribosomes is introduced to the immobilized mRNA templates under conditions that promote ribosome-mRNA association, the substrate can be washed to remove any unbound ribosomes that could potentially bind to the translation initiation codon once the initially bound ribosome has translocated beyond it on the mRNA template. Alternatively or additionally, oligonucleotides complementary to the mRNA template at the initiation codon could be added to the reaction mixture after binding of the ribosomes to prevent subsequent binding by a second ribosome. In some such embodiments, repeated translation of bound mRNA templates that involves dissociation of the ribosome would require removal of the oligonucleotides from the initiation codon to allow reassociation of the ribosome complex to the mRNA template. Alternatively or additionally, oligonucleotides containing an initiation codon and a subsequent codon at which the ribosomes will stall could be added to the reaction mixture to bind free ribosomes and prevent them from binding to the bound template mRNA molecules.

The observation of protein synthesis by single ribosomes, e.g., by detection of aa-tRNAs binding to the ribosome, allows detailed study of the dynamics of the process, both in the absence and presence of agents that can alter those dynamics. For example, various aspects and characteristics related to the initation, termination, rate, time between incorporation events, time between initiation of incorporation events, time between binding of an aa-tRNA and translocation, alterations in behavior at different times during the reaction, fidelity, error profile (e.g., types and frequency of errors in incorporation, such as incorporating an amino acid not encoded by an RNA template), processivity, and other kinetic aspects can be directly measured for a single ribosome complex on a single known or unknown template molecule. The affects of various agents on these aspects are therefore readily measurable. As used herein, the term "agents" includes not only additives to the reaction mixture, but also changes in conditions (e.g., temperature, pH, etc.) and alterations to the reactants (e.g., substitutions, mutations, changes in concentrations, etc.). Agents that are additives include, but are not limited to small molecules, drugs, drug candidates, miRNAs, siRNAs, piRNAs, CRISPR RNAs, tmRNAs, antisense RNAs, other nucleic acids that bind to the template, template-binding proteins, modification-binding agents (e.g., agents that specifically bind to modifications in the template, such as abasic sites, damaged bases, secondary structure, tertiary structure, etc.), divalent cations, monovalent cations, metal ions, acids, bases, antibiotics, antibodies, toxins, etc. In some embodiments, the agents comprise a detectable label so that their proximity to or association with the ribosome complex can be monitored.

In some embodiments, an agent that is a mutation or modification to an mRNA template in a 5' cap region, ribosome binding site, riboswitch element, initiation site (or other regulatory element), 3'UTR, translated portion, or 5'UTR, and can include modified bases, secondary or tertiary structure modifications (e.g., introduction of a hairpin, tetraloop, pseudoknot, stern-loop, etc.), abasic sites, and the like. Such a mutation can be introduced and translation of the template monitored to study various characteristics of the reaction, including translational regulation, efficiency, kinetics (e.g., related to initiation, elongation, and termination dynamics), etc., as it relates to these regions of the template. In related embodiments, the methods can be used to screen different mRNAs, e.g., alternate splice products or mRNAs with mutations in regions other than the UTRs, to determine their relative translation efficiencies, regulation, kinetics, etc.

Although rRNAs and tRNAs are typically extensively modified in the cell, snRNAs and mRNAs can also be the target of base modification (see, e.g., Xie, et al. (2007) Nuc. Ac. Res. 35 (Database issue):D183-7; and Omer, et al. (2003) Molecular Microbiology 48(3):617-29, the disclosures of which are incorporated herein by reference in their entireties for all purposes). In some embodiments, the characteristics of translation reactions are indicative of modifications within an RNA template, whether naturally occurring or engineered. For example, a characteristic change in the kinetics of a ribosome complex can be attributed to an encounter with or processing of a modification (e.g., modified base, abasic site, secondary or tertiary structure, etc.) within a template molecule. As such, the methods herein are useful for detection of modifications within an RNA template. Modified RNA bases include damaged bases (e.g., induced by radiation or chemical exposure), pseudouridine, hypoxanthine (e.g., in inosine), ribothymidine, nucleosides with 2'-O-methylribose, N6-methyladenine, N-2-methylguanosine, 7-methylguanosine, N-4-methylcytosine, 5-methylcytosine, etc. There are nearly 100 naturally occurring modified nucleosides described in Söll, et al. (1995) TRNA: Structure, biosynthesis, and function, ASM Press pp. 165, ISBN 155581073X; and Kiss, T. (2001) EMBO J. 20:3617-22, the disclosures of which are incorporated herein by reference in their entireties for all purposes. Further, other types of modified bases, nucleic acid modifications, and method of detection thereof are described in and U.S. Ser. No. 12/635,618, filed Dec. 10, 2009, the disclosure of which is incorporated herein by reference in its entirety for all purposes. Translation reactions using templates comprising such modifications are useful for determining the effects of such modifications on translational dynamics, including but not limited to tRNA usage, incorporation kinetics, translocation kinetics, frameshifting, read-through of stop codons and other codons. Further, reaction conditions can be altered, e.g., by changing buffer conditions, addition of one or more agents, temperature, etc., to examine the effects on the translation reactions comprising the modified templates. For example, metal ions (e.g., $Mg^{2+}$) affect secondary & tertiary structure stability, so one can alter the type or concentration of metal ions in a translation reaction comprising a template having a particular kind of secondary or tertiary structure. Such methods are useful for further revealing the relationship between template modifications and environment during translation, and how these factors influence translational dynamics at the single-molecule level.

In certain embodiments, the nascent polypeptide is immobilized at the reaction site by incorporation of tags into the polypeptide, e.g., by misaminoacylated tRNAs. The tags preferably bind to a reaction component immobilized at the reaction site, so interaction between the tag and the immobilized reaction component effectively immobilizes the nascent polypeptide. In certain embodiments, the interaction is reversible to allow release of the nascent polypeptide. This and other methods of generating an array of polypeptides are known in the art, e.g., in Lim, et al. (2008) Analytical Biochemistry 383:103-115; Zhu, et al. (2001) Curr. Opin. Chem. Biol. 5:40-45; Lopez, et al. (2003) J. Chromatogr. B 787:19-27; Kawahashi, et al. (2003) Proteomics 3:1236-1243; He, et al. (2001) Nuc. Ac. Res. 29:E73; and Melton, et al. (2004) Nature 429:101-107, the disclosures of all of which are incorporated herein by reference in their entireties for all purposes.

In certain aspects, a protein synthesis reaction to be monitored as described herein is further coupled to a post-transcriptional modification system that modifies the nascent polypeptide chain, e.g., to produce a mature protein, which can be further analyzed by standard biochemical methods. For example, various enzymes involved in posttranslational modification of a nascent polypeptide chain can be included in a reaction mixture, including but not limited to kinases, protein disulfide isomerase (PDT), chaperone proteins (e.g., BiP, hsp60), signal peptidases, oligosaccharyl transferases, and the like.

III. Detection Strategies

The present invention provides various methods for detection of components of a protein synthesis reaction, in particular detection of incorporation of amino acids into a polypeptide chain by a ribosome. In certain preferred embodiments, the polypeptide chain being synthesized is a "natural" polypeptide containing no labeling or quenching groups, which could otherwise hamper synthesis by introducing steric and/or electrostatic hindrances into the resulting polypeptide. In certain preferred embodiments, detection occurs in real-time, e.g., each incorporation is detected independently during synthesis (as opposed to bulk detection methods, e.g., in which a plurality of identical types of incorporation events are simultaneously detected as a single event). In certain preferred embodiments, detection occurs at the single-molecule level, e.g., the sequence of amino acids incorporated into a single polypeptide is detected independently of any other polypeptide. In certain preferred embodiments, detection occurs at the single-molecule level in real time. In certain preferred embodiments, incorporations occurring in multiple protein synthesis reactions are detected independently and simultaneously, e.g., in an array of reaction sites that are preferably within optical confinements.

In certain aspects, one or more components of a protein synthesis reaction comprise detectable labels, e.g., that serve to signal a binding, incorporation, translocation, or dissociation event. Such labels can be detectable moieties known in the art including, but are not limited to, chromophores (e.g., fluorophores and other dyes), quantum dots, non-fluorescent tags (e.g., surface enhanced Raman scattering (SERS) particles), scattering metallic nanoparticles (e.g., gold or silver), combinations of chromophores (e.g., FRET labels on a single or multiple components), intrinsic fluorescence, and the like. A variety of detectable labels have been developed in the art, including those described in U.S. Pat. Nos. 6,399,335, 5,866, 366, 7,476,503, and 4,981,977; U.S. Patent Pub, No. 2003/0124576; U.S. Ser. No. 61/164,567; WO 01/16375; Mujumdar, et at Bioconjugate Chem. 4(2)105-111, 1993; Ernst, et al, Cytometry 10:3-10, 1989; Mujumdar, et al, Cytometry 10:1119, 1989; Southwick, et al, Cytometry 11:418-430, 1990; Hung, et al, Anal. Biochem. 243(1):15-27, 1996; Nucleic Acids Res. 20(11):2803-2812, 1992; and Mujumdar, et al, Bioconjugate Chem. 7:356-362, 1996, all of which are incorporated herein by reference in their entireties for all purposes. Many such labeling groups are commercially available, e.g., from the Amersham Biosciences division of GE Healthcare, and Molecular Probes/Invitrogen Inc. (Carlsbad, Calif.)., and are described in 'The Handbook—A Guide to Fluorescent Probes and Labeling Technologies, Tenth Edition' (2005) (available from Invitrogen, Inc./Molecular Probes and incorporated herein in its entirety for all purposes).

In certain embodiments, detectable labels undergo Förster resonance energy transfer (FRET), and such labels are termed "FRET labels" herein. FRET labels typically comprise at least two chromophores that engage in FRET such that at least a portion of the energy absorbed by at least one "donor chromophore" is transferred to at least one "acceptor chromophore," which emits at least a portion of the transferred energy as a detectable signal contributing to an emission spectrum. In some embodiments, the donor and acceptor reside on a single molecule that undergoes a conformational change that affects the emitted signal, e.g., by varying the distance between them. Alternatively, the donor and acceptor can reside on different molecules that, during the course of a reaction (e.g., during incorporation of an amino acid), bring the chromophores near enough to each other to undergo FRET. Any of a number of fluorophore combinations can be selected for use in the present invention (see for example, Pesce et al., eds, Fluorescence Spectroscopy, Marcel Dekker, New York, 1971; White et al., Fluorescence Analysis: A practical Approach, Marcel Dekker, New York, 1970; Handbook of Fluorescent Probes and Research Chemicals, 6th Ed, Molecular Probes, Inc., Eugene, Oreg., 1996; all of which are incorporated herein by reference in their entireties for all purposes). In general, a preferred donor fluorophore is selected that has a substantial spectral overlap with the acceptor fluorophore. Additional examples of useful FRET labels include, e.g., those described in U.S. Pat. Nos. 5,654,419, 5,688,648, 5,853,992, 5,863,727, 5,945,526, 6,008,373, 6,150,107, 6,177,249, 6,335,440, 6,348,596, 6,479,303, 6,545,164, 6,849,745, 6,696,255, and 6,908,769; Published U.S. Patent Application Nos. 2002/0168641, 2003/0143594, and 2004/0076979; U.S. Ser. No. 61/164,567, filed Mar. 30, 2009; and U.S. Ser. No. 12/749,859, filed Mar. 30, 2010, the disclosures of which are incorporated herein by reference in their entireties for all puposes. Further, Förster-type resonant energy transfer can also be influenced by metal nanoparticles (see, e.g., Reil, F., et al. (2008) Nano Lett. 8(12); 4128-4133, incorporated herein by reference in its entirety for all purposes).

In certain embodiments, detectable labels are semiconductor nanocrystals such as quantum dots. Quantum dots are particularly significant for optical applications due to their theoretically high quantum yield. High-quality quantum dots are well suited for optical encoding and multiplexing applications due to their broad excitation profiles and narrow/symmetric emission spectra. Quantum dots have been found to have certain beneficial characteristics, including high brightness (owing to the high quantum yield) and high photostability, allowing real-time tracking of molecules and cells over extended periods of time (see, e.g., M. Dahan, et al. (2003) "Diffusion dynamics of glycine receptors revealed by single-quantum dot tracking," Science, vol. 302, pp. 442-445). Quantum dots are known in the art and include those described in U.S. Pat. Nos. 6,207,392, 6,114,038, 6,326,144, 7,192,785, 7,405,434, 7,460,960; Chan et al. (1998) "Quantum Dot Bioconjugates for Ultrasensitive Nonisotopic Detection" Science 281:2016-2018; Bruchez et al. (1998) Science 281:2013-2016. Quantum dots are commercially available from Invitrogen Corporation (Carlsbad, Calif.). Additional information on preparation, characteristics, and methods for using of various quantum dots can be found in the art, e.g. in Bawendi et al. (1993) J. Am. Chem. Soc. 115:8706; Dabbousi et al. (1997) J. Phys. Chem. B 101:9463; Danek et al. (1996) Chem. Mater. 8:173-179; Effros et al. (1996) Physical Review B. 54:4843-4856; Empedocles et al. (1996) Physical Review Letters 77:3873-3876; Goldman et al. (2002) J. Am. Chem. Soc, 124:6378-82; Murakoshi et al. (1998) J. Colloid Interface Sci. 203:225-228; Murray et al. (1993) J. Am. Chem. Soc. 115:8706-8714; Murray et al. (1996) Science 270: 1355-1338; Nirmal et al. (1996) Nature 383:802-804; Norris et al. (1996) Physical Review B. 53:16338-16346; Pathak et al. (2001) J. Am. Chem. Soc. 123:4103-4; Peng et al. (1997) J. Am. Chem. Soc. 119:7019-7029; Remade et al. (2000) Proc. Natl. Sci. USA 18:553-8; Rodriguez-Viejo et al. (1997) Appl. Phys. Lett. 70:2132-2134; Sacra et al. (1996) J. Chem. Phys. 103:5236-5245; and Optical Materials and Engineering News (1995) Vol. 5, No. 12, the disclosures of which are incorporated herein by reference in their entireties for all purposes.

In certain embodiments, detectable labels are surface enhanced Raman scattering (SERS) particles. Surface enhanced Raman spectroscopy or surface enhanced Raman scattering, often abbreviated SERS, is a technique that involves the enhancement of Raman scattering by molecules absorbed on a metal surface. The enhancement factor can be as much as $10^{14}$-$10^{15}$, which allows the technique to be sensitive enough to detect single molecules. The use of SERS particles may be particularly beneficial in certain embodiments since at least ten or more types are commercially available (e.g., from Nanopartz (Salt Lake City, Utah), Oxonica (Mountain View, Calif.), and Nanospectra Biosciences (Houston, Tex.)) that have unique spectral emission signatures, thereby allowing great flexibility in differential labeling of multiple components of a reaction mixture. For example, using ten optically distinguishable SERS particles to label ten different aa-tRNAs allows the sequence of the incorporation of ten different amino acids to be detected and, potentially, the polypeptide identified based on homology to known polypeptide sequences. Further, using combinations of ten different SERS particles on single aa-tRNAs further potentially allows all aa-tRNAs to be differentially labeled, thereby allowing detection of each amino acid incorporated into the polypeptide chain. Additional information on preparation, characteristics, and methods for using of various SERS particles can be found in the art, e.g. in U.S. Pat. Nos. 7,515,269, 7,511,808, and 7,485,471; PCT Publication Nos. WO/2003/095973 and WO/2008/001978; Nie, S. and Emory, S. R. (1997) Science 275 (5303): 1102-1106; Petrov, D. V. (2007) J. Opt. A: Pure Appl. Opt. 9 S139-S156; Culha, M. et al. (2003) Expert Rev Mol Diagn 3(5): 669-75; Culha, M. et al. (2003) Anal Chem 75(22): 6196-201; and Boncheva, M., et al. (1999) Langmuir 15: 4317, all of which are incorporated herein by reference in their entireties for all purposes.

In further embodiments, combinations of different kinds of labeling groups can be used on different reaction components in a single analytical reaction mixture. For example, chromophore-based labels (e.g., fluorescent dyes) can be linked to a subset of aa-tRNAs while SERS labels or quantum dots are linked to a different subset of aa-tRNAs. Further, multi-component labels may comprise a combination of different types of labeling groups; for example, a FRET pair can comprise a quantum dot donor and a fluorophore acceptor. The combinations of types of labels used and which reaction components are labeled need only ensure optical distinguishability between reaction components in order to provide the protein synthesis reaction characteristic(s) (e.g., sequence of amino acids incorporated or kinetic characteristics such as rate, processivity, fidelity, etc.) desired by the investigator. In further embodiments, detectable labels are composed of a mixture of elemental labels (e.g., three different Quantum dots), and by mixing the ratios of the elemental labels one can generate hundreds of distinct "colors" in a manner similar to how many colors are produced on a television. See, e.g., Han, et al. (2001) Nat. Biotechnol. 19:631-635; and Xu, et al. (2007) Anal. Chem. 79(10):3716-3723, both of which are incorporated herein by reference in their entireties for all purposes. Both describe preparation and use of multicolor semiconductor quantum dot-encoded polymeric microspheres having precisely controlled ratios of their constituent quantum dots and which can function as chemical sensors.

Detectable labels for use with the compositions, methods, and systems described herein can be attached to various and multiple components of a protein synthesis reaction mixture. For example, one or more may be attached to an aa-tRNA, ribosome, elongation factor (e.g., EF-Tu or EF-G), cofactor (e.g., GTP), or a combination thereof. Preferred labels are those that do not substantially impede the continuous and processive addition of amino acids in a protein synthesis reaction. Detectable labels may be directly or indirectly attached to reaction components, e.g., via a linking group or "linker." Such linking groups are known in the art and are further described and/or provided in U.S. Pat. No. 7,056,661 and U.S. Ser. No. 12/403,090, filed Mar. 12, 2009, the disclosures of which are incorporated herein by reference in their entireties for all purposes. Methods for detection and analysis of signals emitted from detectable labels are known in the art and certain preferred methods are further described in, e.g., U.S. Pat. Nos. 7,297,532 and 7,329,492; U.S. Patent Publication Nos. 20090024331, 20060228708, 20070036511, 20080080059, 20070188750, 20080277595, and 20070206187; Korlach, et al. (2008) Nucleosides, Nucleotides and Nucleic Acids 27:1072-1083; Eid, et al. (2009) Science 323:133-138; Blanchard (2004) PNAS 101(35): 12893-12898; Lundquist, et al. (2008) Optics Letters 33(9): 1026-1028; Wang, et al. (2007) Biochemistry 46:10767-10775; Uemura et al. (2008) Nucleic Ac. Res. 36(12):e70; Miyake et al. (2008) Anal. Chem. 80:6018-6022; and Levene, et al. (2003) Science 299:682-686, all of which are incorporated herein by reference for all purposes.

In certain embodiments, one or more labels are carried by aa-tRNAs in the reaction mixture. In some embodiments, a detectable label is attached to the amino acid to be incorporated into the polypeptide chain. However, this labeling strategy can introduce undesired structural or conformational changes to the polypeptide so in more preferred embodiments the incorporated amino acid does not comprise any labeling group and the newly synthesized polypeptide is therefore unlabeled (apart from any natural detectable characteristic of the polypeptide, e.g., intrinsic fluorescence.) See, e.g., Intrinsic Fluorescence of Proteins, vol. 6, publisher: Springer US, ©2001; Kronman, M. J. and Holmes, L. G. (2008) Photochem and Photobio 14(2): 113-134; Yanushevich, Y. G., et al. (2003) Russian J. Bioorganic Chem 29(4) 325-329; and Ray, K., et al. (2008) J. Phys. Chem. C 112(46): 17957-17963, both of which are incorporated by reference herein in their entireties for all purposes.

Various regions on an aa-tRNA may be modified to comprise a detectable label by standard biochemical methods, and in certain preferred embodiments the labeled aa-tRNA conjugation chemistry is designed such that the label is released from the ribosome complex upon incorporation of the amino acid (e.g., peptide bond formation). In certain embodiments, domains are engineered into the tRNA molecules to facilitate the use of common labeling techniques to efficiently label the tRNA molecules, e.g., with fluorophores or other detectable labels. Since only a few native tRNAs carry specific nucleobases that are easily conjugated with a label construct, introducing an artificial sequence at the ends or internally to all tRNAs at sites that do not interfere with the ribosome function would simplify tRNA labeling by providing a common "labeling region" on all tRNAs. Alternatively, a single or subset of tRNA backbones that are readily labeled can be modified to carry different anticodon regions and expressed to provide a set of aa-tRNAs having the same readily labeled backbone, but different anticodons. Charging of the resulting tRNAs by a tRNA synthetase that depends upon the anticodon region for amino acid specificity results in a set of aa-tRNAs comprising amino acids corresponding to their anticodons, but being more easily labeled than the wild-type aa-tRNA complexes.

Figure 2:
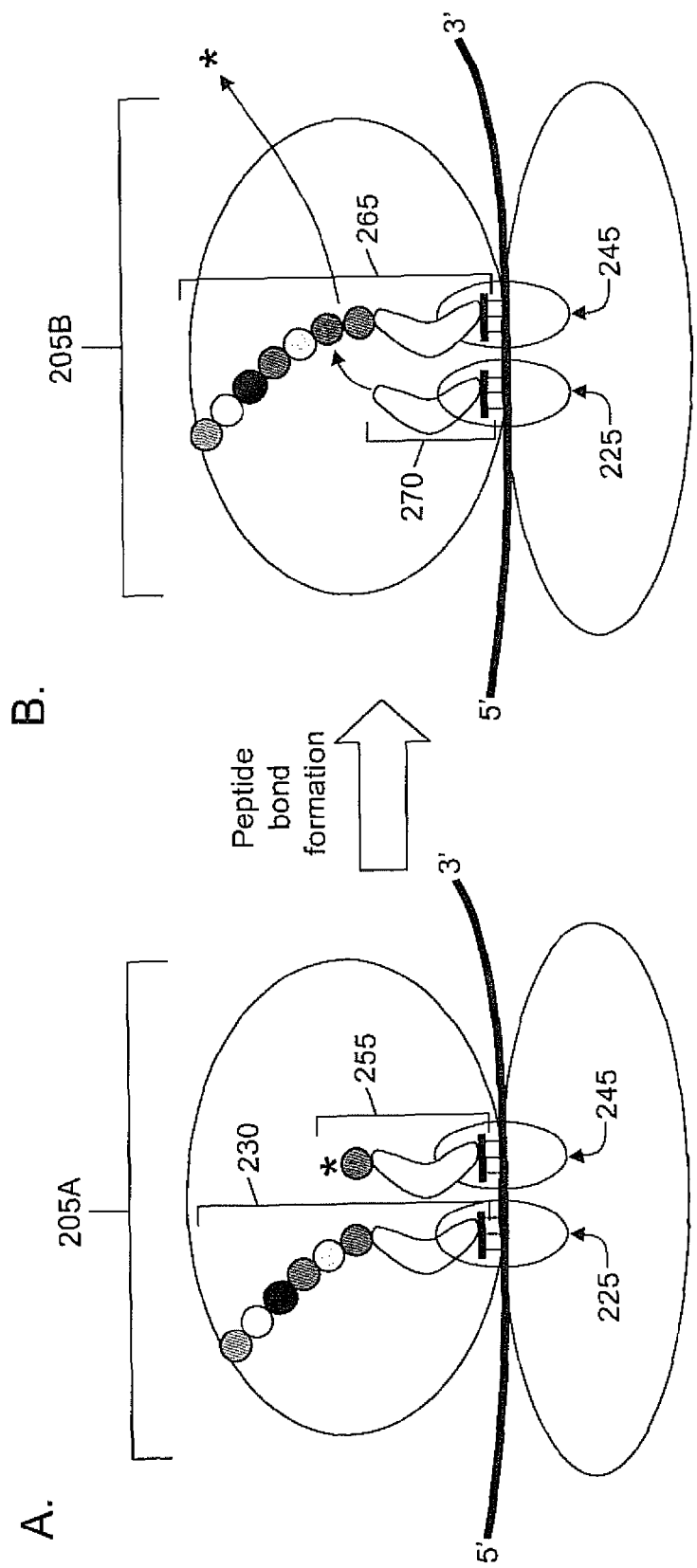
FIG. 2 provides an illustrative example of one embodiment of a labeling scheme for in vitro protein synthesis in which a detectable label on an aa-tRNA in the A site of a ribosome is released upon peptide bond formation.

FIG. 2 provides an illustrative example of an embodiment in which the label is cleaved from the incoming aa-tRNA upon peptide bond formation during the elongation cycle. In FIG. 2A, a ribosome complex (205A) is shown comprising a polypeptidyl-tRNA (230) at the P site (225) and an aa-tRNA (255) comprising a detectable label (*) at the A site (245). The label (*) is detectable on the ribosome complex (205A) during its residency on the aa-tRNA (245) in the A site (245), and this period of time is referred to as the "detectable period." Detection and subsequent identification of the detectable label (*) is indicative of one or more aspects of the aa-tRNA (245), e.g., the identity of the resident amino acid. FIG. 2B shows the same ribosome complex after peptide bond formation (205B), during which the N-formyl[amino acid] group of the polypeptidyl-tRNA (230) in the P site (225) is transferred to the amino group of the aa-tRNA (255) in the A site (245), thereby creating a polypeptidyl-tRNA in the A site (265) and a deacylated tRNA (270) in the P site (225). The linkage of the detectable label (*) to the aa-tRNA (255) is disrupted by formation of the peptide bond and the label is released and diffuses out of the observation volume, thereby ending the detectable period for that label. Various positions on the aa-tRNA can be engineered to carry a detectable label that is released upon peptide bond formation, e.g., a label at the epsilon amino group of the aa-tRNA. Clearly, since the label is removed from the incoming aa-tRNA during peptide bond formation, the initial methoinine residue at the first position may still contain a label. If it is desirable for the resulting polypeptide chain to be label-free, the initial fMet-tRNA$^{fMet}$ can be provided label-free prior to formation of the initiation complex.

Figure 3:
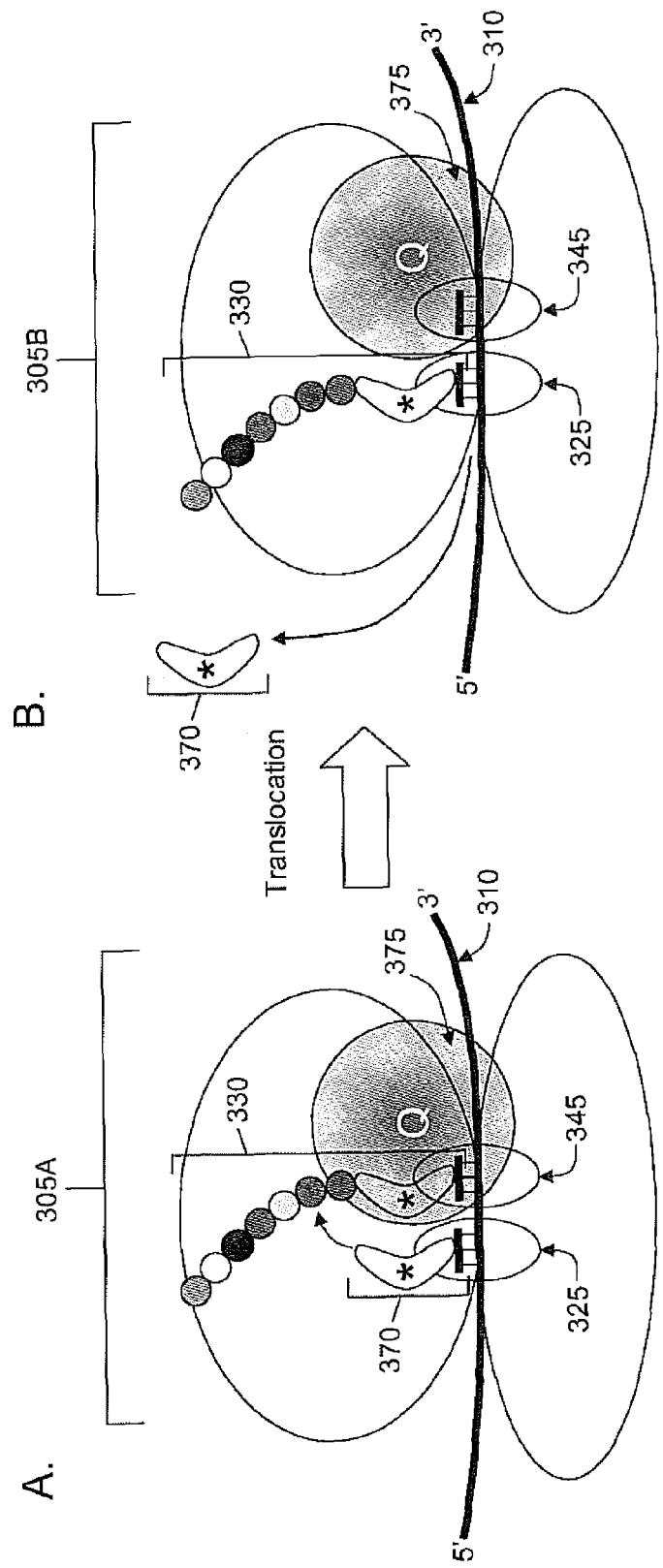
FIG. 3 provides an illustrative example of one embodiment of a labeling scheme for in vitro protein synthesis in which a quencher is present in the ribosome complex.

In other embodiments, the labeled aa-tRNA conjugation chemistry is designed such that the label remains on the deacylated tRNA and leaves the ribosome complex when the deacylated tRNA dissociates from the complex. For example, the elbow region of the tRNA can comprise a label retained by the deacylated tRNA in the P site of the ribosome. In such embodiments, multiple detectable labels can be present in the ribosome complex, e.g., when multiple labeled tRNAs are associated with the ribosome at the A, P, and/or E sites. As such, in certain embodiments the detectable periods for two or more labels overlap, creating simultaneously detectable signals, and such overlap must be factored into statistical analysis of the signals. Such signal overlap can also serve as validation that a particular amino acid was incorporated into the nascent polypeptide strand at a given position since the signal should overlap at least with signals corresponding to the immediately adjacent positions (+1 and -1 from the given position). For example, a signal with a very short duration (e.g., that does not overlap with the signal from the tRNA carrying the next-incorporated amino acid), can indicate that although the corresponding amino acid may have initially bound to the ribosome, it was not actually incorporated into the polypeptide. Alternatively, a quenching molecule may be positioned in the complex in such a way as to quench the signal from a first subset of the labels present in the complex while allowing signal from a second subset of labels to be detectable. In some embodiments such a quencher may quench signal from the A site, the P site, the E site, or a combination thereof For example, a quencher may be associated with the A and E sites so that only a label associated with the P site is detectable. FIG. 3 provides an exemplary embodiment in which a quenching moiety (375) is positioned to quench signal from a label(*) in the A (345) site, but not signal from a label (*) in the P site (325). In FIG. 3A a new peptide bond has just been formed by transfer of a polypeptide chain from the now deacylated tRNA (370) in the P site (325) to the now polypeptidyl-tRNA (330) in the A site (345). The label on the deacylated tRNA (370) is still detectable, but the label on the polypeptidyl-tRNA (330) is not. FIG. 3B shows the ribosome complex (305B) after translocation of the ribosome one codon toward the 3' end of the mRNA template (310). The detectable label previously in the A site (345) is now in the P site (325) of the ribosome, and its detectable period has begun. The detectable period for the label previously in the P site (325) continues as the deacylated tRNA (370) is transferred to the E site (not shown) and ends as it is subsequently released from the ribosome complex (305B). As such, signal from the E site and P site will be simultaneously detectable until release of the deacylated tRNA (370). Alternatively, a second quencher associated with the E site would end the detectable period upon transfer of the deacylated tRNA to the E site. The detectable period for the label on the now polypeptidyl-tRNA will continue through new peptide bond formation transferring the polypeptide chain to an aa-tRNA in the A site and until the resulting deacylated tRNA containing the label is released from the ribosome complex (305B). The retention of the label by the exiting deacylated tRNA can be particularly beneficial, e.g., where the deacylated tRNA can be recharged with a new amino acid and can again participate in elongation of the nascent polypeptide chain. Recharging of the deacylated tRNA can be promoted by including required components of aminoacylation in the reaction mixture, e.g., one or more aminoacyl-tRNA synthetases and free amino acids.

Figure 4:
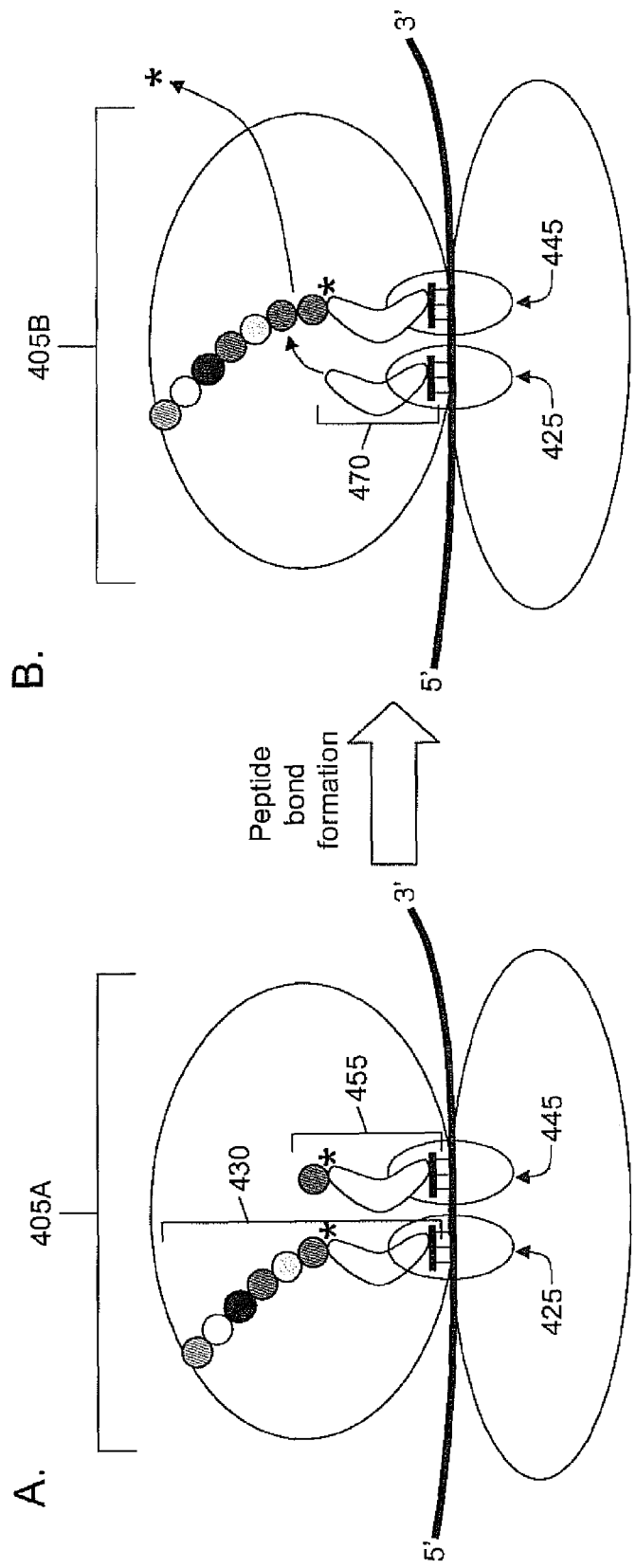
FIG. 4 provides an illustrative example of one embodiment of a labeling scheme for in vitro protein synthesis in which a detectable label on a polypeptidyl-tRNA in the P site of a ribosome is released upon peptide bond formation.

In other preferred embodiments, the labeled aa-tRNA conjugation chemistry is designed such that a detectable label on a polypeptidyl-tRNA is released from the ribosome complex upon peptide bond formation and transfer of the resident polypeptide to an aa-tRNA in the A site. FIG. 4 provides an illustrative example of such an embodiment. In FIG. 4A a labeled polypeptidyl-tRNA (430) is in the P site (425) and a labeled aa-tRNA (455) is in the A site (445). During peptide bond formation and transfer of the polypeptide chain to the A site (445) the label (*) on the tRNA in the P site (425) is released, as shown in FIG. 4B. As for the embodiment described above in which the label remains on the deacylated tRNA and leaves the ribosome complex when the deacylated tRNA dissociates from the complex, this embodiment also produces overlapping detectable periods for labels associated with the ribosome complex, but in this case it is a shorter period of time ending upon peptide bond formation rather than release of the deacylated tRNA (470). Put another way, two detectable labels are present in the ribosome complex for the period of time beginning when an aa-tRNA binds to the A site until peptide bond formation. As such, the overlapping detectable periods for co-resident labels must be factored into statistical analysis of the signals.

Figure 5:
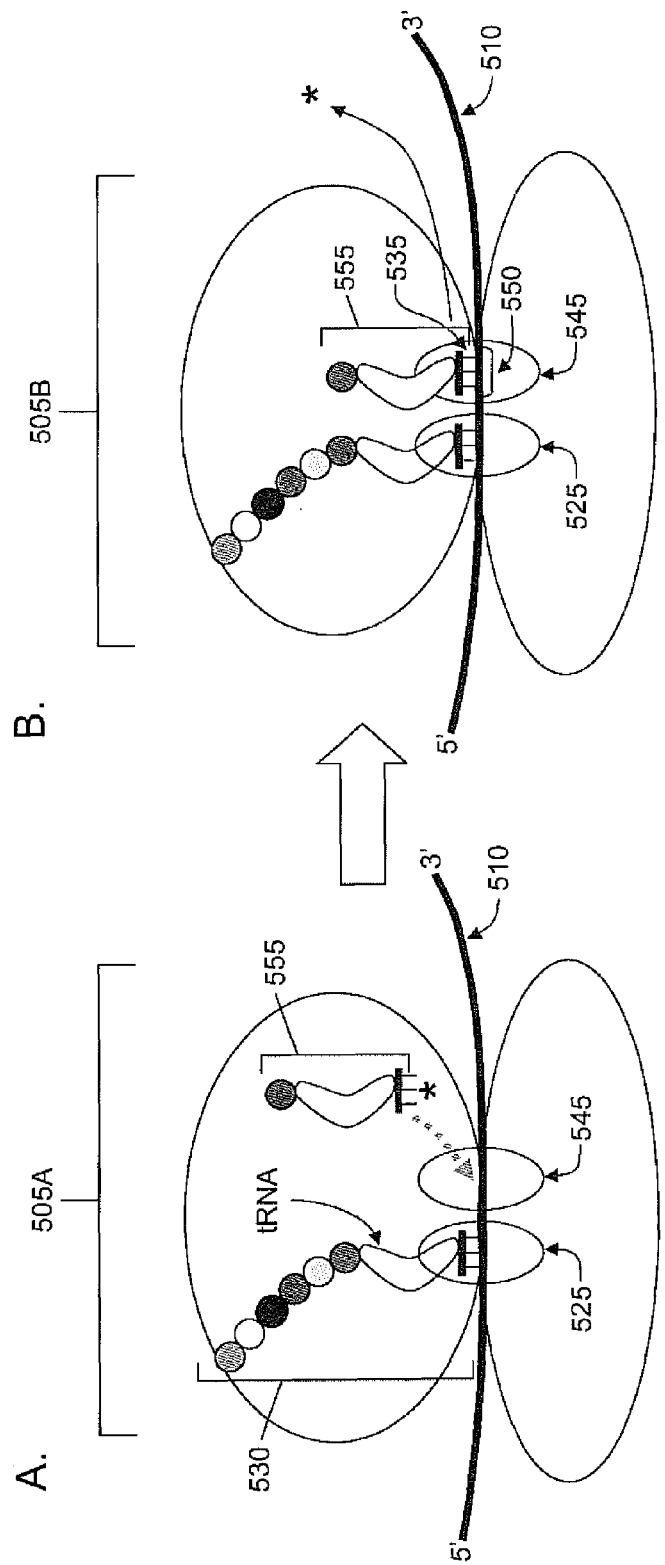
FIG. 5 provides an illustrative example of one embodiment of a labeling scheme for in vitro protein synthesis in which a detectable label on an aa-tRNA is released upon binding to a complementary codon of an mRNA template that is in the A site of a ribosome.

In certain embodiments, binding of an aa-tRNA to the ribosome complex causes dissociation of a detectable label, e.g., located near or on the anticodon arm. In one such embodiment, a small labeled oligonucleotide complementary to the anticodon is displaced by binding of the anticodon to the complementary codon in the template mRNA molecule. For example, FIG. 5 provides an illustrative example of one such embodiment. In FIG. 5A, a ribosome complex (505A) comprises a polypeptidyl-tRNA (530) in the P site (525) and an empty A site (545) that is ready to receive an aa-tRNA (555), which is shown approaching the A site. In FIG. 5B, the aa-tRNA (555) has bound to the A site (545) of the ribosome complex (505B), and this binding has caused release of the detectable label (*), e.g., due to the association of the anticodon (535) of the aa-tRNA (555) with the complementary codon (550) in the mRNA template (510). As such, the detectable period begins once the incoming aa-tRNA is within an observation region (e.g., reaction site) and ends upon release of the detectable label and its subsequent diffusion out of the observation region.

Figure 6:
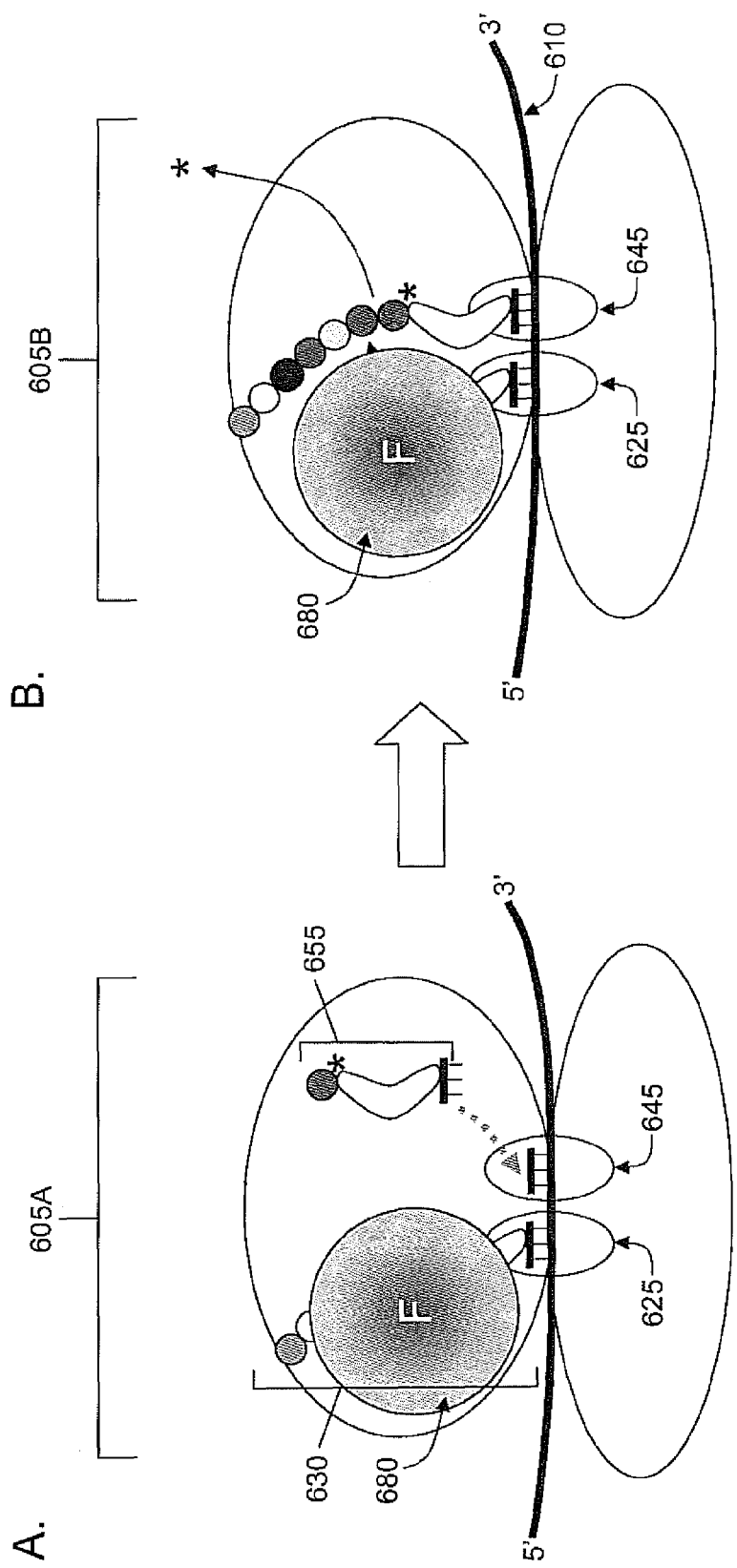
FIG. 6 provides an illustrative example of one embodiment of a labeling scheme for in vitro protein synthesis in which FRET labels are present in the ribosome complex.

In some preferred embodiments, multi-component detectable labels are used to detect and subsequently identify amino acid residues incorporated into a polypeptide chain during synthesis. For example, as described above, detectable labels can be FRET labels, consisting of at least one "donor" and one "acceptor" chromophore (e.g., fluorophore). The examples provided herein will focus on FRET labels with a single donor and a single acceptor fluorophore, but it is to be understood that FRET labels for use with the instant invention include those with more than one donor and/or acceptor, and those using labeling groups other than fluorophores. In short, various labeling strategies described at length above, as well as others that will be apparent in light of the teachings herein, can include at least one reaction component having at least one FRET label. For example, FIG. 6 provides an exemplary embodiment in which one component of a FRET label is linked to the ribosome and a second component of a FRET label is linked to an aa-tRNA. For example, in preferred embodiments the donor fluorophore is linked to the ribosome and the acceptor chromophore is linked to the aa-tRNA in such a way that the acceptor fluorophore emits a signal only when in proximity to the donor chromophore, and the signal is indicative of the amino acid moiety resident in the aa-tRNA. In FIG. 6A, a ribosome complex (605A) is shown having FRET donor (680), a polypeptidyl-tRNA (630) bound to the P site (625), and an aa-tRNA (655) entering the A site (645). Signal is being emitted from the detectable label (*) linked to the polypeptidyl-tRNA (630) since it is near enough to the FRET donor (680) to be excited; the detectable label (*) on the aa-tRNA (655) in the A site (645) is too far from the FRET donor (680) to be excited, and so does not emit a signal. In Figure B, the ribosome complex (605B) has experienced peptide bond formation between the polypeptide formerly in the P site (625) and the amino acid on the aa-tRNA (655) in the A site (645). This reaction causes release of the label (*) from the P site (625) and thereby ends the detectable period for that label. At this point, there is no signal being emitted from the remaining acceptor fluorophore (*) in the A site (645) of the ribosome complex (605B) due to its distance from the donor fluorophore (680). Upon translocation (not shown) of the ribosome complex one codon toward the 3' terminus of the mRNA template (610), the P site moves to associate with the detectable label on the newly formed polypeptidyl-tRNA, thereby initiating the detectable period for that label. This process repeats for each new amino acid incorporated into the growing polypeptide strand. One advantage to this strategy is that there is a "quiet period" between each detectable period during the time when a new peptide bond has been formed but translocation of the ribosome has not yet occurred. This quiet period can be used to "mark" the signal traces for the synthesis reaction, providing an indication of transitions between signals for adjacent amino acid incorporations. Further, in such embodiments, multiple aa-tRNAs can be distinctly labeled with acceptor fluorophores that are excited by the same donor fluorophore, but that have distinctive emission spectra and are therefore indicative of their resident amino acids. These and other embodiments using multiple distinctly labeled aa-tRNAs are described in greater detail below.

Labeling of a tRNA should not disrupt the interaction of the tRNA with the aminoacyl synthetase, ribosomal machinery, or elongation factor EF-Tu (or, in eukaryotes, eEF1α). Further, in preferred embodiments, the tRNA label has a high binding rate to ensure that at least 90%, or more preferably at least 95%, or at least 98% or at least 99% of the tRNA species to be labeled are actually labeled. Various methods for labeling tRNA molecules while retaining their functional interaction with aminoacyl synthetases, ribosomes, and elongation factors are known in the art, e.g., in Betteridge, T., et al. (2007) RNA 13:1594-1601; Pan, D., et al. (2009) RNA 15: 346-354; Blanchard, S. C., et al. (2004) Proc. Natl. Acad. Sci. 101(35): 12893-12898; Watson, et al. (1995) Biochemistry 34(24): 7904-12; Plumbridge, et al. (1980) Nucleic Acids Res. 8(4): 827-43; Jia, et al. (1997) Proc Natl Acad Sci USA. 94(15): 7932-6; Johnson, et al. (1982) J. Mol. Biol. 156, 113-140; Wintermeyer and Zachau (1971) FEBS Lett. 18(2):214-218); U.S. Patent Pub. No. 2006/0228708 A1; and U.S. Pat. No. 7,297,532, all of which are incorporated herein by reference in their entireties for all purposes. Specific sites of interest for labeling the aa-tRNA include labeling the RNA or amino acid portion of the molecule. Labeling of the RNA portion can be accomplished, e.g., by synthesizing the tRNA with an amino linker that can be derivatized. Suitable sites include the anticodon stem loop, the elbow region, the shoulder region (such as in positions 8 and 47 of E. coli tRNAs), and the 3' acceptor arm. Alternatively, the amino acids can be labeled prior to the appropriate aminoacyl synthetase using them to charge the tRNA. In other embodiments, the intrinsic fluorescence of some tRNA species can be used as a detectable label.

In some embodiments, tRNA labeling strategies can be used that reveal an amino acid sequence encoded in the mRNA template, but do not necessarily result in a nascent polypeptide comprising that amino acid sequence. As such, the sequence of the mRNA template can be derived to the extend that the genetic code will allow given that some anticodons can anneal to more than one codon. For example, all tRNAs can be charged with the same or a subset of amino acids; or a single tRNA backbone can be modified to create a set of tRNAs with essentially the same backbone but different codons. Such methods are described in greater detail below.

Although some preferred embodiments operate with a "natural" ribosome (e.g., unlabeled or otherwise unmodified), other strategies involve labeling and/or other modifications to the ribosome, e.g., addition of a label or quencher linked to one or more ribosomal proteins or ribosomal RNAs (rRNAs); or use of detectably labeled molecules that specifically associate with the complex, e.g., labeled antibiotics specific for the complex. Certain embodiments were provided in the FRET and quencher examples above. In certain embodiments, a detectable label on the ribosome is placed near the A, P, or E site. For example, ribosomal proteins L1, S1, and S21 are known to be near the E site. Experiments have shown that these proteins can be efficiently labeled while retaining ribosome functionality. See, e.g., Mascarenhas, et al. (2001) EMBO Rep. 2(8):685-9; and Odom, et al. (1984) Archiv. Biochem. Biophys. 230(1):178-193, both of which are incorporated herein by reference for all purposes. Ribosomes may be labeled by direct fluorescent labeling of ribosomal RNA (e.g., using hybridization tags) or by using a peptide tagging strategy (e.g., see Campisi, et al. (2001) EMBO J. 20(1-2): 178-86). Further examples of methods for labeling ribosomes are provided, e.g., in U.S. Patent Publication No. 2006/0228708, U.S. Pat. No. 7,297,532; and Blanchard, S. C., et al. (2004) Proc. Natl. Acad. Sci. 101(35): 12893-12898, all of which are incorporated by reference herein. For example, another approach for rRNA labeling utilizes internal incorporation of dyes by ligation of 16S rRNA fragments that contain dyes at their 5' or 3' termini. For example, 16S rRNA can be transcribed as two pieces, with a dye-labeled dinucleotide as primer of transcription. The two strands are then ligated by DNA ligase and a DNA splint. The 30S subunit is then reconstituted from total 30S proteins using standard protocols. Ribosomal proteins may also be labeled by introduction of non-natural amino acids (Masahiko, S., et al. (2006) Protein, Nucleic Acid and Enzyme 51(5): 399-407); Hohsaka, T., et al. (2003) Nucleic Acids Research Supplement 3: 271-272, both of which are incorporated by reference herein in their entireties for all purposes. For double-labeling of different subunits, the individual subunits can be separated and labeled independently using combinations of one or more peptide and/or hybridization tags. Labeled peptide or polynucleotide probes can be synthesized and derivatized with a fluorescent tag. The labeled probes can then be incorporated into cell growth media, or bound to the ribosomes post-synthetically. When bound to the ribosome during synthesis the probes flutter provide a means investigating the in vivo process of ribosome assembly.

In certain preferred embodiments, elongation factors may be labeled to facilitate detection of amino acid incorporation during protein synthesis. There are three elongation factors in prokaryotes, EF-Tu, EF-Ts, and EF-G; the elongation factors having analogous functions in eukaryotes are eEF1α, eEF1βγ, and eEF2, respectively. The functions of the elongation factors are well known to those of ordinary skill in the art. In brief, EF-Tu (eEF1α) binds a molecule of GTP and an aa-tRNA. Binding of the aa-tRNA to the A site in the ribosome is accompanied by hydrolysis of the GTP to GDP and Pi, and an EF-Tu•GDP complex leaves the ribosome. The bound GDP is released when the EF-Tu•GDP complex binds to EF-Ts (eEF1βγ) and EF-Ts is subsequently released when another molecule of GTP binds to EF-Tu, which can then bind another aa-tRNA. EF-G (eEF2) is involved in translocation through hydrolysis of a bound GTP to GDP. (See, e.g., Wang, Y., et al. (2007) Biochemistry 46:10767-10775, incorporated herein by reference in its entirety for all purposes.) The energy provided by hydrolysis allows the ribosome to move one codon toward the 3' end of the mRNA template. EF-Tu and EF-G are particularly preferred as labeled components due to their close proximity to the ribosome complex during peptide synthesis, and they may be labeled with single or multi-component labels, as described above. A further advantage to using these elongation factors as labeled reaction components is that they are naturally released from the ribosome after binding/incorporation or translocation, which benefits the analysis in a number of ways, as described further below.

In certain preferred embodiments, both EF-Tu•GTP and one or more aa-tRNAs carry a delectable label. The EF-Tu•GTP may contain a label on the EF-Tu portion or the GTP portion, e.g., on a terminal phosphate removed during hydrolysis of EF-Tu•GTP to EF-Tu•GDP. (The use of labeled GTP cofactors is discussed at length below.) The detection of the label from the aa-tRNA identifies the cognate amino acid, and the label on the EF-Tu•GTP indicates a potential for binding and incorporation of that cognate amino acid. The signals detected from the EF-Tu•GTP molecules further provide a tally of the number of times an EF-Tu•GTP/aa-tRNA complex is sampled by the ribosome complex between each incorporation event, and this can be particularly valuable in embodiments in which only a subset of aa-tRNAs comprise detectable labels or in applications for studying various other kinetic aspects of protein synthesis.

In certain embodiments, the detectable period for the label on a tRNA continues through peptide bond formation, translocation to the P site, and incorporation of the subsequent amino acid at the A site. In such cases, the detectable period for the label on the tRNA that occupies the P site is expected to overlap with the detectable period for a label on a newly arrived tRNA in the A site, and such overlapping signals from tRNAs residing on the ribosome complex provide validation of which amino acids were actually incorporated and which were rejected subsequent to dissociation of EF-Tu•GDP. The overlapping signals detected from these labels (i.e., those from the tRNAs as well as those from the EF-Tu•GTP) can be distinguished from one another during statistical analysis. Even where two tRNAs bound to the ribosome complex are the same (e.g., both carry the same amino acid and the same detectable label), the intensity of one or more peaks in the emission spectrum is greater than the intensity for a single label emission, and thereby indicative of the presence of multiple labels with identical emissions. Standard statistical analysis of the detected emissions over time will identify the label(s) generating the detectable signal and how many of each are present, thereby allowing reconstruction of the sequence of binding and incorporation events on the ribosome complex during elongation of the polypeptide chain, thereby generating sequence information for the polypeptide being synthesized.

Figure 7:
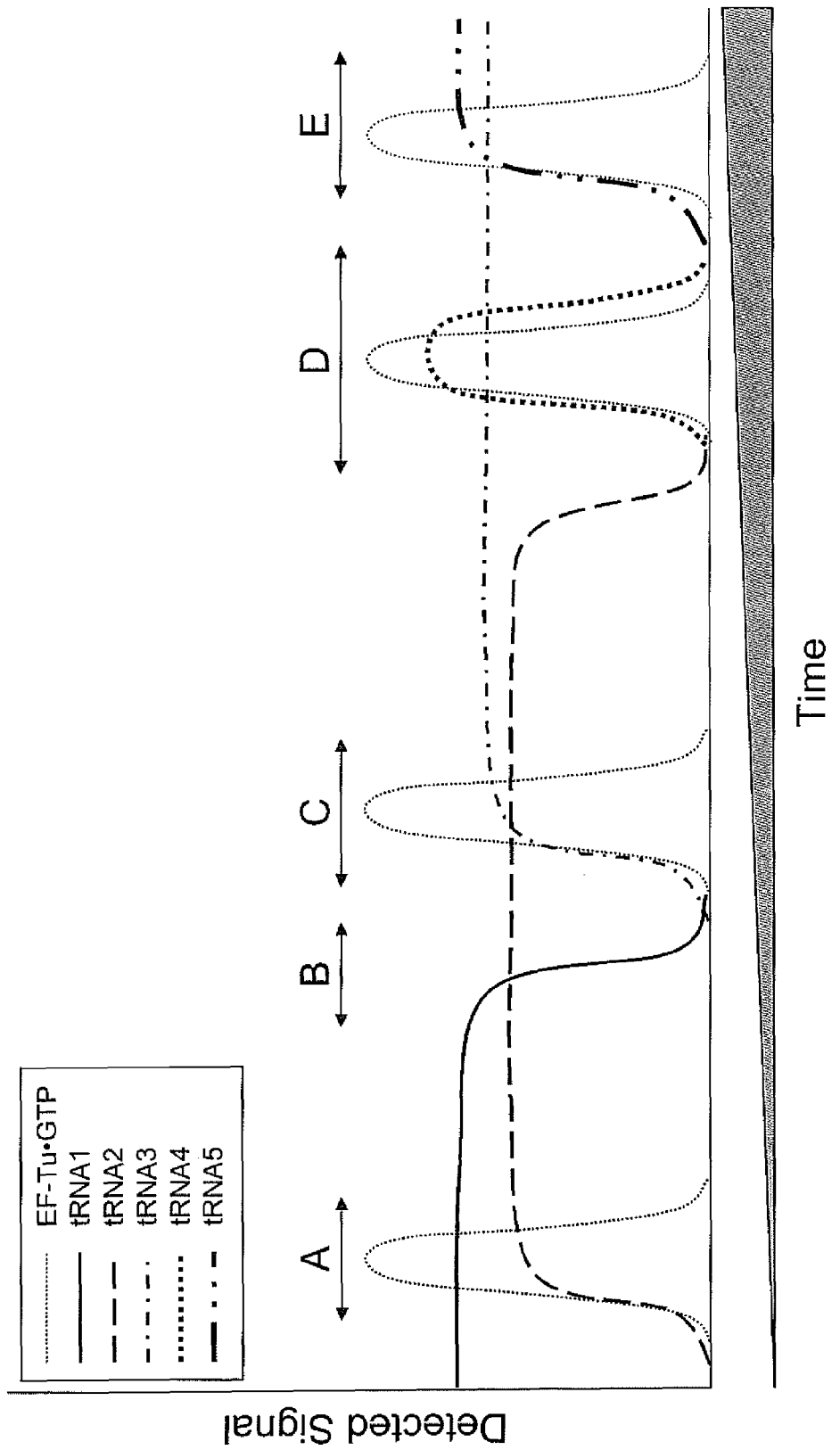
FIG. 7 provides a graphical representation of detectable signal emissions during one embodiment of a protein synthesis reaction in which both EF-Tu and tRNAs comprise detectable labels.

FIG. 7 provides an illustrative example of an embodiment in which both EF-Tu and tRNAs comprise detectable labels, all of which are optically distinguishable in the reaction. For example, each different label produces a different emission spectrum upon excitation so that detection of the emission unambiguously identifies the molecule from which it originated, e.g., a particular tRNA or EF-Tu. The figure is a graphical representation of detectable signal emissions during the reaction, with certain portions of interest indicated as periods A-E. The legend indicates which molecule is represented by each line in the time course. In period A, labeled EF-Tu•GTP bound to labeled aa-tRNA2 enters the observation volume and two signals become detectable, one from each label, in addition to the label from tRNA1 occupying the P site of the ribosome complex. aa-tRNA2 binds to the ribosome complex and the post-hydrolysis EF-Tu•GDP is released and diffuses away, thereby ending the detectable period for the label on the EF-Tu but not the detectable period for the label on the tRNA2, now bound to the A site of the ribosome complex. In period B, the detectable period for tRNA1 ends, indicating the ribosome complex translocated, facilitating release of tRNA1 from the ribosome complex. In period C, a second labeled EF-Tu•GTP bound to labeled aa-tRNA3 enters the observation volume, and subsequently the detectable period for a label on tRNA2 is lost. Period D illustrates signal traces for a labeled aa-tRNA that enters the observation volume but does not bind to the ribosome complex. As in periods A and C, labeled EF-Tu aid tRNA4 arrive at the comples with the signal from EF-Tu ending shortly thereafter. Unlike periods A and C, the signal for tRNA4 also ends shortly thereafter, e.g., prior to the arrival of a subsequent EF-Tu•GTP/aa-tRNA complex, and there is no subsequent loss in signal from tRNA3 further indicating there was no incorporation of the cognate amino acid bound to tRNA4 into the growing polypeptide. As such, period D represents a "sample event." In period E, a fourth labeled EF-Tu and tRNA5 arrive in the observation volume and, based on the visible trace, it appears the cognate amino acid bound to tRNA5 will be incorporated into the nascent polypeptide chain. The incorporation is confirmed by both the loss of tRNA3 prior to (and the retention of the signal corresponding to tRNA5 through) the arrival of the next EF-Tu•GTP/aa-tRNA complex.

In some embodiments, EF-Tu is linked to a FRET donor that excites a detectable label on an aa-tRNA bound thereto. As the EF-Tu•GTP/aa-tRNA complex enters the observation volume a signal is detected, and the detectable signal ends upon dissociation of the EF-Tu•GDP from the ribosome complex, commencing a dark period during which time no signal is emitted from labels in the reaction site. In some embodiments, EF-Tu-associated FRET donors are relatively short-range, only exciting the FRET acceptors associated with the aa-tRNA to which they are bound. In other embodiments, EF-Tu-associated FRET donors are longer-range and excite multiple FRET acceptors linked to tRNAs bound to multiple positions in the ribosome complex (e.g., in both the A and P sites, or alternatively also the E site). For example, the overlapping signals from multiple FRET acceptors on tRNAs associated with the ribosome provide confirmation of which amino acids were incorporated into the growing polypeptide chain. As for the non-FRET embodiments described above, the individual signals detected from these labels can be extracted during statistical analysis from the overall emission spectra to identify the labels, and therefore the amino acids associating with the ribosome complex. Further, the location and means of attachment (e.g., type of linker) of the FRET donor on the EF-Tu molecule can be selected to ensure a desired distance between the FRET donor and other FRET acceptors during binding of the incoming tRNA (e.g., FRET acceptors on the incoming tRNA to which EF-Tu is bound, or other tRNAs associated with the ribosome). Such distances can be readily determined by the ordinary practitioner, e.g., based on knowledge of the range of the FRET donor, the architecture of the EF-Tu•GTP/aa-tRNA complex, the way in which and the EF-Tu•GTP/aa-tRNA complex associates with the ribosome, and the distances between the A, P, and E sites on the ribosome.

Both the non-FRET and FRET labeling schemes described above also produce signal for those EF-Tu•GTP/aa-tRNA complexes that enter the observation volume but for which an amino acid incorporation event does not occur. As such, they are particularly useful for studying the kinetics of the binding and subsequent release of EF-Tu•GDP, both in the presence and absence of incorporation. For example, labeled Phe-tRNAs can be added to a ribosome complex translating an mRNA encoding a polypeptide sequence that does not contain phenylalanine, and the kinetics of sampling the EF-Tu•GTP/Phe-tRNA complex can be observed by detecting the signal from the complex. These kinetics can be compared to sampling of the same EF-Tu complex for an mRNA template that encodes a polypeptide comprising phenylalanine.

In some embodiments, EF-Tu is linked to a quencher that quenches a detectable label on an aa-tRNA bound thereto. In such an embodiment, the signal from the incoming aa-tRNA is quenched until dissociation of the EF-Tu•GDP from the ribosome complex at which point the detection period for this label begins. The label on the aa-tRNA may be configured in various ways, as described above, and may be associated with the amino acid or tRNA portion of the complex. For example, in certain embodiments, the label is released and the detection period ends upon peptide bond formation between the amino acid in the A site and the polypeptide in the P site (e.g., as described above). In some embodiments in which the label is linked to the tRNA portion, a second quencher can be present in the ribosome to quench signal from the P and E sites, thereby only allowing signal from the A site to be detected. Alternatively (e.g.,in the absence of a second quencher in the ribosome), the arrival of an EF-Tu•GTP/aa-tRNA complex having a relatively long-range quencher at the A site can cause a "dark period" that quenches multiple labels in the reaction site, e.g., on tRNA complexes in the A and P sites. Such a dark period is indicative of the arrival of a new aa-tRNA complex at the ribosome and the detectable signal before and after the dark period is indicative of whether an incorporation event occurred or whether the incoming aa-tRNA was simply rejected from the complex after dissociation of EF-Tu•GDP. That is, if the detectable signal, which is a combination of emission spectra from all detectable labels in the reaction site, is the same before and after the dark period, then no new label was retained by the ribosome complex and therefore no new aa-tRNA was bound to the ribosome complex and no new amino acid be incorporated into the polypeptide chain. Overlapping signals from simultaneously emitting detectable labels and be subjected to various statistical analyses known to those in the art to extract individual signals for individual labels, e.g., to identify the tRNAs associated with a ribosome complex during a given period of time, and therefore the amino acids being incorporated into a polypeptide chain.

In certain preferred embodiments, EF-G•GTP and one or more aa-tRNAs carries a detectable label. In such embodiments, signal(s) emitted from one or more aa-tRNAs associated with the ribosome complex identifies their cognate amino acids, and an overlapping signal from an EF-G•GTP complex provides an indication of the incorporation of the identified amino acids. Briefly, association of EF-G•GTP with the ribosome complex occurs after peptide bond formation has transferred the growing polypeptide chain from the tRNA in the P site to the aa-tRNA in the A site. As such, both tRNAs present in the ribosome complex during translocation correspond to (i.e. were or are currently bound to) amino acids that are incorporated into the polypeptide chain, with the order of dissociation of each tRNA from the ribosome complex following each translocation indicating the order of amino acid incorporation. For example, if a first signal from an EF-G•GTP complex overlaps with signals from a Phe-tRNA and a Ser-tRNA, and a next signal from the EF-G•GTP complex overlaps with signals from a Phe-tRNA and a Thr-tRNA, then it can be concluded that an order of amino acid incorporations into the polypeptide chain is Ser-Phe-Thr.

Figure 8:
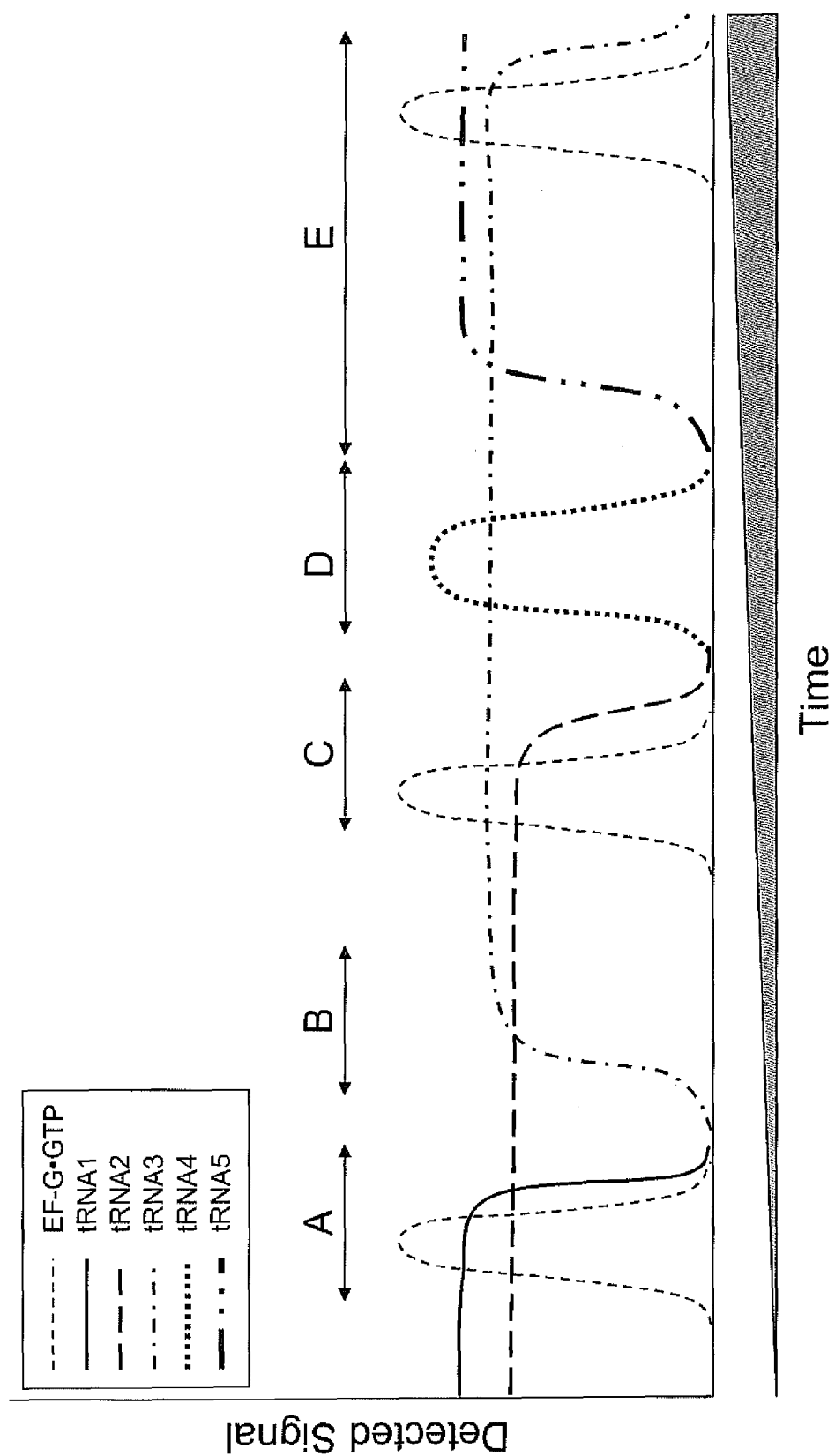
FIG. 8 provides a graphical representation of detectable signal emissions during one embodiment of a protein synthesis reaction in which both EF-G and tRNAs comprise detectable labels.

FIG. 8 provides an illustrative example of an embodiment in which both EF-G and tRNAs comprise detectable labels, all of which are optically distinguishable in the reaction. Like FIG. 7, FIG. 8 is a graphical representation of detectable signal emissions during the reaction, with certain portions of interest indicated as periods A-E. The legend indicates which molecule is represented by each line in the time course. In period A, labeled EF-G•GTP enters the observation volume and three signal are detectable, one from each of EF-G, tRNA1 (in the P site), and tRNA2 (in the A site). After translocation, labeled EF-G•GDP dissociates from the ribosome complex, followed shortly thereafter by tRNA1. A new signal is detected during period B, indicating that a new tRNA has associated with the ribosome complex. During period C, a second EF-G•GTP signal followed by the loss of signal from tRNA2 and retention of the signal from tRNA3 indicate that the ribosome has translocated along the template and that the cognate amino acid from tRNA3 was incorporated into the polypeptide chain. Period D illustrates a sample event during which tRNA4 is sampled and rejected by the ribosome complex; no signal from EF-G or loss of signal from tRNA3 follows the sample event. Rather, the signal from tRNA3 is retained by the complex through binding of tRNA5 with the complex, and is only lost after the EF-G signal (indicationg translocation) in period E. The series of combinations of tRNA label signals that overlap the EF-G label signals is indicative of the amino acid sequence of the nascent polypeptide chain since the practitioner can track the progress of a given tRNA, and hence its cognate amino acid, by virtue of its detection during translocation.

In certain preferred embodiments, EF-G is linked to a FRET donor that excites a FRET acceptor on an aa-tRNA and/or polypeptidyl-tRNA, much in the same manner as the ribosome-linked FRET donor described above. In such an embodiment, the detectable period for a detectable label begins upon entry of EF-G into a given area defined by the distance required for energy transfer, e.g., while associating with a ribosome complex during translocation. The detectable period ends upon dissociation of EF-G and its diffusion away from the ribosome complex to produce a dark period, as described above. As such, for an EF-G-associated FRET donor that excited only a label in the P site, a signal indicative of a given amino acid is emitted and detected only after proofreading, thereby ensuring that the amino acid is in fact being incorporated and not simply being transiently bound by the ribosome prior to being ejected without incorporation. In other embodiments, an EF-G-associated FRET donor with a relatively longer range will excite multiple FRET acceptors in its vicinity, e.g., in multiple sites on the ribosome complex to generate an emission comprising signal from multiple labels. As described for EF-Tu-associated FRET donors, the individual signals detected from these labels can be extracted during statistical analysis from the overall emission spectra to identify the labels, and therefore the amino acids associating with the ribosome complex; analysis of the signals detected over time allows reconstruction of the elongation cycle and generates sequence information for the polypeptide being synthesized. As will be clear to those of ordinary skill, any labeling of elongation factors must be compatible with their necessary functions during protein synthesis, e.g., binding of aa-tRNA to the A site and translocation.

Figure 9:
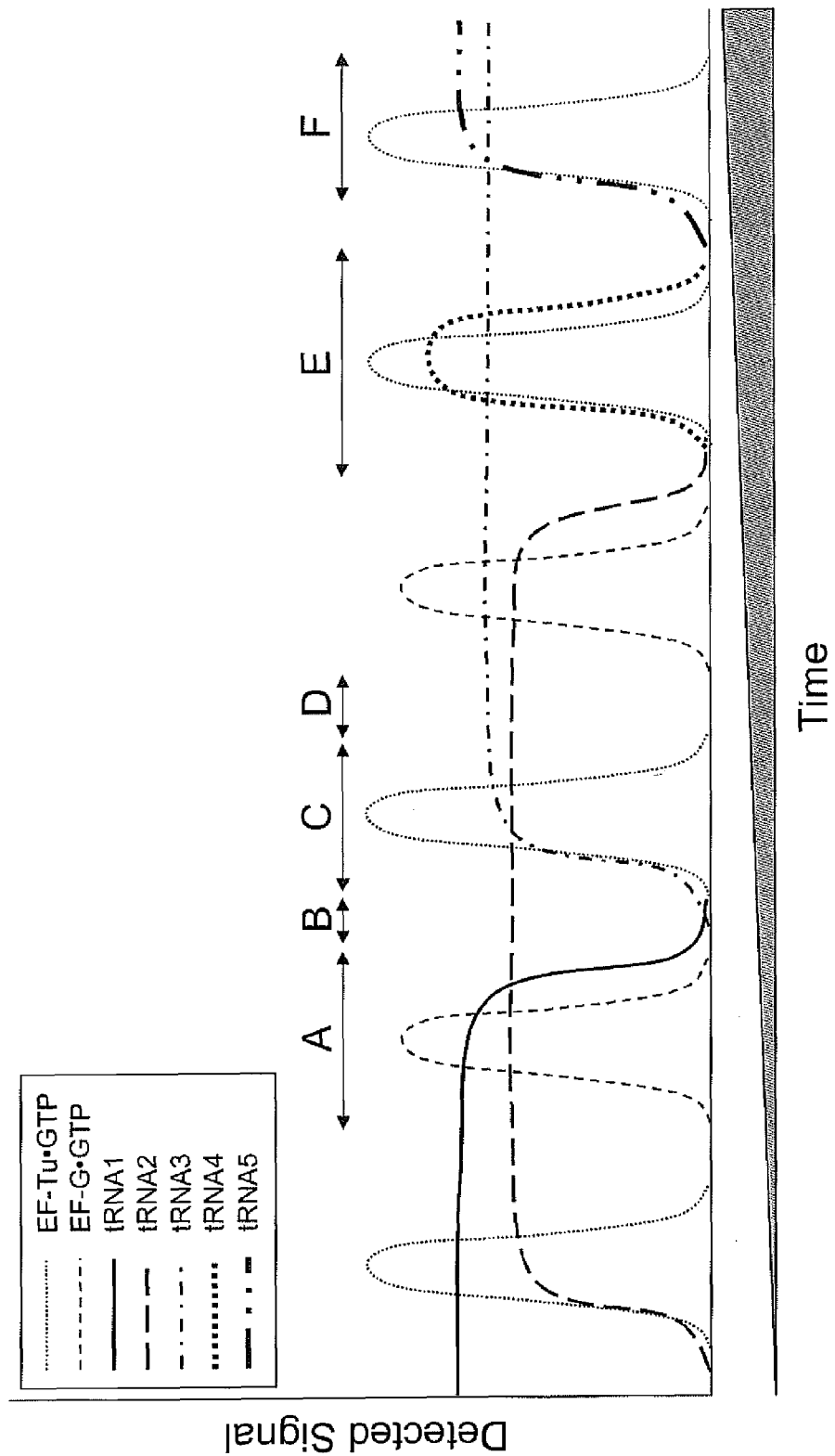
FIG. 9 provides a graphical representation of detectable signal emissions during one embodiment of a protein synthesis reaction in which EF-Tu, EF-G, and tRNAs comprise detectable labels.

In yet further embodiments, both EF-Tu and EF-G can be differentially labeled in a protein synthesis reaction. If no aa-tRNAs are also labeled, analytical reactions can be used to monitor the kinetics of sampling and incorporation during a reaction, e.g., under various reaction conditions as described elsewhere herein. Alternatively, one or more aa-tRNAs in the reaction can also carry detectable labels. FIG. 9 provides a graphical representation of detectable signal emissions during a reaction in which EF-Tu, EF-G, and tRNAs comprise detectable labels, all of which are optically distinguishable in the reaction. During period A, EF-G•GTP catalyzes translocation of the ribosome along the mRNA template. In addition to the signal emitted from the labeled EF-G, signal is also being emitted from tRNA1 being transferred from the P site to the E site, and tRNA2 being transferred from the A site to the P site. The signal from tRNA1 ends as the molecule is released from the ribosome complex and diffuses out of the observation volume. Following translocation there are no labeled elongation factors in the observation volume, but signals are detectable from as many as three tRNAs. Period B depicts detectable signals from three tRNAs: one exiting the E site, one occupying the P site, and one entering the A site. In period C, EF-Tu•GTP catalyzes binding of incoming tRNA3 (with its cognate amino acid) to the A site; signal is detectable from the labeled EF-Tu, incoming tRNA3, and tRNA2 in the P site. In period D, only signal from labels on the tRNAs in the P and A sites (tRNA2 and tRNA3) are detectable since the E site is empty.

Period E illustrates a case in which an aa-tRNA brought to the ribosome complex by EF-Tu•GTP is subsequently rejected and dissociates without polypeptide bond formation. Emissions from labels on the EF-Tu and tRNA4 (as well as signal from the tRNA3 label) are detectable during the "sampling" of the aa-tRNA by the ribosome complex. The signal from the EF-Tu ends as the elongation factor released from the complex and diffuses away, and shortly thereafter the signal from tRNA4 also ends due to the rejection of the aa-tRNA by the ribosome. This period can be identified as a sample event due to the similar characteristics of the periods immediately prior to and following the EF-Tu signal. That is, both are characteristic of a period following a translocation event (as shown for period B), and this is indicative that a sampling event occurred. During period F, an EF-Tu•GTP carrying tRNA5 (with its cognate amino acid) associates with the ribosome complex, and the detectable signals from tRNA3 and tRNA5 after dissociation of the EF-Tu label indicate that tRNA5 is binding to the A site and has not been rejected.

In certain embodiments, and as noted above, GTP cofactors can comprise a detectable label, e.g., in the EF-Tu•GTP complex during initial binding of the aa-tRNA to the A site and in the EF-G•GTP complex during translocation of the ribosome complex along the template after peptide bind formation. These labeled GTP cofactors can be used in the presence or absence of labeled aa-tRNA complexes, but various benefits are realized when both types of labels are used in combination, as described below. Since the GTPs are all identically labeled, the EF-Tu•GTP complex is not optically distinguishable from the EF-G•GTP complex, but the emissions detected between each GTP label emission allow such distinction. Specifically, the period following binding and prior to translocation is characterized by the loss of one tRNA from the E site, a steady signal from a second tRNA in the P site, and the addition of a third tRNA to the A site. In contrast, the period following translocation and prior to binding is characterized by relatively steady emissions front two tRNAs in the A and P sites. These patterns are identified during statistical analysis of the emission signals detected, thereby allowing the progress of the reaction to be monitored and recorded, and the sequence of amino acids incorporated into the growing polypeptide chain to be determined.

GTP cofactors can be labeled in various ways known to those of skill in the art, as long as the labeling strategy does not interfere with their ability to participate in the protein synthesis reaction, e.g., through binding to a particular elongation factor and/or undergoing hydrolysis. For example, the label may be directly or indirectly linked to the base, sugar, or phosphate chain, and various methods of labeling nucleotides are known in the art, e.g., in U.S. Pat. No. 7,056,661, incorporated herein by reference in its entirety for all purposes. In certain preferred embodiments, the label is linked to a phosphate moiety that is removed during hydrolysis of the cofactor to GDP, e.g., on a terminal phosphate. Although generally referred to as "GTP" herein, the GTP cofactor may comprise additional moieties, e.g., additional phosphate residues and/ or linking groups, so long as it is able to participate in the protein synthesis reaction, as described above. For example, the cofactor may comprise a polyphosphate that has at least three, four, five, six, seven, or at least eight phosphate groups, and may further contain substitutions, e.g., in the polyphosphate chain side groups or primary linkages, e.g., see U.S. Patent Publication No. 20090018324, incorporated herein by reference in its entirety for all purposes. The cofactor may also or alternatively comprise a linking group that attaches a detectable label to the cofactor, as described elsewhere herein.

In certain embodiments, an initial signal is emitted during delivery of an EF-Tu•GTP/aa-tRNA complex to the A site of the ribosome complex. If the aa-tRNA also comprises a detectable label, signals from both labels are detectable until dissociation of the GTP-bound label, at which time only the aa-tRNA label (and potentially other labels on other aa-tRNAs in the ribosome complex) remain in the observation volume. Similarly, during translocation a labeled GTP bound to EF-G associates with the ribosome and provides the energy for translocation through hydrolysis of the GTP. The signal emitted from the labeled EF-G•GTP is detectable during translocation until dissociation of the GTP-bound label, at which time only the aa-tRNA label(s) will remain in the ribosome complex. The location of the label on the GTP is a factor in the timing of termination of the emission of the detectable signal. If the label is on a phosphate group that is removed during hydrolysis (e.g., a phosphate other than the alpha and beta phosphates), the signal ceases once the hydrolysis of GTP is complete and the released phosphate(s) diffuses away from the reaction site. Alternatively, if the label is on the sugar, guanine base, or a phosphate group that is retained by the elongation factor complex after hydrolysis of the GTP cofactor (e.g., EF-Tu•GDP or EF-G•GDP), the signal ceases once the GDP-containing elongation factor complex is spontaneously released (e.g., upon binding of the aa-tRNA to the A site or translocation of the complex) and diffuses out of the reaction site.

Figure 10:
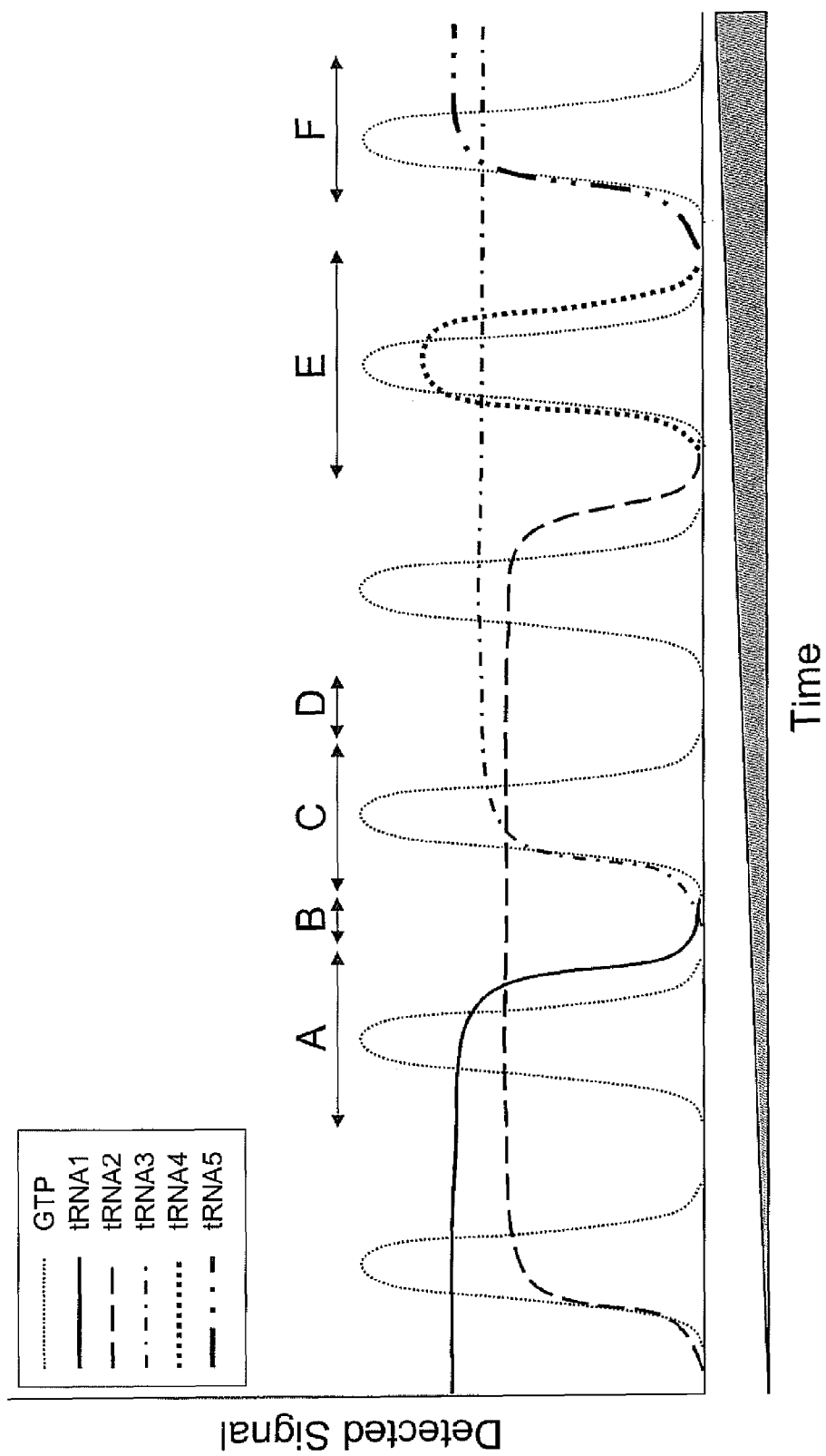
FIG. 10 provides a graphical representation of detectable signal emissions during one embodiment of a protein synthesis reaction in which both GTP and tRNAs comprise detectable labels.

FIG. 10 provides an illustrative example of an embodiment in which both GTP cofactors and tRNAs comprise detectable labels, all of which are optically distinguishable in the reaction. For example, each different label produces a different emission spectrum upon excitation so that detection of the emission unambiguously identifies the molecule from which it originated, e.g., a particular tRNA or GTP. (As such, signal emitted from an EF-Tu•GTP complex is indistinguishable from a signal emitted from an EF-G•GTP complex.) As for FIGS. 7-9 above, FIG. 10 is a graphical representation of detectable signal emissions during the reaction. During period A, EF-G•GTP catalyzes translocation of the ribosome along the mRNA template. In addition to the signal emitted from the labeled GTP, signal is also being emitted from tRNA1 being transferred from the P site to the E site, and tRNA2 being transferred from the A site to the P site. The signal from tRNA1 ends as the molecule is released from the ribosome complex and diffuses out of the observation volume. Following translocation there is no labeled GTP in the observation volume, but signals are detectable from as many as three tRNAs. Period B depicts detectable signals from three tRNAs: one exiting the E site, one occupying the P site, and one entering the A site. In period C. EF-Tu•GTP catalyzes binding of incoming tRNA3 (with its cognate amino acid) to the A site: signal is detectable from the labeled GTP, incoming tRNA3, and tRNA2 in the P site. In period D, only signal from labels on the tRNAs in the P and A sites (tRNA2 and tRNA3) are detectable since the E site is empty.

Period E illustrates a case in which an aa-tRNA brought to the ribosome complex by EF-Tu•GTP is subsequently rejected and dissociates without polypeptide bond formation. Emissions from both the EF-Tu•GTP and tRNA4 are detectable during the "sampling" of the aa-tRNA by the ribosome complex. The signal from the EF-Tu•GTP ends as the elongation factor released from the complex and diffuses away, and shortly thereafter the signal, from tRNA4 also ends due to the rejection of the aa-tRNA by the ribosome. This period can be identified as a sample event due to the similar characteristics of the periods immediately prior to and following the GTP signal. That is, both are characteristic of a period following a translocation event (as shown for period B), and this is indicative that a sampling event occurred. During period F, an EF-Tu•GTP carrying tRNA5 (with its cognate amino acid) associates with the ribosome complex, and the detectable signals from tRNA3 and tRNA5 after dissociation of the GTP label indicate that tRNA5 is binding to the A site and has not been rejected.

In yet further embodiments, GTP cofactors can comprise a FRET donor. In some embodiments, the different FRET acceptors are linked to different aa-tRNA complexes to produce a distinctive and identifiable signal when in the vicinity of the GTP-FRET donor. For example, during elongation a detectable signal is emitted from the EF-Tu•GTP/aa-tRNA complex once it enters the observation volume. As described above for the non-FRET labels, the location of the FRET donor on the GTP (i.e., whether it is cleaved off during hydrolysis) affects the timing of termination of the emission of the detectable signal. Additional FRET acceptors on tRNAs associated with the ribosome complex (e.g., in the P site) may also be excited by the FRET donor on the GTP and produce emission signals that overlap with that of the incoming aa-tRNA. Subsequent peptide bond formation transfers the nascent polypeptide chain on the tRNA in the P site to the aa-tRNA in the A site. Association of EF-G•GTP with the ribosome complex during translocation causes a second detectable signal to be emitted, e.g., from the label linked to the tRNA transferred from the A site to the P site during translocation and/or from a label present on a deacylated-tRNA in the P site prior to translocation (or the E site after translocation). Signal emissions that overlap in time can be analyzed, e.g., comparing various characteristics of their emission spectra, to identify the individual labels and, thereby, identify the two tRNAs. As described above, a plurality of the same label in the ribosome complex can be distinguished at least based on the intensity of the peak(s) in the emission spectrum. Standard statistical analysis of the detected emissions will identify the label(s) generating the detectable signal, and performing this analysis for the sequential emission spectra emitted over the course of a protein synthesis reaction allows reconstruction of the sequence of binding and incorporation events on the ribosome complex, thereby generating sequence information for the resulting polypeptide chain.

Further, the use of labeled GTP is useful for analysis of sampling of aa-tRNAs by the ribosome complex with and without incorporation, providing useful information on the kinetics of such sampling as well as the number of sampling events per incorporation event. Essentially, each sampling event (e.g., aa-tRNA is brought to complex but does not bind, or binds and is subsequently ejected) will produce a signal from the aa-tRNA bound by the labeled EF-G•GTP complex that escorts it to the ribosome complex. The signal from the label on that aa-tRNA will only be reemitted upon translocation if the aa-tRNA participates in the subsequent peptide bond formation. Thus, an aa-tRNA that is sampled but rejected by the ribosome complex will only provide a single detectable signal, while an aa-tRNA that is used to lengthen the polypeptide chain will emit two detectable signals, one at binding and one at translocation. As noted above, FRET donors on EF-Tu that excite multiple FRET acceptors associated with the ribosome complex (e.g., on tRNAs in the A, P, and E sites) can also be used to monitor and further analyze sampling by the ribosome complex.

It is not necessary that aa-tRNAs be differentially labeled in protein synthesis reactions using labeled elongation factors and/or GTP cofactors. A practitioner of the invention may choose to only label one or more elongation factors and/or GTP cofactors in order to monitor various characteristics of a protein synthesis reaction. For example, by labeling only EF-Tu and EF-G and monitoring their association with a synthesizing ribosome complex, one can determine the rate of incorporation and the average number of aa-tRNA sampling event for each incorporation event. Further, addition of various agents (e.g., activators, inhibitors, drug candidates, etc.) can provide insight into the effects of these agents on the characteristics of a protein synthesis reaction.

In some embodiments using labeled elongation factors and/or GTP cofactor, only a subset of aa-tRNAs carry label that is specific for a given amino acid, thereby allowing optical detection of only the amino acids associated with those aa-tRNAs. The number of incorporations of amino acids from unlabeled aa-tRNA complexes that separate each incorporation of an amino acid from a differentially labeled aa-tRNA can be estimated based on the timing of spectral overlap. For example, if EF-G is labeled, overlap of two separate emissions from an EF-G label with an aa-tRNA label indicates that the cognate aa-tRNA is incorporated into the polypeptide chain, and that incorporation occurred immediately prior to the first EF-G label emission that overlapped the aa-tRNA label. By counting the number EF-G label emissions between each incorporation of a known amino acid one can determine the spacing between the known amino acids in the nascent polypeptide chain. One or more aa-tRNAs may be differentially labeled, and the resulting "read" comprising a subset of amino acid incorporations separated by known distances can provide a signature for a polypeptide chain and allow its identification, e.g., by reference to a database of known polypeptide sequences.

In certain preferred embodiments all aa-tRNAs carry some type of detectable label. For example, a subset of tRNAs can carry a label that allows identification the cognate amino acid, e.g., all those with one of a particular set of amino acids of interest, while the remaining aa-tRNAs carry the same detectable label and cannot be optically distinguished from one another. The signal emitted from the EF-G•GTP upon translocation serves as a means of counting the amino acid incorporations between each incorporation of one of the amino acids in the set. In the event that an aa-tRNA that associates with the ribosome but is released prior to incorporation, there will be no signal from the label on EF-G•GTP until a subsequent aa-tRNA associates and participates in peptide bond formation. Therefore, a signal from a labeled EF-G•GTP indicates not only that an amino acid incorporation occurred, but also that the amino acid that was incorporated corresponds to the aa-tRNA detected immediately prior to the EF-G•GTP signal. As described above, the resulting protein sequence read provides a signature for the polypeptide chain, and this can be used for various downstream analyses, e.g., identification of a polypeptide variant or mutant based upon a known sequence of a wild-type polypeptide.

Further, the use of a label that is not constantly present on the ribosome complex is beneficial in various ways, including mitigation of photo-induced damage that could otherwise negatively impact the ongoing reaction. The term "photo-induced damage" generally refers to any direct or indirect impact of illumination, directed or emitted, on one or more reagents in a reaction resulting in a negative impact upon that reaction. For example, the long-lived triplet-state species of many fluorescent dye molecules exhibits a high degree of chemical reactivity that often results in photobleaching and the production of damaging free radicals and reactive intermediates. Since a FRET donor linked to EF-G, EF-Tu, or GTP molecules would be constantly exchanged at each elongation cycle, the problems associated with photobleaching of a stationary FRET donor (e.g., one linked to the ribosome so continually in the reaction site) would be mitigated. Further, the risk of photo-induced damage to other reaction components, in particular those immobilized in the reaction site, is reduced since the potentially damaging emissions of signal from the FRET donor (and, therefore, emission of signal from the corresponding FRET acceptor) are not constant; that is, such emissions are limited to those periods of time during which the FRET donor is present in the reaction site, e.g., during aa-tRNA binding, translocation, or both. A further benefit is realized when using GTP having a FRET label because the resulting GDP is removed from EF-Tu or EF-G and entirely replaced by a new GTP during the recycling of the elongation factor, thereby removing a potentially damaged GTP or FRET donor linked thereto and introducing an undamaged cofactor. Other methods for mitigating photo-induced damage that may be combined with the methods, compositions, and systems of the invention are provided, e.g., in U.S. Ser. No. 61/116,048, 61/139,402, 12/413,226, 61/127,435, and 12/367,411; and in U.S. Patent Pub. No. 20070128133.

Further, in certain preferred embodiments, combinations of various labeling strategies can be used. For example, a quencher near the A site of the ribosome as described for FIG. 3 can be combined with a FRET donor label near the P site of the ribosome. Such a conformation would quench an incoming label, e.g., during the proofreading stage of elongation, and would only allow the detectable period to begin once peptide bond formation and translocation had occurred, thereby removing the FRET acceptor from the quencher and bringing it in close proximity to the FRET donor. Alternatively, a ribosome could comprise a configuration of a FRET donor and one or more quenchers to differentially allow signal to be selectively emitted from one or a combination of A, P, or E sites of the ribosome, e.g., quenching at A and E, but a FRET donor at P, or the FRET donor on EF-G.

In certain embodiments, at least about 2, 4, 6, 8, 10, 12, 14, 16, or 18 different types of aa-tRNAs are individually identifiable during a protein synthesis reaction. In certain embodiments, each different type of aa-tRNA is individually identifiable during a protein synthesis reaction, e.g., due to each comprising a different detectable label. The sequence of amino acid incorporation events is monitored and the resulting sequence "read" provides a sequence of amino acids in the nascent polypeptide strand comprising the order of incorporation of the differentially labeled amino acids. In some embodiments, different detectable labels comprise different chromophores. In some embodiments, fMet-tRNA$^{fMet}$ is also differentially labeled to generate a distinct signal indicating formation of the initiation complex. In other embodiments, different detectable labels can comprise the same chromophores, but in different conformations. For example, two FRET labels, each comprising the same two chromophores, can be configured differently to produce different and distinct emission spectra. Such FRET labels and methods of synthesis and use thereof are provided, e.g., in U.S. Ser. No. 61/164,567, filed Mar. 30, 2009; and U.S. Ser. No. 12/749,859, filed Mar. 30, 2010, the disclosures of which are incorporated herein by reference in their entireties for all purposes.

In some embodiments, not all aa-tRNA types are labeled to be distinguishable from every other type of aa-tRNA in the reaction mixture. For example, in some cases only a subset of aa-tRNA types are differentially labeled with the remaining aa-tRNA types unlabeled. The resulting sequence read provides the order of only the amino acids carried by detectably labeled aa-tRNAs, and this pattern provides valuable sequence characteristics for the nascent polypeptide strand. These sequence characteristics can in sonic cases be used to identify the polypeptide, e.g., in combination with the characteristic amino acid compositions of known proteins. Further, the time between detectable incorporation events can provide some sequence context, e.g., an approximate number of amino acid incorporations between each incorporation of an amino acid carried by a detectably labeled aa-tRNA. Further, having only a portion of aa-tRNAs labeled also helps mitigate photo-induced damage by reducing the total number/amount of aa-tRNA label emissions over the course of the protein synthesis reaction.

In other embodiments, only a subset of aa-tRNA types are differentially labeled with the remaining aa-tRNA types labeled identically. Even if only a small subset of aa-tRNAs are differentially labeled (e.g., from one to five different types), the identity of the protein being synthesized can still be discovered by detecting the unique pattern of incorporation of the amino acids carried by the subset of aa-tRNAs that are differentially labeled. Such a strategy can provide sequence context for the resulting sequence read, e.g., by providing a number of "same-labeled" amino acid incorporations between each of the incorporations of amino acids from the differentially labeled aa-tRNAs. For example, the sequence characteristics provided by detecting incorporation of the amino acids carried by the differentially aa-tRNAs provides both a number of each amino acid and an order of incorporation for them; the sequence characteristics provided by detecting incorporation of the amino acids carried by the identically labeled aa-tRNAs provides a number of incorporation events between each incorporation of an amino acid from a differentially labeled aa-tRNA.

In further embodiments, subsets of aa-tRNAs are labeled identically. The ordinary practitioner can choose subsets of aa-tRNAs for identical or non-identical labeling in any way that provides the desired sequence characteristics for a nascent polypeptide being synthesized. For example, the type of amino acid carried by an aa-tRNA may determine the type of label, with aa-tRNAs carrying amino acids with similar properties identically labeled. In particular, the properties of the R group of the amino acid can be used (e.g., nonpolar and aliphatic, aromatic, uncharged polar, negatively charged, and positively charged) to determine which subsets of aa-tRNAs to label identically.

In still further embodiments, aa-tRNA labeling strategies are used in which the amino acid carried by the labeled aa-tRNA is not necessarily identifiable by the detectable label, but the label retains specificity to the anticodon region of the tRNA regardless of the amino acid used to charge the tRNA. These strategies are useful in various applications, such as where the focus is on aspects of translation that do not depend on the actual sequence of the nascent polypeptide being generated, e.g., ribosome kinetics, the sequence of the polypeptide encoded by the mRNA, or mRNA structure (e.g., nucleotide sequence, secondary or tertiary structure, etc.). For example, a promiscuous tRNA synthetase can be used that is capable of charging all tRNAs with a single, or reduced set, or scrambled set of amino acids, e.g., irrespective of the anticodon sequence of the tRNAs. This would result in aa-tRNAs that have different anticodons capable of interacting with the codon of the mRNA and allowing incorporation of the amino acid they carry into the nascent polypeptide, but the sequence of the resulting polypeptide would not be expected to be that encoded by the mRNA template since it would not necessarily correspond to the anticodon. Alternatively or in addition, non-enzymatic processes can be used to charge multiple different tRNAs with the same amino acid, or subsets of the tRNAs with particular amino acids, or subsets of the tRNAs with subsets of amino acids, and the like. Certain methods for non-enzymatic tRNA charging have been previously described, e.g., in Krzyzaniak, et al. (1994) International Journal of Biological Macromolecules 16(3):153-8, which is incorporated herein by reference in its entirety for all purposes.

In certain embodiments, each different aa-tRNA carries a different and optically distinguishable label, which allows identification of which anticodon interacts with the ribosome during translation. Detection of the series of labels associating with the ribosome during translation is indicative of the anticodon associating with each codon in the mRNA template. The sequence of anticodon interactions provides not only the sequence of the encoded polypeptide, but also provides the sequence of the mRNA, to the extent allowed by the genetic code, and characteristics of the translation reaction can be used to study various aspects of ribosome function, mRNA structure, and the regulation thereof (e.g., in the absence and presence of various agents, conditions, etc.) Of course, wobble base pairing between the anticodon and codon will allow a single anticodon to bind to more than one codon, so the mRNA sequence may not be completely provided, but a nearly complete sequence read is often sufficient for many applications, such as mRNA identification, mRNA template structure determination, and ribosome kinetics.

In some embodiments, the gene for a single tRNA backbone is mutated to change the portion encoding the anticodon region of the resulting tRNA. A set of mutant tRNAs can be generated, each with the same backbone but a different anticodon. Each mutant tRNA is labeled to allow detection of each in the translation reaction. In certain preferred embodiments, mutant tRNAs corresponding to different anticodons are differentially labeled and the sequence of anticodons associating with the mRNA template can be determined and used in further analysis of various aspects of the translation reaction, as further described above. The tRNA backbone can be chosen to confer a particular quality to a plurality of resulting aa-tRNAs, such as ease of labeling and/or charging, e.g., with a single type of amino acid, e.g., by a single type of aa-tRNA synthetase. In some embodiments, more than one tRNA backbone is used to create a set of aa-tRNAs comprising x anticodons and y tRNA backbones, where x>y.

In some embodiments, tRNA isodecoders are used. tRNA isodecoders are sets of tRNAs that have the same anti-codon but different backbone sequences. The mammalian genome contains a couple of hundred tRNA isodecoder genes. Human tRNA isodecoders are further described in the literature, e.g., in Geslain, et al. (2010) J. Mol. Biol. 396:821-831, which is incorporated herein by reference in its entirety for all purposes. Since the structure and sequence of a tRNA has an effect on various characteristics of translation (e.g., rate, error profile, etc.), the set of tRNA isodecoders for each anti-codon can be screened for those that operate best in the translation reactions, e.g., those that are most efficiently used for incorporation or those that are least likely to cause a misincorporation event. Further, the methods provided herein can be used to study the biological importance of tRNA isodecoders. For example, a set of tRNA isodecoders that have the same anticodon could be compared to one another to determine their impact on translation efficiency, kinetics, interaction with accessory proteins or molecules (e.g., EF-Tu), or their interaction with codons containing modified RNA bases. Identification of isodecoders that interact better or worse with such modifications (e.g., RNA N6-methyladenine or RNA pseudo-uridine) may provide insight into their function and purpose in the cell.

In other embodiments, domains may be inserted into the tRNAs to facilitate attachment of labeling moities. Only a few types of nucleobases are typically used for easy and specific labeling, so introducing an artificial sequence into tRNAs (either at the gene or RNA level) in a position that does not interfere with proper function would facilitate labeling of tRNAs that do not naturally carry such nucleobases. Such insertions could be at various terminal or central locations within the tRNA, so long as the ability of the tRNA to be charged, deliver an amino acid to the ribosome, and allow incorporation of the amino acid into the nascent polypeptide in a codon-specific manner is maintained.

In yet further embodiments, a combination of the above strategies for labeling aa-tRNAs can be used. For example, a subset may be unlabeled, a subset may be same-labeled, and a subset may be differentially labeled. As will be appreciated, the particular strategy used by a practitioner of the instant invention will depend on the type of sequence characteristics to be collected during the polypeptide synthesis reaction being monitored. Further, different strategies can be used in different protein sequencing reactions on a given mRNA template, and the reads from each can be combined and analyzed to generate a more complete sequence of the polypeptide synthesized than is provided by a single reaction. For example, a first round that utilizes a first set of four differentially labeled aa-tRNAs (with the rest of the aa-tRNAs unlabeled) is followed by a second round that utilizes a second set of four differentially labeled aa-tRNAs (with the rest of the aa-tRNAs unlabeled), where each of the labeled aa-tRNAs in the second set are different than those in the first set. The results from the two rounds are analyzed and used to construct a "read" that is a combination of the data collected during the first and second rounds. In some embodiments, the two sets of differentially labeled aa-tRNAs share at least one labeled aa-tRNA in common (which may or may not be labeled the same in both sets), and this common aa-tRNA provides a pattern of emission signals that is temporally similar in both rounds, and can therefore be used to orient the reads from each round with the other. Of course, the aa-tRNA sets can comprise any number of differentially labeled aa-tRNAs, and may comprise more than one labeled aa-tRNA common to the sets. Further, any number of aa-tRNA sets can be used for the multiple rounds of translation, and all or a portion of these sets can comprise one or more labeled aa-tRNAs in common.

IV. Optical Confinements

In certain aspects, the methods provide a means for studying protein synthesis in vitro by immobilizing at least one component of a protein synthesis reaction in an optical confinement, labeling at least one other component, and detecting signals from the optical confinement during the protein synthesis reaction. An optical confinement is preferentially configured to provide tight optical confinement so only a small volume of the reaction mixture is observable, i.e., signals can only be detected from a small volume of the reaction mixture. In certain embodiments, optical confinement technologies include zero mode waveguides, total internal reflection microscopy (TIRF), and/or optical waveguides (planar or otherwise configured). For example, in embodiments in which excitation illumination is used to excite chromophore-containing labels, the tight optical confinement allows only a small volume of the reaction mixture to be illuminated, and therefore limits excitation to only those chromophores within that small volume. As such, only the chromophores present in the small illuminated volume are excited and emit signals that are detectable by the optical system. This feature of the invention is useful for reducing the background signal from freely diffusing detectably labeled aa-tRNAs in the reaction mixture, thereby enabling the use of physiological concentrations of these reagents. Some such optical confinements and methods of manufacture and use thereof are described at length in, e.g., U.S. Pat. Nos. 7,302,146. 7,476,503, 7,313,308, 7,315,019, 7,170,050, 6,917,726, 7,013,054, 7,181,122, and 7,292,742; U.S. Patent Publication Nos. 20080128627, 20080152281, 20080152280, 20080226307, and 20100065726; and U.S. Ser. No. 61/312,953, filed Mar. 11, 2010 and 61/306,235, filed Feb. 19, 2010, all of which are incorporated herein by reference in their entireties for all purposes.

Providing such individually resolvable configurations can be accomplished through a number of mechanisms, and typically involves immobilization of at least one component of a ribosome complex at a reaction site. For example, by providing a dilute solution of complexes on a substrate surface suited for immobilization, one will be able to provide individually optically resolvable complexes. (See, e.g., European Patent No. 1105529 to Balasubramanian, et al., the full disclosure of which is incorporated herein by reference in its entirety for all purposes.) Alternatively, one may provide a low density activated surface to which complexes are coupled. (See, e.g., Published International Patent Application No. WO 2007/041394, the full disclosure of which is incorporated herein by reference in its entirety for all purposes). Such individual complexes may be provided on planar substrates or otherwise incorporated into other structures, e.g., zero mode waveguides or waveguide arrays, to facilitate their observation. In preferred embodiments, a substrate comprises at least one optical confinement in which a ribosome complex is immobilized and monitored. The optical confinement is configured to isolate the immobilized ribosome complex from any other ribosome complex immobilized on the substrate, and in particular to isolate any detectable signals emitted from the optical confinement from any other signals emitted from any other optical confinements on the substrate. Such isolation allows the practitioner of the instant invention to unambiguously assign a detected signal to a single optical confinement on the substrate, and therefore to a single ribosome complex (and to a single mRNA template in the complex) on the substrate.

The immobilization of a ribosome complex can be engineered in various ways. For example, the ribosome itself may be attached to the substrate at a reaction site. In other embodiments, the mRNA template may be attached to the substrate at a reaction site. One skilled in the art will appreciate that there are many ways of immobilizing nucleic acids, proteins, and molecular complexes onto an optical confinement, whether covalently or non-covalently, via a linker moiety, or tethering them to an immobilized moiety. These methods are well known in the field of solid phase synthesis and micro-arrays (Beier et al., Nucleic Acids Res. 27:1970-1-977 (1999)). Non-limiting exemplary binding moieties for attaching compounds, e.g., nucleic acids, enzymes, molecular complexes, to a solid support include streptavidin or avidin/biotin linkages, carbamate linkages, ester linkages, amide, thiolester, (N)-functionalized thiourea, functionalized maleimide, amino, disulfide, amide, hydrazone linkages, among others. Antibodies that specifically bind to the target nucleic acids or polymerases can also be employed as the binding moieties. In addition, a silyl moiety can be attached to a nucleic acid directly to a substrate such as glass using methods known in the art. In certain embodiments, a ribosome can be immobilized at a reaction site via a linkage to one of the ribosomal proteins or rRNA molecules. For example, an oligonucleotide that comprises an immobilization tag (e.g., is biotinylated) and is complementary to a portion of an rRNA molecule (e.g., loop region) can be immobilized at a reaction site. Subsequent hybridization to the complementary rRNA molecule in the ribosome effectively immobilizes the ribosome at the reaction site. Similarly, an oligonucleotide that comprises an immobilization tag and is complementary to a portion of a template molecule can be immobilized at a reaction site and hybridized to the template, thereby immobilizing the template at the reaction site. For example, an mRNA template can be immobilized onto a reaction site (e.g., within an optical confinement) by attaching a primer comprising a poly-T terminal portion at the reaction site, the poly-T terminal portion capable of hybridizing with a poly-A tail of an mRNA template, thereby immobilizing it in a position suitable for association with and translation by a ribosome. Alternatively, an adaptor comprising an, immobilization tag can be ligated to a template or rRNA molecule and immobilized at a reaction site, thereby immobilizing the template or rRNA molecule, or a complex comprising the same. In certain preferred embodiments, the ribosome is first attached to the reaction site in a position suitable for the mRNA template to move relative to the ribosome. In certain preferred embodiments, the immobilized ribosome complex contains a single ribosome and a single mRNA molecule.

Where desired, the ribosomes may be modified to contain one or more epitopes such as Myc, HA (derived from influenza virus hemagglutinin), poly-histadines, and/or FLAG, for which specific antibodies are available commercially. In addition, the ribosomes can be modified to contain heterologous domains such as glutathione S-transferase (GST), maltose-binding protein (MBP), specific binding peptide regions (see e.g., U.S. Pat. Nos. 5,723,584, 5,874,239 and 5,932,433), or the Fc portion of an immunoglobulin. The respective binding agents for these domains, namely glutathione, maltose, and antibodies directed to the Fc portion of an immunoglobulin, are available and can be used to coat the surface of an optical confinement of the present invention.

The binding moieties or agents of either the ribosomes or the template mRNAs they immobilize can be applied to the support by conventional chemical techniques which are well known in the art. In general, these procedures can involve standard chemical surface modifications of a support, incubation of the support at different temperature levels in different media comprising the binding moieties or agents, and possible subsequent steps of washing and cleaning.

In some embodiments, a substrate comprising an array of reaction sites is used to monitor multiple biological reactions, each taking place at a single one of the reaction sites. Various means of loading multiple biological reactions onto an arrayed substrate are known to those of ordinary skill in the art and are described further, e.g., in U.S. Ser. No. 61/072,641, incorporated herein by reference in its entirety for all purposes. For example, basic approaches include: creating a single binding site for a reaction component at the reaction site; removing excess binding sites at the reaction site via catalytic or secondary binding methods; adjusting the size or charge of the reaction component to be immobilized; packaging or binding the reaction component within (or on) a particle (e.g., within a viral capsid), where a single such particle fits into the relevant reaction site (due to size or charge of the particle and/or observation volume); using non-diffusion limited loading; controllably loading the reaction component (e.g., using microfluidic or optical or electrical control); sizing or selecting charges in the reaction sites/observation volumes (e.g., the sizes of optical confinements in an array) to control which reaction components will fit (spatially or electrostatically) into which reaction sites/observation volumes; iterative loading of reaction components, e.g., by masking active sites between loading cycles; enriching the activity of the reaction components that are loaded; using self-assembling nucleic acids to sterically control loading; using ribosome display to control loading and provide a base for screening; adjusting the size of the reaction site/observation volume; and many others. Such methods and compositions provide for the possibility of completely loading single-molecule array reaction sites (instead of about 30% of such sites as occurs in "Poisson limited" loading methods) with single reaction components (e.g., molecular complexes).

The optical confinements can be further tailored in various ways for optimal confinement of a protein synthesis reaction. In particular, the size, shape, and composition of the optical confinement can be specifically designed for containment of a ribosome and for the particular label and illumination scheme used.

Figure 11:
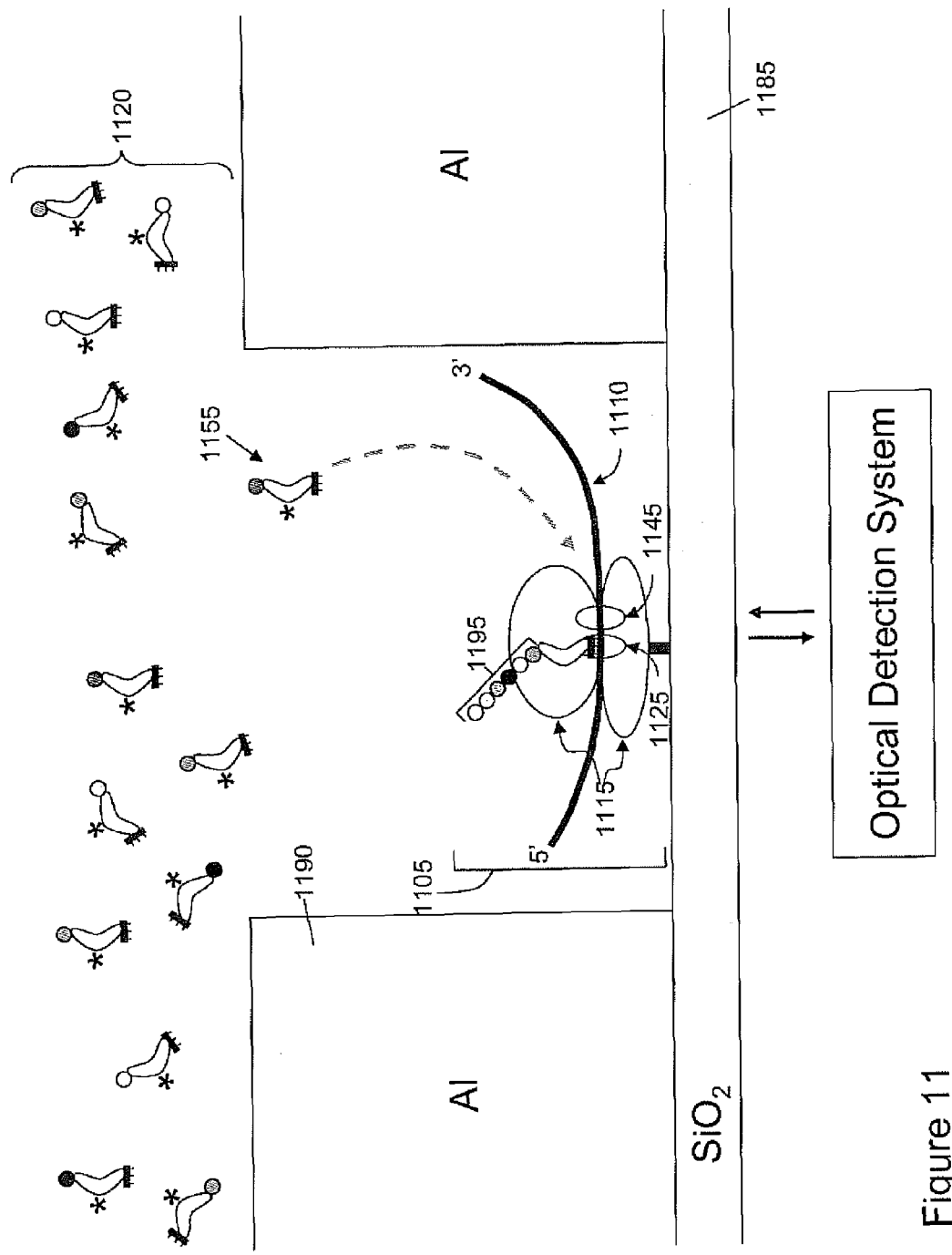
FIG. 11 provides an illustrative example of a ribosome translating an mRNA to produce a nascent polypeptide chain within a particular embodiment of an optical confinement.

FIG. 11 provides an illustrative example of a ribosome translating an mRNA to produce a nascent polypeptide chain within a particular embodiment of an optical confinement. The optical confinement in this example is a zero mode waveguide comprising a silicon dioxide solid surface (1185) overlaid with an aluminum masking layer (1190) through which pores have been created to serve as physical barriers to isolate a single ribosome complex (1105). Free labeled aa-tRNAs (1120) are provided in a reaction mixture comprising other components required for in vitro protein synthesis, e.g., elongation factors, cofactors, buffers, salts, etc. A labeled aa-tRNA (1155) comprising an anticodon complementary to a codon of the mRNA template (1110) that is in the A site (1145) of an immobilized ribosome (1115) will associate with ribosome complex (1105), and detection of this association via an optical detection system is indicative of the identity of the cognate amino acid incorporated into the nascent polypeptide chain (1195).

V. Systems

The invention also provides systems that are used in conjunction with the compositions and methods of the invention in order to provide for real-time single-molecule detection of protein synthesis reactions. In particular, such systems typically include the reagent systems described herein, in conjunction with an analytical system, e.g., for detecting data from those reagent systems. In certain preferred embodiments, protein synthesis reactions are monitored using an optical system capable of detecting and/or monitoring interactions between reactants at the single-molecule level. For example, such an optical system can achieve these functions by first generating and transmitting an incident wavelength to the reactants, followed by collecting and analyzing the optical signals from the reactants. Such systems typically employ an optical train that directs signals from the reactions to a detector, and in certain embodiments in which a plurality of reactions is disposed on a solid surface, such systems typically direct signals from the solid surface (e.g., array of confinements) onto different locations of an array-based detector to simultaneously detect multiple different optical signals from each of multiple different reactions. In particular, the optical trains typically include optical gratings or wedge prisms to simultaneously direct and separate signals having differing spectral characteristics from each confinement in an array to different locations on an array based detector, e.g., a CCD, and may also comprise additional optical transmission elements and optical reflection elements.

An optical system applicable for use with the present invention preferably comprises at least an excitation source and a photon detector. The excitation source generates and transmits incident light used to optically excite the reactants in the reaction. Depending on the intended application, the source of the incident light can be a laser, laser diode, a light-emitting diode (LED), a ultra-violet light bulb, and/or a white light source. Further, the excitation light may be evanescent light, e.g., as in total internal reflection microscopy, certain types of waveguides that carry light to a reaction site (see, e.g., U.S. Application Pub. Nos. 20080128627, 20080152281, and 200801552280), or zero mode waveguides, described below. Where desired, more than one source can be employed simultaneously. The use of multiple sources is particularly desirable in applications that employ multiple different reagent compounds having differing excitation spectra, consequently allowing detection of more than one fluorescent signal to track the interactions of more than one or one type of molecules simultaneously (e.g., multiple types of differentially labeled aa-tRNAs). A wide variety of photon detectors or detector arrays are available in the art. Representative detectors include but are not limited to an optical reader, a high-efficiency photon detection system, a photodiode (e.g. avalanche photo diodes (APD)), a camera, a charge-coupled device (CCD), an electron-multiplying charge-coupled device (EMCCD), an intensified charge coupled device (ICCD), and a confocal microscope equipped with any of the foregoing detectors. For example, in some embodiments an optical train includes a fluorescence microscope capable of resolving fluorescent signals from individual sequencing complexes. Where desired, the subject arrays of optical confinements contain various alignment aides or keys to facilitate a proper spatial placement of the optical confinement and the excitation sources, the photon detectors, or the optical train as described below.

The subject optical system may also include an optical train whose function can be manifold and may comprise one or more optical transmission or reflection elements. Such optical trains preferably encompass a variety of optical devices that channel light from one location to another in either an altered or unaltered state. First, the optical train collects and/or directs the incident wavelength to the reaction site (e.g., optical confinement). Second, it transmits and/or directs the optical signals emitted from the reactants to the photon detector. Third, it may select and/or modify the optical properties of the incident wavelengths or the emitted wavelengths from the reactants. Illustrative examples of such optical transmission or reflection elements are diffraction gratings, arrayed waveguide gratings (AWG), optical fibers, optical switches, mirrors (including dichroic mirrors), lenses (including microlenses, nanolenses, objective lenses, imaging lenses, and the like), collimators, optical attenuators, filters (e.g., polarization or dichroic filters), prisms, wavelength filters (low-pass, band-pass, or high-pass), planar waveguides, wave-plates, delay lines, and any other devices that guide the transmission of light through proper refractive indices and geometries. One example of a particularly preferred optical train is described in U.S. Patent Pub. No. 20070036511, filed Aug. 11, 2005, and incorporated by reference herein in its entirety for all purposes.

In a preferred embodiment, a reaction site (e.g., optical confinement) containing a reaction of interest is operatively coupled to a photon detector. The reaction site and the respective detector can be spatially aligned (e.g., 1:1 mapping) to permit an efficient collection of optical signals from the reactants. In certain preferred embodiments, a reaction substrate is disposed upon a translation stage, which is typically coupled to appropriate robotics to provide lateral translation of the substrate in two dimensions over a fixed optical train. Alternative embodiments could couple the translation system to the optical train to move that aspect of the system relative to the substrate. For example, a translation stage provides a means of removing a reaction substrate (or a portion thereof) out of the path of illumination to create a non-illuminated period for the reaction substrate (or a portion thereof), and returning the substrate at a later time to initiate a subsequent illuminated period. An exemplary embodiment is provided in U.S. Patent Pub. No. 20070161017, filed Dec. 1, 2006.

In particularly preferred aspects, such systems include arrays of reaction regions, e.g., zero mode waveguide arrays, that are illuminated by the system, in order to detect signals (e.g., fluorescent signals) therefrom, that are in conjunction with analytical reactions being carried out within each reaction region. Each individual reaction region can be operatively coupled to a respective microlens or a nanolens, preferably spatially aligned to optimize the signal collection efficiency. Alternatively, a combination of an objective lens, a spectral filter set or prism for resolving signals of different wavelengths, and an imaging lens can be used in an optical train, to direct optical signals from each confinement to an array detector, e.g., a CCD, and concurrently separate signals from each different confinement into multiple constituent signal elements, e.g., different wavelength spectra, that correspond to different reaction events occurring within each confinement. In preferred embodiments, the setup further comprises means to control illumination of each confinement, and such means may be a feature of the optical system or may be found elsewhere is the system, e.g., as a mask positioned over an array of confinements. Detailed descriptions of such optical systems are provided, e.g., in U.S. Patent Pub. No. 20060063264, filed Sep. 16, 2005, which is incorporated herein by reference in its entirety for all purposes.

The systems of the invention also typically include information processors or computers operably coupled to the detection portions of the systems, in order to store the signal data obtained from the detector(s) on a computer readable medium, e.g., hard disk, CD, DVD or other optical medium, flash memory device, or the like. For purposes of this aspect of the invention, such operable connection provides for the electronic transfer of data from the detection system to the processor for subsequent analysis and conversion. Operable connections may be accomplished through any of a variety of well known computer networking or connecting methods, e.g., Firewire®, USB connections, wireless connections, WAN or LAN connections, or other connections that preferably include high data transfer rates. The computers also typically include software that analyzes the raw signal data, identifies signal pulses that are likely associated with incorporation events, and identifies bases incorporated during the sequencing reaction, in order to convert or transform the raw signal data into user interpretable sequence data (see, e.g., Published U.S. Patent Application No. 2009-0024331, the full disclosure of which is incorporated herein by reference in its entirety for all purposes).

Exemplary systems are described in detail in, e.g., U.S. patent application Ser. No. 11/901,273, filed Sep. 14, 2007 and U.S. patent application Ser. No. 12/134,186, filed Jun. 5, 2008, the full disclosures of which are incorporated herein by reference in their entirety for all purposes.

Further, the invention provides data processing systems for transforming polypeptide sequence read data into consensus sequence data. In certain embodiments, the data processing systems include machines for generating polypeptide sequence read data by ribosome-mediated translation of a template mRNA molecule. The polypeptide sequence read data generated is representative of the amino acid sequence of the nascent polypeptide chain synthesized by a ribosome translocating along an mRNA template only to the extent that a given sequencing technology is able to generate such data, and so may not be identical to the actual sequence of the nascent polypeptide molecule. For example, it may contain a deletion or a different amino acid at a given position as compared to the actual sequence of the polypeptide, e.g., when an amino acid incorporation is missed or incorrectly determined, respectively. As such, it is beneficial to generate redundant polypeptide sequence read data, and to transform the redundant polypeptide sequence read data into consensus polypeptide sequence data that is generally more representative of the actual sequence of the polypeptide molecule than polypeptide sequence read data from a single read of the polypeptide molecule. Redundant polypeptide sequence read data comprises multiple reads, each of which includes at least a portion of polypeptide sequence read that overlaps with at least a portion of at least one other of the multiple polypeptide sequence reads. As such, the multiple reads need not all overlap with one another, and a first subset may overlap for a different portion of the polypeptide sequence than does a second subset. Such redundant sequence read data can be generated by various methods, including repeated synthesis of polypeptides from a single mRNA template, synthesis of polypeptides from multiple identical mRNA templates, or a combination thereof.

In another aspect, the data processing systems can include software and algorithm implementations provided herein, e.g. those configured to transform redundant polypeptide sequence read data into consensus polypeptide sequence data, which, as noted above, is generally more representative of the actual sequence of the nascent polypeptide molecule than polypeptide sequence read data from a single read of a single polypeptide molecule. Further, the transformation of the redundant polypeptide sequence read data into consensus polypeptide sequence data identifies and negates some or all of the single-read variation between the multiple reads in the redundant polypeptide sequence read data. As such, the transformation provides a representation of the actual amino acid sequence of the nascent polypeptide encoded by the mRNA template that is more accurate than a representation based on a single read.

Various methods and algorithms for data transformation employ data analysis techniques that are familiar in a number of technical fields, and are generally referred to herein as statistical analysis. For clarity of description, details of known techniques are not provided herein. These techniques are discussed in a number of available reference works, such as those provided in U.S. Patent Publication No. 20090024331 and U.S. Ser. No. 61/116,439, filed Nov. 20, 2008, the disclosures of which are incorporated herein by reference in their entireties for all purposes.

The software and algorithm implementations provided herein are preferably machine-implemented methods, e.g., carried out on a machine comprising computer-readable medium configured to carry out various aspects of the methods herein. For example, the computer-readable medium preferably comprises at least one or more of the following: a) a user interface; b) memory for storing redundant sequence read data; c) memory storing software-implemented instructions for carrying out the algorithms for transforming redundant sequence read data into consensus sequence data; d) a processor for executing the instructions; e) software for recording the results of the transformation into memory; and f) memory for recordation and storage of the resulting consensus sequence read data. In preferred embodiments, the user interface is used by the practitioner to manage various aspects of the machine, e.g., to direct the machine to carry out the various steps in the transformation of redundant sequence read data into consensus sequence data, recordation of the results of the transformation, and management of the consensus sequence data stored in memory.

As such, in preferred embodiments, the methods further comprise a transformation of the computer-readable medium by recordation of the redundant sequence read data and/or the consensus sequence data generated by the methods. Further, the computer-readable medium may comprise software for providing a graphical representation of the redundant sequence read data and/or the consensus sequence read data, and the graphical representation may be provided, e.g., in soft-copy (e.g., on an electronic display) and/or hard-copy (e.g., on a print-out) form.

The invention also provides a computer program product comprising a computer-readable medium having a computer-readable program code embodied therein, the computer readable program code adapted to implement one or more of the methods described herein, and optionally also providing storage for the results of the methods of the invention. In certain preferred embodiments, the computer program product comprises the computer-readable medium described above.

In another aspect, the invention provides data processing systems for transforming sequence read data from one or more sequencing reactions into consensus sequence data representative of an actual sequence of one or more template nucleic acids analyzed in the one or more sequencing reactions. Such data processing systems typically comprise a computer processor for processing the sequence read data according to the steps and methods described herein, and computer usable medium for storage of the initial sequence read data and/or the results of one or more steps of the transformation (e.g., the consensus sequence data), such as the computer-readable medium described above.

Figure 12:
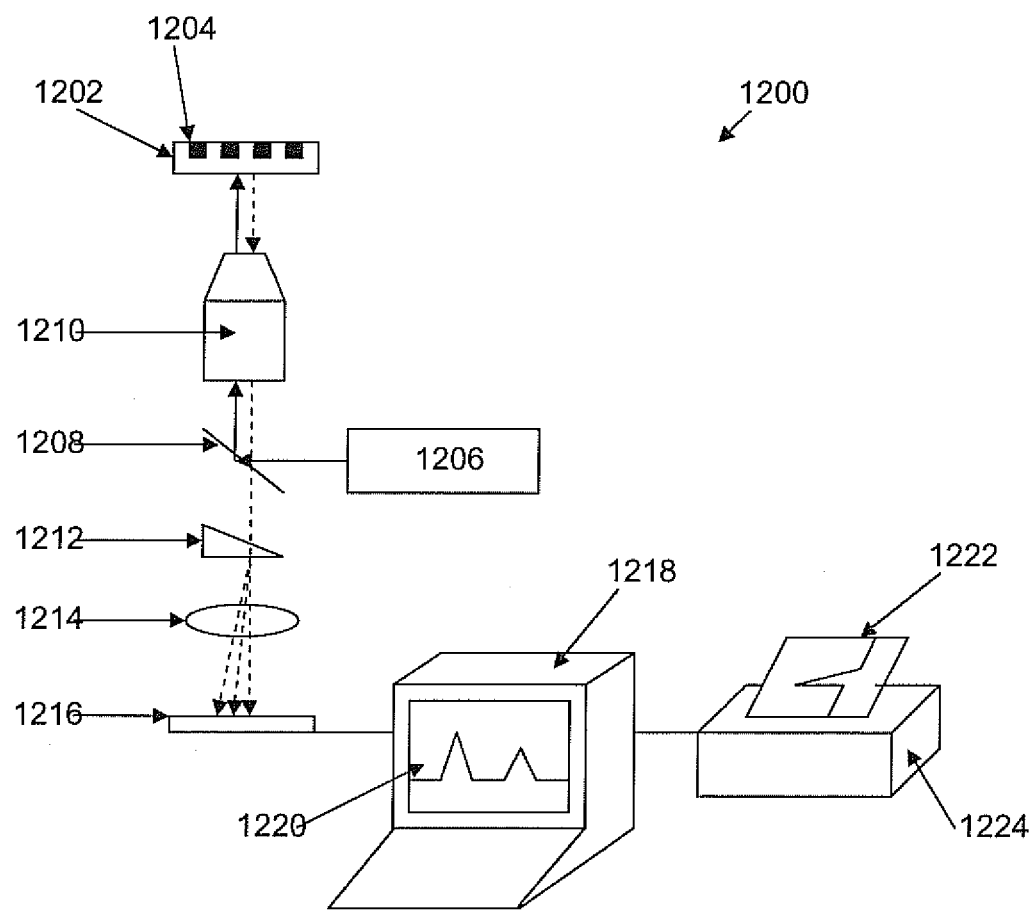
FIG. 12 schematically illustrates one embodiment of a system for use with the methods, devices, and systems of the invention.

As shown in FIG. 12, the system 1200 includes a substrate 1202 that includes a plurality of discrete sources of chromophore emission signals, e.g., an array of zero mode waveguides 1204. An excitation illumination source, e.g., laser 1206, is provided in the system and is positioned to direct excitation radiation at the various signal sources. This is typically done by directing excitation radiation at or through appropriate optical components, e.g., dichroic 1208 and objective lens 1210, that direct the excitation radiation at the substrate 1202, and particularly the signal sources 1204. Emitted signals from the sources 1204 are then collected by the optical components, e.g., objective 1210, and passed through additional optical elements, e.g., dichroic 1208, prism 1212 and lens 1214, until they are directed to and impinge upon an optical detection system, e.g., detector array 1216. The signals are then detected by detector array 1216, and the data from that detection is transmitted to an appropriate data processing system, e.g., computer 1218, where the data is subjected to interpretation, analysis, and ultimately presented in a user ready format, e.g., on display 1220, or printout 1222, from printer 1224. As will be appreciated, a variety of modifications may be made to such systems, including, for example, the use of multiplexing components to direct multiple discrete beams at different locations on the substrate, the use of spatial filter components, such as confocal masks, to filter out-of focus components, beam shaping elements to modify the spot configuration incident upon the substrates, and the like (See, e.g., Published U.S. Patent Application Nos. 2007/0036511 and 2007/095119, and U.S. patent application Ser. No. 11/901,273, all of which are incorporated herein by reference in their entireties for all purposes.)

VI. Exemplary Applications

In certain aspects, the methods, compositions, and systems provided herein are particularly useful for detection and identification of various types of sequence characteristics of a polypeptide being synthesized. For example, the sequence can be compared to a known wild-type protein sequence or to polypeptide sequences from other cell types, tissues, or individuals (e.g., of the same or different species) to identify mutations and variations. For example, by analyzing (e.g., comparing) polypeptide sequences synthesized from mRNAs collected from different individuals, one can identify differences in the proteins being expressed in the cells, tissue, or organs of the individuals. This information can be useful in population studies, genealogical studies, evolutionary history studies, forensics, and the like. Further, the methods can be used to identify differences in protein synthesis in disease tissue as compared to non-disease tissue. For example, various mutations occur within cancer cells that can result in mutant proteins, so comparison of polypeptides generated from mRNAs collected from cancer cells with mRNAs collected from non-cancerous cells can provide valuable insight into the kinds of mutations that provide a biological basis for the development of a malignant neoplasm. Further, unlike analysis at the DNA level, the mRNAs represent genes that are being expressed and are therefore more likely to be directly involved in the ongoing cellular processes in the cells at the time of mRNA collection. As such, the methods may provide a more directed approach to finding protein variants relevant to the function of a particular cell, tissue, disease process, etc. at a particular time, e.g., during differentiation, a particular stage of the cell cycle, or under a given set of conditions. For example, a tissue culture may be treated in various ways, e.g., by varying nutrients in the culture, temperature of the culture, pH of the culture, and the like. For each treatment, mRNA can be extracted from the culture and separately subjected to translation. The resulting polypeptide sequences can be compared to determine how mRNA expression in the cells changes in response to the various treatments. Tissue cultures having different types of mutations can also be tested to look for differences in transcriptional response to the various treatments that may be attributable to the presence of the mutations.

The methods and systems herein can also be used for detection and identification of various types of sequence characteristics of an mRNA template. For example, from a polypeptide sequence identified in accordance with the methods and compositions provided herein one can use the genetic code to determine the set of mRNA sequences that could have encoded the polypeptide. (Due to the degeneracy of the genetic code, a plurality of possible mRNA template sequences will typically be generated from such an analysis.) If the sequence of the DNA from which the mRNA template was transcribed is known, the sequence of the mRNA template can generally be unambiguously determined based on complementarity, and the initiation and termination sites in the original DNA molecule can be determined, even in cases in which splicing of the mRNA occurred prior to translation. In fact, the methods can be useful for mapping splice sites and identifying mRNA splice variants, as well. Further, comparison of the mRNA template sequence(s) determined from the polypeptide sequence to wild-type mRNA sequences for the same gene can also be used to identify missense or nonsense mutations in the original DNA molecule. As described above for the polypeptide sequences, the mRNA sequences generated by the instant invention can be used for further analysis, including but not limited to studies of population structure, geneology, evolutionary history, forensics, disease processes, etc.

In certain aspects, the methods can be used to screen the effects of changes in the mRNA sequence (e.g., due to mutations in the encoding DNA sequence) on subsequent translation, including ribosomal kinetics, the functionality of the resulting polypeptide, and/or other characteristics of translation reactions. In certain embodiments, different versions or mutants of a given mRNA are separately translated. Metrics from the translation reaction and/or analysis of the resulting polypeptide are generated and analyzed. Differences in various aspects of the analyses are used to identify particular regions in the mRNA that impact these aspects. For example, a single-base change at a given position in the mRNA may be found to enhance, inhibit, or truncate translation of the mRNA molecule. Such changes can result in production of more, less, or mutant and possibly nonfunctional polypeptides. As such, this would not only help to identify mutations that cause a polypeptide having an altered structure, but also the more subtle aspects of increased or decrease expression of an otherwise unaltered polypeptide. For example, an altered codon in the mRNA may still code for the same polypeptide as the unaltered codon, but due to other factors, such as codon usage bias or efficiency differences of the ribosome at the altered codon as compared to efficiency at the unaltered codon.

In related aspects, the methods can facilitate the further analysis of a newly synthesized polypeptide, e.g., by specifically immobilizing the polypeptide within the reaction site and subjecting it to various assays. For example a tag can be engineered into the mRNA template such that the resulting polypeptide contains a tag that allows capture of the polypeptide for subsequent analysis. In certain embodiments, a pool of mRNAs is translated in a plurality of separate ribosomes, e.g., in an array, and the polypeptides generated are immobilized and used to screen one or more agents for binding to the polypeptide. The pool of mRNAs may be specifically selected to allow generation of an array comprising a known set of proteins, or the pool of mRNAs may be unknown to allow generation of an array comprising an unknown set of proteins. The sequence of the polypeptides derived from observation of the single-molecule translation reactions allows identification of the specific polypeptide sequences to which the subsequently added agent(s) bind. In certain embodiments, binding of agents to the nascent polypeptide can be monitored under various reaction conditions (e.g., temperature, pH, ion concentrations, agent concentrations, number of different agents present, etc.) to study different aspects of the interaction, e.g., affinity, on-off rate, competition between multiple agents, etc. Methods for detection of binding at the single molecular complex level are described further in U.S. patent application Ser. No. 12/814,075, filed Jun. 11, 2010, the disclosure of which is incorporated herein by reference in its entirety for all purposes.

As noted elsewhere herein, the methods can be used to derive structure information for an mRNA template. mRNA structure includes not only nucleobases sequence information, but also other structural characteristics including secondary and tertiary structures. In certain embodiments in which the label on an aa-tRNA complex is indicative of its anticodon, a time sequence of anticodons associating with the ribosome is generated by observation of a single ribosome translating a single mRNA template. The sequence of anticodons is indicative of the sequence of codons in the mRNA template encoding a polypeptide (at least as far as wobble base pairing will permit). Wobble base pairing between the anticodon and codon will allow a single anticodon to bind to more than one codon, so the mRNA sequence may not be completely provided, but a nearly complete sequence read is often sufficient for many applications. Alternatively or additionally, the methods can be used to map the secondary or tertiary structure of an mRNA template during translation, e.g., to identify potential translational regulatory motifs such as hairpin structures, pseudoknots, stem-loops, etc. Such structures in an mRNA template can cause a change in the activity of a ribosome, e.g., a pause or stall, and this change can be detected during real-time single-molecule analysis. Further, the methods can be used to detect modified and/or unnatural nucleobases in an mRNA template. For example, identifiable (e.g., differentially labeled) aa-tRNAs having anticodons capable of interacting with the modified/unnatural base can be used. In certain embodiments, they facilitate bypass of the modified/unnatural base by providing an amino acid for incorporation into the nascent polypeptide chain. In other embodiments, modified/unnatural bases are detectable through analysis of ribosome activity during translation, e.g., pausing or stalling. In certain embodiments, mRNA structure is characterized for all protein coding genes, and in other embodiments genes with a particular therapeutic potential are specifically analyzed. Where mRNA structure(s) are found to characterize a disease-related mRNA, therapeutics can be developed to target the structure, e.g., to inhibit translation of the disease-related mRNA. Some methods of detecting modified/unnatural bases and secondary or tertiary structures in nucleic acid templates being processed by polymerases are also applicable to the methods herein, and are described in detail in U.S. Ser. No. 12/635,618, filed Dec. 10, 2009, and incorporated herein by reference in its entirety for all purposes.

Various screening methods are contemplated that use the real-time single-molecule translation methods described herein. Such methods are useful for assessing the ability of various agents to inhibit or stimulate translation of a given mRNA, e.g., through interaction with the translational complex or effects on stability of the mRNA template. Further, in an arrayed format the methods could be used to assess the ability of a given agent or mixture of agents to impact translation for a population of mRNA templates. Of particular interest are agents including, but are not limited to, RNA-based probes (e.g., miRNA, siRNA, antisense RNA, etc.), small molecules (e.g., drug candidates), biologic drug candidates, and the like. Identification of a plurality of mRNAs whose translation is impacted by binding of a given agent or mixture of agents can also aid in identification of broad networks of gene activity that can be activated or suppressed by the agent. Information about such networks is valuable in understanding how they operate in an organism, and can be especially useful where they control or are otherwise involved in disease or drug response traits. For example, genes in a newly identified network may be further tested as drug targets for a given disease phenotype. Further, where networks of gene activity are known, mRNAs from a single network can be pooled and subjected to treatment with various agents to determine their impact on various characteristics of protein synthesis reactions, e.g., efficiency and other kinetic parameters, and therefore on the network itself. For example, if a network is known to be involved in a particular disease trait or drug response, study of translational characteristics under a variety of conditions (e.g., in the presence of various different agents or combinations thereof) can provide insight to help identify mRNAs within the network that are either potential drug targets or involved in the drug response. Further, the effects of a single agent on different networks can be analyzed to identify condition-dependent differential control of the different networks.

Screening methods are also provided for analysis of different mRNAs of genes, e.g., to build an understanding of the ways in which different mRNA isoforms are translationally regulated. For example, by introducing synthetic mRNAs in which the 3'- and 5'-UTRs have been systematically altered and then testing them in real-time single-molecule translation assays, one can identify and map regions important for accurate translation of a given isoforms and/or for driving generation of less functional forms of a protein. For example, certain isoforms are predisposed to frameshifts during translation that lead to a nonsense proteins or proteins that can't fold properly, so assays that allow identification of these isoforms are useful not only for diagnostic applications, but also for developing therapeutics to block or inhibit their translation.

For example, the methods, compositions, and systems described herein can also be used in diagnostic applications for disorders that result from protein synthesis defects. Mutations in 5' UTRs of certain mRNAs can effect translation of those mRNAs and therefore alter the expression of the encoded protein. For example, hereditary hyperferritinaemia is caused by excessive production of ferritin due to mutations in the 5' UTR of the ferritin mRNA that abrogate normal suppression of ferritin production when iron levels are low. Diagnosis of this condition could be performed by monitoring translation of ferritin mRNA under high and low iron conditions, where the lack of a difference in ferritin polypeptide production under these conditions is indicative of the presence of one or more hyperferritinaemia mutations. Further, various agents could be added to the translation of mRNAs comprising one or more hyperferritinaemia mutations to screen for an agent that restores suppression of translation in low iron conditions. Candidate agents so identified can be further screened against total cellular mRNA to identify if translation of other mRNAs would also be effected by such treatment.

In other aspects, the methods, compositions, and systems can be used to test the impact of changes to the translational environment (e.g., via addition of various agents and/or changes to one or more reaction conditions) on protein synthesis. Various aspects of protein synthesis may be examined, e.g., rate of amino acid incorporation, error profile, processivity of translation, conformational changes within the ribosome complex, and the like.

In some embodiments, the agents are mutant versions of the wild-type translational machinery or other factors required for translation, e.g., ribosomal proteins and/or RNAs, elongation factors, initiation factors, termination factors, release factors, nucleotide cofactors, tRNAs, aa-tRNA synthetases, mRNA variants, etc. For example, certain mutations can suppress ribosomal proofreading to allow incorporation of amino acids and thereby permit "read through" of premature stop codons caused by nonsense mutations, thus facilitating synthesis of full-length protein from an mRNA template that would otherwise have encoded a truncated and potentially non functional protein. In certain embodiments, the agents are exogenous substances, e.g., drug candidates that can be tested to determine their impact on wild-type and/or mutant ribosomes. In some embodiments, the agents are noncoding RNAs (e.g., siRNAs). For example, a library of expressed siRNAs can be tested for their effect on translation on an array comprising a plurality of identical immobilized protein synthesis reactions. Alternatively, a specific siRNA of interest can be tested on an array comprising multiple different polypeptides being synthesized and monitored independently in real time, e.g., to determine the specificity of the siRNA for a particular polypeptide or set thereof. In some embodiments, one or more reaction conditions are varied, e.g., pH, temperature, salt concentration, concentration of various components of the transcriptional machinery (e.g., template mRNA, cofactors, initiation factors, elongation factors, termination factors, release factors, and ribosome components), and the like. Such methods are useful in qualitative, quantitative, and competitive assays, e.g., in screening antibiotics, optimization of mRNA sequence for translation, optimization of translation reaction conditions, and the like. Screening assays to identify new antibiotics are of particular interest given that certain antibiotics are known to target bacterial ribosome function. For example, the methods herein are useful to identify drugs that inhibit bacterial ribosome function but do not affect eukaryotic ribosome function by comparing their impact on both bacterial and eukaryotic protein synthesis reactions.

Likewise, mutations in the EIF2AK3 gene can cause Wolcott-Pallison syndrome, a rare autosomal recessive disorder that results in infantile-onset diabetes mellitus (DM) due to impaired production of the PEAK protein during fetal and early neonatal periods. As such, prenatal diagnosis and treatment would greatly benefit patients suffering from this disorder, potentially preventing the early development of DM and at least allowing earlier treatment once an affected child is born. By performing translation assays on mRNAs from fetal cells, one could determine if the translation defect is present. Further screening assays could test various agents for compensatory effects, potentially identifying treatments to mitigate or reverse the effects of the disorder.

In certain aspects, the activity of different ribosome structures can be studied by the methods herein. For example, certain antibiotics function by blocking or inhibiting the ribosomal machinery in bacterial cells. Studying translation in strains of bacteria that have developed resistance to such antibiotics can provide insight into the types of changes made to the ribosomal machinery that cause it to no longer be sensitive to the antibiotic, and further to treat the "resistant" ribosome with other agents or drugs to study their effects and potentially identify alternative antibiotic treatment effective on the resistant strain.

In yet further aspects, methods for screening agents for binding to a nascent polypeptide being produced are provided. In certain embodiments, a polypeptide produced in a real-time single-molecule translation reaction is exposed to one or more agents during synthesis. The one or more agents are detectable, and preferably differentially, labeled and therefore detectable upon binding to the nascent polypeptide. Because the incorporation of amino acids into the polypeptide is being detected during the synthesis reaction, the protein sequence is determined and can be used to determine a region of the polypeptide to which such an agent binds. These assays are useful for examining the binding affinity and/or specificity of various agents for nascent polypeptides. Such studies are of particular use in drug studies, both to analyze the interaction between a drug and an intended target polypeptide, but also to identify possible off-target effects caused by interaction with polypeptides other than the target polypeptide. Such off-target effects underlie many adverse events in patients, as well as many new and beneficial uses for known drugs.

It is to be understood that the above description is intended to be illustrative and not restrictive. It readily should be apparent to one skilled in the art that various embodiments and modifications may be made to the invention disclosed in this application without departing from the scope and spirit of the invention. The scope of the invention should, therefore, be determined not with reference to the above description, but should instead be determined with reference to the appended claims, along with the full scope of equivalents to which such claims are entitled. All publications mentioned herein are cited for the purpose of describing and disclosing reagents, methodologies and concepts that may be used in connection with the present invention. Nothing herein is to be construed as an admission that these references are prior art in relation to the inventions described herein. Throughout the disclosure various patents, patent applications and publications are referenced. Unless otherwise indicated, each is incorporated herein by reference in its entirety for all purposes.

What is claimed is:

1. A method of determining a sequence of amino acids encoded by a target mRNA molecule, comprising:
    a) providing a reaction mixture comprising the target mRNA molecule, a ribosome, an fMet-tRNA$^{fMet}$ in a P site of the ribosome, and a plurality of types of labeled aminoacyl-tRNAs free in solution, wherein the ribosome and/or the target mRNA molecule is immobilized upon a support such that an observation volume contains no more than one ribosome and/or mRNA molecule, and further wherein the ribosome does not comprise a detectable label or a quenching group, wherein each type of labeled aminoacyl-tRNA comprises a different detectable label that does not undergo FRET with other detectable labels on other reactants in the reaction mixture;
    b) initiating a processive translation of the mRNA molecule by the ribosome;
    c) during said processive translation, sequentially and optically detecting association of the ribosome with at least a first labeled aminoacyl-tRNA to produce a first signal, a second labeled aminoacyl-tRNA to produce a second signal, and a third labeled aminoacyl-tRNA to produce a third signal, where said association results in an incorporation of a first amino acid from the first labeled aminoacyl-tRNA, a second amino acid from the second labeled aminoacyl-tRNA, and a third amino acid from the third labeled aminoacyl-tRNA into a nascent polypeptide chain;
    d) validating the incorporation of the first amino acid into the nascent polypeptide chain, wherein said validating the incorporation of the first amino acid comprises detecting an overlap between the first signal and the second signal;
    e) validating the incorporation of the second amino acid into the nascent polypeptide chain, wherein said validating the incorporation of the second amino acid comprises detecting an overlap between the second signal and the third signal; and
    f) identifying the first amino acid and the second amino acid, thereby determining a sequence of amino acids encoded by the target mRNA molecule.

2. The method of claim 1, wherein at least 4-20 labeled aminoacyl-tRNAs are present in the reaction mixture.

3. The method of claim 1, wherein the reaction mixture further comprises EF-Tu comprising a quencher that quenches signal emitted from the labeled aminoacyl-tRNAs.

4. The method of claim 1, wherein the reaction mixture further comprises at least one of the group consisting of detectably labeled EF-Tu, detectably labeled EF-G, and detectably labeled GTP.

5. The method of claim 4, wherein none of the detectably labeled EF-Tu, the detectably labeled EF-G, and the detectably labeled GTP comprises a FRET label.

6. The method of claim 1, wherein the target mRNA molecule is a circular mRNA molecule or a concatemer mRNA molecule, and further wherein the sequence of amino acids is determined multiple times and redundant polypeptide sequence read data is generated.

7. The method of claim 1, wherein each of the plurality of types of labeled aminoacyl-tRNAs comprises (i) a different amino acid and a label that distinguishes the different amino acid from other amino acids in others of the plurality of types of labeled aminoacyl-tRNAs, and (ii) an anticodon that is complementary to a codon that may be present in the target mRNA molecule.

8. The method of claim 1, wherein the target mRNA molecule is a concatemer mRNA molecule.

9. The method of claim 8, wherein the concatemer mRNA molecule is a product of transcription of a circular DNA template molecule.

10. The method of claim 1, wherein the reaction mixture further comprises aminoacyl-synthetases.

11. The method of claim 10, wherein the aminoacyl-synthetases are bound to beads in the reaction mixture.

12. The method of claim 1, wherein the observation volume that contains said one ribosome and/or mRNA molecule is within an optical confinement comprising a physical barrier to isolate said one ribosome and/or mRNA molecule.

13. The method of claim 12, wherein the optical confinement is a pore in a layer overlaying a solid surface of the support on which said ribosome and/or mRNA molecule is immobilized.

14. The method of claim 13, wherein the optical confinement is a zero-mode waveguide.

15. The method of claim 1, wherein the processive translation comprises a plurality of sequential amino acid incorporation events catalyzed by the ribosome in the absence of any substantial changes to the reaction mixture aside from those catalyzed by the ribosome.

16. The method of claim 1, wherein the reaction mixture further comprises at least one labeled aminoacyl-tRNA comprising a detectable label that is a FRET label.

* * * * *